United States Patent [19]
Natan et al.

[11] Patent Number: 6,149,868
[45] Date of Patent: Nov. 21, 2000

[54] SURFACE ENHANCED RAMAN SCATTERING FROM METAL NANOPARTICLE-ANALYTE-NOBLE METAL SUBSTRATE SANDWICHES

[75] Inventors: Michael J. Natan; Christine Keating, both of State College, Pa.

[73] Assignee: The Penn State Research Foundation, University Park, Pa.

[21] Appl. No.: 09/181,291

[22] Filed: Oct. 28, 1998

Related U.S. Application Data

[60] Provisional application No. 60/063,688, Oct. 28, 1997.

[51] Int. Cl.$^7$ .................................................. G01N 21/65
[52] U.S. Cl. ........................ 422/82.05; 436/164; 356/301
[58] Field of Search ............................ 422/82.05, 82.09; 436/525, 164, 166, 805; 250/458.1, 459.1; 356/301

[56] References Cited

U.S. PATENT DOCUMENTS

| | | | |
|---|---|---|---|
| 5,266,498 | 11/1993 | Tarcha et al. | 436/525 |
| 5,445,972 | 8/1995 | Tarcha et al. | 436/544 |
| 5,552,086 | 9/1996 | Siiman et al. | 252/408.1 |
| 5,567,628 | 10/1996 | Tarcha et al. | 436/525 |
| 5,609,907 | 3/1997 | Natan . | |
| 5,828,450 | 10/1998 | Dou et al. | 356/301 |

OTHER PUBLICATIONS

Surface–Enhanced Raman Scattering (SERS) from Azobenzene Self–Assembled "Sandwiches", Hua–Zhong Yu, et al., Langmuir, vol. 15, No. 1, 1999, pp. 16–19.

"Protein:Colloid Conjugates for Surface Enhanced Raman Scattering: Stability and Control of Protein Orientation", Christine D. Keating, et al, J. Phys. Chem. B, vol 102 No. 47, pp. 9404–9413, 1998.

"Heightened Electromagnetic Fields Between Metal Nanoparticles: Surface Enhanced Raman Scattering from Metal–Cytochrome c–Metal Sandwiches", Christine D. Keating, et al, J. Phys. Chem. B, vol. 102, No. 47, pp. 9414–9425, 1998.

*Primary Examiner*—Jeffrey Snay

[57] ABSTRACT

A substrate for surface enhanced Raman scattering (SERS) is described in which the analyte is deliberately sandwiched between a colloidal metal nanoparticle and the SERS substrate. In a first embodiment, the analyte is a protein, and the sandwich comprises a protein:Au colloid complex adsorbed to an aggregated Ag sol. Another embodiment concerns a protein:Ag complex, adsorbed to an aggregated Ag sol. In another embodiment, a protein:Au colloid complex is covalently or non-covalently attached to a macroscopic SERS-active substrate. In yet another embodiment, the colloidal nanoparticle is stabilized by a polymeric additive. In yet another embodiment, detection is accomplished at extremely low analyte concentrations. In a final embodiment, control of analyte orientation with respect to the SERS substrate is demonstrated.

31 Claims, 42 Drawing Sheets

SURFACE ENHANCED RAMAN SCATTERING FROM METAL NANOPARTICLE-ANALYTE-NOBLE METAL SUBSTRATE SANDWICHES

This application claims the benefit of U.S. Provisional Application Ser. No. 60/063,688, filed Oct. 28, 1997.

FIELD OF THE INVENTION

This invention relates to investigation and/or detection of substances using surface enhanced Raman scattering (SERS) measurements, and more particularly, to a nanometer-scale structure from which such measurements are made.

BACKGROUND OF THE INVENTION

In surface enhanced Raman scattering (SERS), substances in close proximity to nanometer-scale roughened noble metal surfaces exhibit large (up to $10^6$-fold) enhancements in vibrational spectral intensities. When a laser used to excite SERS is in resonance with an electronic transition of the substance (surface enhanced resonance Raman scattering or "resonant SERS"), an additional $10^3$-fold enhancement is seen. Accordingly, SERS has been utilized in a wide variety of applications, including detection of molecules, elaboration of structure and function of large biomolecules, and elucidation of chemistry occurring at metal, metal oxide, and polymer surfaces, to name a few.

The literature teaches many approaches for creation, fabrication, or assembly of structures with the requisite nanoscale roughness. These include evaporated metal films, aggregated colloidal metal sols, electrochemically-roughened macroscopic electrodes, and a host of others. In all these approaches, the substance being studied by SERS is placed in direct or close contact with the surface.

These substrates have been of limited utility for studies of biomolecules. For uncoated SERS substrates, there is typically biomolecule denaturation (Smulevich, G.; Spiro, T. G. *J. Phys. Chem.* 1985, 89, 5168–5173; Holt, R. E.; Cotton, T. M. *J. Am. Chem. Soc.*, 1987, 109, 1841–1845). In contrast, biomolecules conjugated to colloidal Au nanoparticles retain their biological activity (Hayat M. A., Ed.; *Colloidal Gold: Principles, Methods, and Applications,* 3 vols.; Academic Press: New York, 1989), but the SERS intensities for such species by themselves have been weak (Garrell, R. L. *Anal. Chem.* 1989, 61, 410A–411A; Brandt, E. S.; Cotton, T. M. In *Investigations of Surfaces and Interfaces-Part B*; Rossiter B. W. and Baetzold R. C., Eds.; 2nd ed., John Wiley & Sons: New York, 1993; Chapter 8). Moreover, SERS has been of little value for studies of proteins whose chromophores are "buried" within the structure of the protein, and thus $\square$10 Å away from the metal substrate. For example, cytochrome $c_3$, a protein composed of four subunits that each contain a c-type heme moiety, exhibits SERS scattering for only one of the heme groups—that which is closest to the Ag substrate surface (Eng, L. H.; Schlegel, V.; Wang, D.; Neujahr, H. Y.; Stankovich, M. T.; Cotton, T. *Langmuir* 1996, 12, 3055–3059). This inability to observe SERS signals from even resonantly-enhanced chromophores within proteins results from the exponential dropoff in electromagnetic field away from the substrate surface. Finally, in the cases where SERS spectra can be obtained from adsorbed proteins, there is no control over protein orientation with respect to the surface, or over the conformational stability of the adsorbed protein over time.

An additional weakness of previously-described substrate architectures for SERS is their inability to rationally exploit what are known to be optimal SERS nanostructures. Early SERS work showed that electrochemical roughening of Ag electrodes in the presence of analyte molecules led to increased enhancements, a result verified by more recent experiments (Wolkow, R. A.; Moskovits, M. *J. Chem. Phys.* 1992, 96, 3966–3980; Gu, X. J.; Akers, K. L.; Moskovits, M. *J. Phys. Chem.* 1991, 95, 3696–3700.). This effect has been attributed to the entrapment of analyte molecules within the newly-formed Ag nanostructures. SERS studies using evaporated and cold-deposited Ag films suggested that the molecules responsible for the observed signal are located in crevices or pores in the films (Osawa, M.; Yamamoto, S.; Suetaka, W. *Appl. Surf. Sci.* 1988, 33/34, 890–897). In each system studied, it was postulated that the increased SERS signals resulted from the greatly enhanced electromagnetic (EM) fields that are possible between surface features. Theoretical calculations have shown that the electromagnetic fields in nanoparticle arrays are position-dependent. (Liver, N.; Nitzan, A.; Gersten, J. I. *Chem. Phys. Lett.* 1984, 111, 449–454).

There have been a number of studies in which the placement of the analyte relative to one SERS-active substrate has been controlled: using an organic or inorganic spacer, it is possible to control the distance between the analyte and SERS substrate over the zero Ångstrom (i.e. directly adsorbed) to few hundred Ångstrom regime (e.g. Ye, Q.; Fang, J.; Sun, L. *J. Phys. Chem. B* 1997, 101, 8221–8224). In this way, the relative contributions of the chemical enhancement and the electromagnetic enhancements to SERS have been elaborated, as well as the distance dependence of the latter.

Likewise, there have been a number of resonant SERS studies of the heme protein cytochrome c (Cc) directly adsorbed to SERS-active substrates (MacDonald, I. D. G.; Smith, W. E. *Langmuir* 1996, 12, 706–713; Hildebrandt, P.; Stockburger, M. *Biochemistry* 1989, 28, 6710–6721; Hildebrandt, P.; Stockburger, M. *Biochemistry* 1989, 28, 6722–6728.; Sibbald, M. S.; Chumanov, G.; Cotton, T. M. *J. Phys. Chem.* 1996, 100, 4672–4678). This work has exploited the facts that the heme group of Cc is an intense chromophore and that the heme of Cc is very near the surface of the protein, at a cleft rich in positively-charged surface lysine residues. Since the surfaces of SERS-active surfaces are typically negatively-charged, this lysine-rich patch binds to the metal surface. To a first approximation, on vibrations perpendicular to the SERS substrate experience enhancement. However, in previous studies of Cc SERS, it has not been possible to control the angular orientation of the heme with respect to the SERS-substrate.

Ideally, an analyte would be sandwiched between two SERS-active substances in a known and controllable orientation. Moreover, it would be ideal if the relative contributions of the two substances could be elaborated, via the wavelength dependence of the SERS enhancements. Moreover, it would be ideal if such a sandwich could be demonstrated to yield improved stability toward deleterious changes in the structure of the analyte relative to the case where the analyte is directly adsorbed to one substrate. Furthermore, it would be ideal if such sandwiches could be prepared using vanishingly small quantities of the analyte; it would be of further benefit if it could be known that each molecule of analyte were attached to a least one member of the sandwich.

Accordingly, it is an object of this invention to provide a deliberately-prepared sandwich structure for SERS comprising an analyte complexed to a colloidal noble metal particle that is either adsorbed or covalently-attached to another SERS substrate.

It is another object of this invention to provide a deliberately-prepared sandwich structure for SERS in which the orientation of the analyte with respect to the two SERS-active components of the sandwich can be controlled.

It is a further object of this invention to provide a deliberately-prepared sandwich structure for SERS wherein the amount of analyte in which the amount analyte in the sample is exceedingly low.

SUMMARY OF THE INVENTION

A sandwich architecture for SERS is described wherein the SERS analyte is deliberately placed between a colloidal metal nanoparticle and another SERS-active substrate. The analyte is associated with the colloidal metal nanoparticle; when the analyte:colloid complex is brought into close juxtaposition to a pre-formed SERS active substrate, either by adsorption or by covalent attachment, the sandwich is formed.

DETAILED DESCCIPTION OF THE INVENTION

Figure 1:
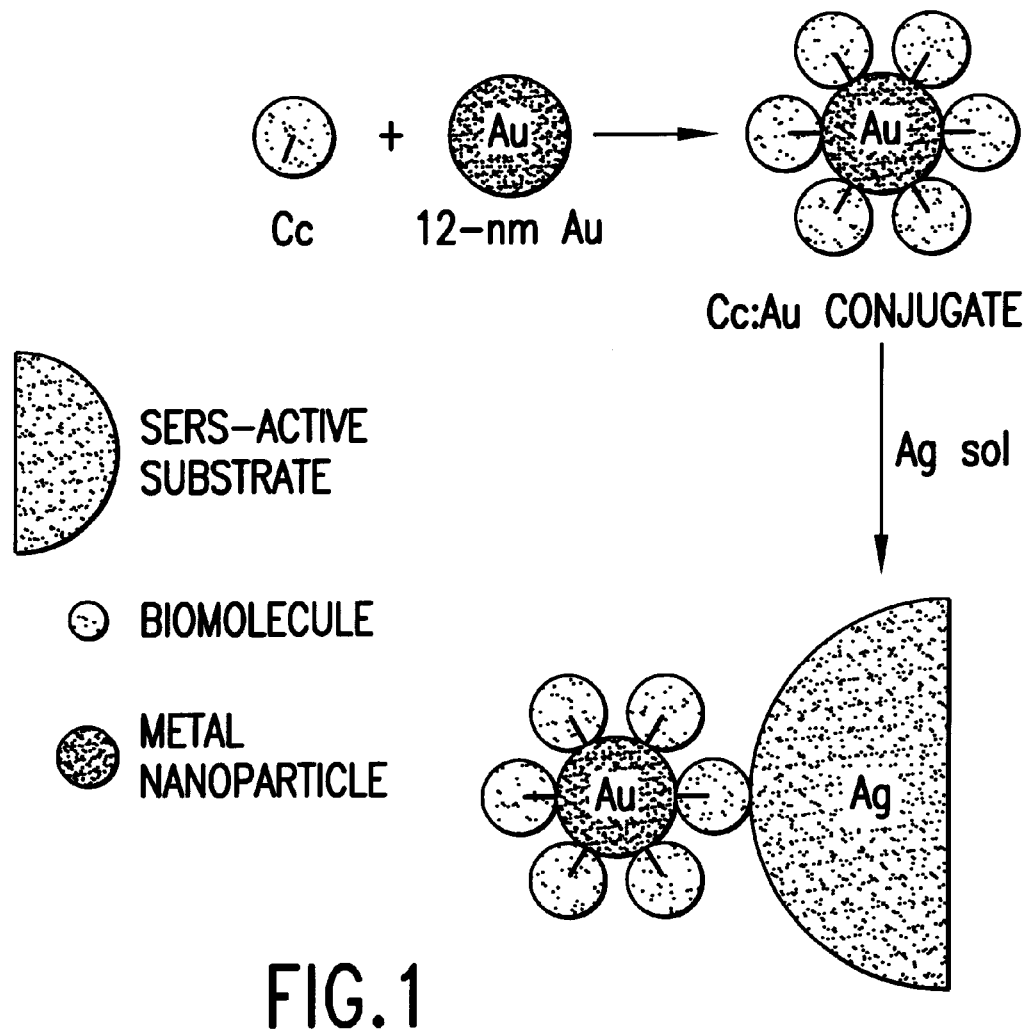
FIG. 1 shows a schematic representation of preparation of Ag:Cc:Au sandwiches for SERS. In this and all that follows, we adopt a Metal:Cc:Metal notation, in which the metal to right of the Cc always refers to the metal nanoparticle of the Cc:metal nanoparticle complex, and the metal the left of the Cc always refers to the "macroscopic" SERS substrate, typically an aggregation of colloidal metal nanoparticles. For example, Ag:Cc:Au refers to Cc:Au nanoparticle conjugates adsorbed at the surface of aggregated colloidal Ag.

Described herein is a method that takes advantage of both the high SERS enhancements at "bulk" SERS substrates (either aggregated colloidal Ag sols or macroscopic Ag surfaces) and the reproducibility and control over protein surface coverage possible at protein:colloidal Au conjugates. By adsorbing biomolecule-coated Au nanoparticles to colloidal Ag aggregates, a metal-biomolecule-metal sandwich is prepared (FIG. 1). Such an approach not only has favorable consequences vis à vis biomolecule stability and control of biomolecular orientation, but also leads to heightened electromagnetic fields (and, thus, increased SERS enhancement factors) between the Ag and Au surfaces. This approach effectively circumvents the normal distance dependence for SERS, and enables spectra to be acquired for an analyte containing a functional group located on the far side of the bulk SERS substrate.

This "sandwich" approach has several additonal attractive features. (i) Two colloidal metal particles can be placed a known distance apart, namely the biomolecular diameter. (ii) The choice of Au particles and bulk Ag substrates (or any combination with non-identical SERS-active species) allows the contributions to the overall electromagnetic enhancement to be clearly identified for each component through wavelength-dependent measurements of SERS spectral intensities.

It is important to point out that this invention clearly differs from simple aggregations of SERS-active nanoparticles such as Ag, Au, or Cu, in which the minimum distance between pairs of particles is zero (i.e. they are in contact). Likewise, it is to be distinguished from examples where two SERS-active substances are broug What follows are experimental details associated with sample preparation and data acquisition. Horse heart cytochrome c was purified by affinity chromatography according to standard protocols. "60-nm" Au particles were purchased from a commercial source and had a mean diameter of 62.8 nm. Polyethylene glycol (PEG, MW 20,000), horseradish peroxidase (type VI-A) (HRP) and all other reagents were acquired from commercial sources. All $H_2O$ was 18.2 M☐. The pH of colloid solutions was determined using pH test strips to within ±0.5 pH unit.

Ag sols were prepared by aqueous reduction of $AgNO_3$ with trisodium citrate. Ag sols prepared in this way are polydisperse, with average particle diameters typically ~30 nm and standard deviation of ±25 nm. 12-nm diameter colloidal Au was prepared by citrate-reduction of $HAuCl_4$. Particles referred to as "12-nm Au" were nearly spherical, with standard deviations in diameter <1.5 nm. Particles referred to as "40-nm Au" were prepared by using 12-nm Au particles as "seeds" for nucleation of larger particles. 1.5 mL of 1% $HAuCl_4$ was added to 128 mL of $H_2O$, and this solution was heated to a boil, with rapid stirring. Then, a solution prepared by mixing 3.0 mL of 17.8 nM, 12-nm Au particles and 0.75 mL of 38.8 mM trisodium citrate was added all at once. The solution turned violet, followed by appearance of a red color. The solution was kept boiling and stirring vigorously for ~15 minutes after the addition of colloidal Au and trisodium citrate, during which time some $H_2O$ was added to replace volume lost to evaporation. The final volume was 132 mL. Analysis of transmission electron microscopy (TEM) images gave a major axis of 45.5 nm (±5.7 nm) and minor axis of 37.5 (±3.9 nm). Ag-coated Au particles (henceforth Ag/Au) were prepared by using 12-nm Au particles as "seeds" for nucleation of Ag. 50 mL of 17 nM, 12-nm Au particles was diluted with $H_2O$ to 200 mL and heated, with rapid stirring. Upon boiling, 5.0 mL of 10 mM $AgNO_3$ was added rapidly from a syringe. 1.0 mL of 1% trisodium citrate was also added at this time. At 5 min. intervals, additional 5.0 mL aliquots of 10 mM $AgNO_3$ were added, to a total of 30 mL. At the addition of the fourth aliquot of $AgNO_3$ solution, an additional 1.0 mL of 1% trisodium citrate was also added. The colloid solution was boiled and vigorously stirred throughout the additions, and for another 15 minutes, after which it was removed from heat and stirred until cooled. The resulting solution had an absorbance maximum at 392 nm, with an absorbance of 1.7 after dilution 1:10 with $H_2O$. TEM analysis of these particles showed the presence of large (14–25 nm diameter) spheroidal particles and tiny particles (4–8 nm diameter). The absence of any 12-nm particles indicated that all the Au nanoparticles had been coated with Ag, yielding the larger particles. The concentration of Ag/Au nanoparticles in this solution was calculated to be ~$4\times10^{-11}$ M, based on the initial concentration of 12-nm Au "seed" particles.

EDTA-reduced Ag sols were prepared using the following procedure. 100 mL of $H_2O$ was brought to boil with rapid stirring. To this, 1.0 mL of 0.1 M EDTA and 4.0 mL of 0.1 M NaOH were added at once, followed by 1.3 mL of 0.1 M $AgNO_3$. The solution was boiled for 60 s, after which 300 µL of 0.1 M HCl was added and the solution was kept boiling and stirring for 2–3 min. The resulting solution was a bright yellow color; a 7% aqueous solution gave an absorbance of 1.43 at $\lambda_{max}$ (408 nm). TEM analysis of this colloid showed the presence of 14 nm (±8 nm) diameter Ag nanoparticles.

Cc:Au colloid conjugates were prepared using horse heart ferricytochrome c ($Fe^{3+}$) and 12-nm diameter colloidal Au. The binding of Cc to colloidal Au particles was followed by a flocculation assay. In this assay, increasing concentrations of protein were added to otherwise identical aliquots of Au hydrosol. Then, an aggregating agent (NaCl) was added to each solution. The amount of Cc necessary to prevent aggregation by NaCl was determined using optical spectra of the Au sol as indicator of aggregation. To prepare Cc:Au conjugates, a 10–50% excess of the minimum stabilizing concentration of Cc was added to a phosphate-buffered, pH 9.5 (±0.5) solution of Au sol. The solution was mixed gently and allowed to react for a few minutes before at 13,600 g. The supernatant was removed and the (soft) pellet resuspended in $H_2O$. Protein:colloid conjugates were stored at 4° C. when not in use. Under these conditions, Cc:Au(12-nm) samples were stable for several months.

Cytochrome c conjugates made with Ag-coated Au nanoparticles (Cc:Ag/Au) were prepared in a similar fashion. The saturating (Cc) was determined by a flocculation assay. Low-coverage Cc:Ag/Au conjugates were prepared by addition of 21% of the stabilizing (Cc). 110% of the stabilizing (Cc) was used in preparing the high-coverage conjugates. Both samples were prepared at pH 9.5±0.5. The resulting Cc:Ag/Au conjugates were purified by centrifugation and resuspension in $H_2O$.

HRP:Au colloid conjugates were prepared using horseradish peroxidase (HRP) and 12-nm diameter colloidal Au. The binding of Cc to colloidal Au particles was followed by a flocculation assay as described above. Conjugates were then prepared by addition of 100 μL of 9.7 mg/mL HRP to 1.20 mL of 14 nM, 12-nm diameter Au particles. The solution was mixed gently and allowed to react for 15 minutes before centrifugation in a Fisher Scientific Micro Centrifuge Model 235C for 15 minutes at 13,600 g. The supernatant was removed & the (soft) pellet resuspended in $H_2O$.

As-prepared 40-nm Au solutions were calculated to be 0.405 nM in particles, based on the assumption that all Au particles in the final solution were formed by growth of 12-nm "seed" particles. The narrow size distribution seen in TEM analysis of seeded colloid validates this assumption. The stabilizing concentration of Cc for 40-nm Au was determined by a flocculation assay, as described for 12-nm Au. A large excess (470%) of this value was added to the colloidal solution to prepare Cc:Au(40) conjugates, which were then incubated for 15 minutes and centrifuged 30 minutes at 13,600 g. The supernatant was removed and the (soft) pellet resuspended in $H_2O$. Cc concentration in these samples prior to centrifugation/resuspension was $3.64 \times 10^{-7}$ M.

Particles referred to as "60-nm" actually have particle diameters of 62.8 nm, a concentration of $2.6 \times 10^{10}$ particles/mL (43.2 pM in particles), and a coefficient of variation in particle diameter of <20%. A calculation for the number of Cc molecules necessary to completely coat 62.8-nm Au particles gave ~1500 Cc molecules per Au particle. Flocculation data indicated that about 20% more than this value was required. This excess could be accounted for by accumulated errors in particle concentration, particle diameter, and Cc "footprint" on Au. Conjugates were incubated for 15 min., then spun 10 min. at 13,600 g. Because the particles were so dilute, only very weak signal could be observed from conjugates resuspended in 1.25 mL; thus, conjugates were resuspended in 100 μL $H_2O$. Cc concentration in these samples prior to centrifugation/resuspension was $1.45 \times 10^{-7}$ M.

Cc:Ag conjugates were prepared by addition of 110% of the stabilizing concentration of Cc, as determined from flocculation studies, to EDTA-derived Ag (carried out as for Au). Thus, 50 μL of 10 μM Cc was added to 1.2 mL of Ag nanoparticles at pH 9.5±0.5. The resulting solution was incubated for 15 minutes, then centrifuged at 13,600 g for 15 minutes and resuspended in 1.25 mL of $H_2O$.

Typical SERS substrates were prepared as follows: 500 μL of Ag or Au sol was aggregated by addition of 5 μL of 5 M NaCl, after which 50 μL of protein or protein colloid conjugate was added immediately, followed by 50 μL of 1% agarose (Biorad, low-melt). The agarose was kept liquid just above the gel point on a hot plate prior to use. SERS samples were then transferred to borosilicate glass culture tubes for immediate spectral acquisition. Samples were freshly prepared for each spectrum; all spectra were acquired at room temperature. In the case of electrode SERS, a polished Ag electrode was subjected to oxidation-reduction cycles as described in the literature to achieve the desired roughness.

10–100 mW of laser power was used in SERS studies. Scattered light was collected in a backscattering geometry and focused into a triple monochromator fitted with either a 1200 or an 1800 gr/mm grating in the spectrograph stage and two 600 gr/mm gratings in the filter stage. Detection was accomplished using a charge-coupled device detector cooled to 140 K. The spectrometer was calibrated using imidazole as a frequency standard prior to each set of experiments, and was recalibrated whenever the excitation wavelength was changed.

Now described are data describing the coating of particles by protein. The concentration of Cc necessary to coat each Au nanoparticle in a 17.8 nM solution of colloidal Au was determined by finding the minimum Cc concentration capable of preventing electrolyte-induced aggregation of the Au sol. The surface plasmon resonance of isolated Au particles is at ~520 nm. Addition of electrolytes to Au hydrosols causes particle flocculation due to screening of the repulsive double layer charges that normally stabilize them, leading to the appearance of a broad absorbance at long wavelengths (~650 nm). This feature increases in intensity and/or broadens and redshifts with increasing aggregation. Flocculation can be prevented by adsorption of stabilizers, such as polymers or proteins, to the sol; these large adsorbates cause steric repulsions between the particles. The amount of stabilizer necessary to prevent aggregation upon the addition of electrolyte can be determined from a flocculation assay.

Figure 2A:
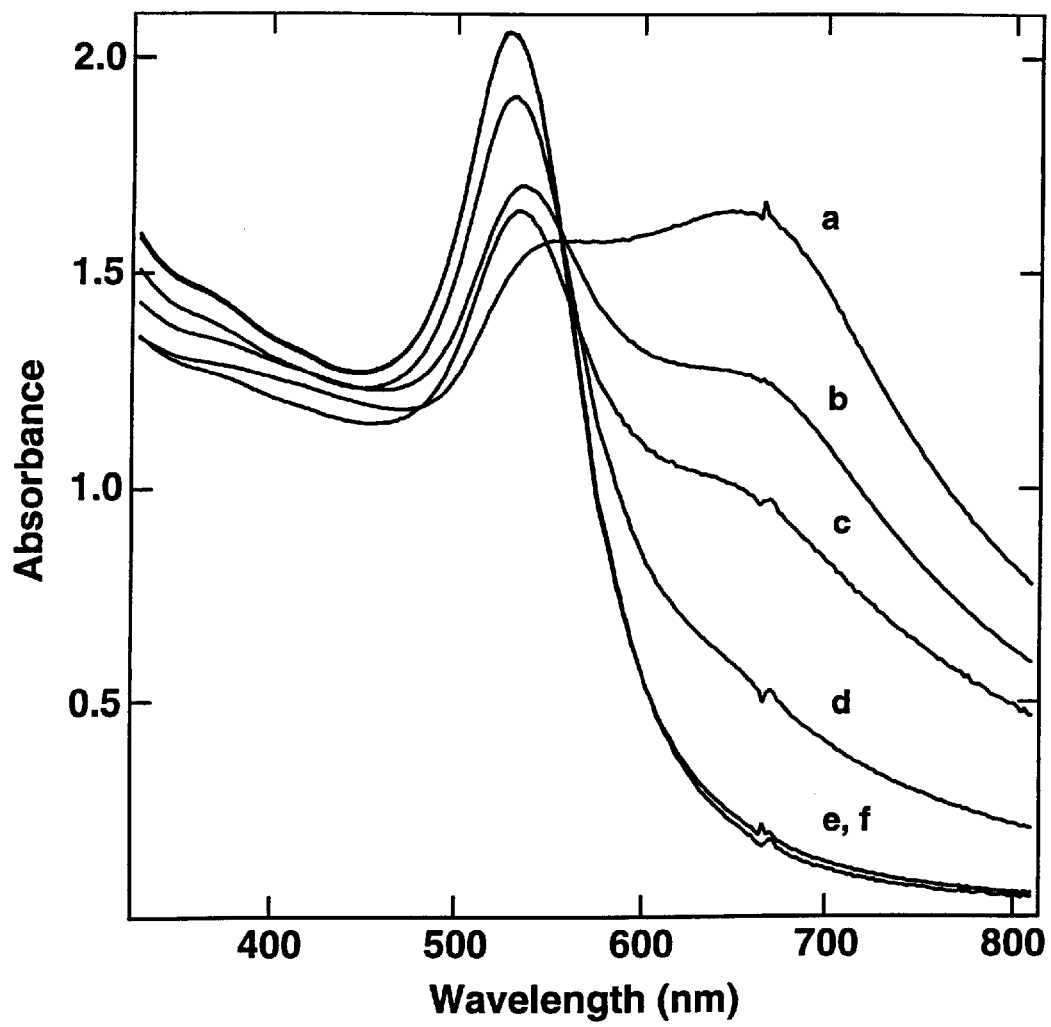
FIG. 2A shows flocculation data for Cc on 12-nm diameter colloidal Au.
Figure 2B:
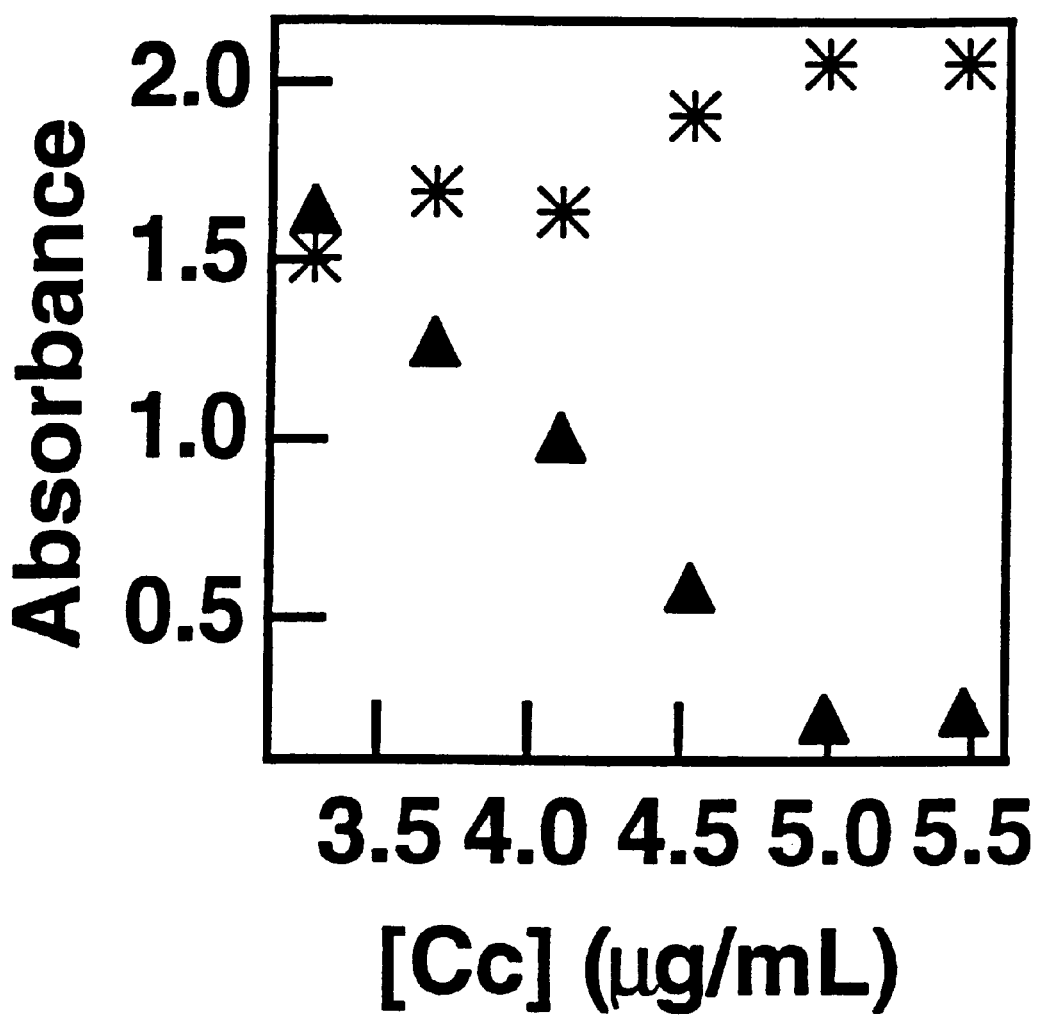
FIG. 2B shows absorbance at 520 nm (♦) and at 650 nm (*) vs. (Cc).

FIG. 2A shows flocculation data for increasing concentrations of Cc in aliquots of 12-nm Au nanoparticles. pH 9.5 was chosen for these experiments, since at higher pH the bare Au sol is unstable, and at lower pH the Cc is able to crosslink Au particles, causing aggregation. At pH 9.5, Cc is expected to bind to the negatively-charged Au nanoparticles through its lysine-rich heme pocket (at lower pH, a second, weakly positive patch on the opposite side of the protein also binds Au). In these experiments, 500 μL of 1.5 M NaCl was added to 3.07 mL of 12 M, 12-nm Au particles containing varying concentrations of Cc: (a) 3.3 μg/mL; (b) 3.7 μg/mL; (c) 4.1 μg/mL; (d) 4.5 μg/mL; (e) 5.0 μg/mL; and (f) 5.5 μg/mL. Spectra were taken 15 min. after addition of NaCl. The sample in spectrum (a) contains only 3.3 μg/mL Cc, which is insufficient to prevent aggregation upon addition of NaCl. Lesser amounts of aggregation (lower absorbance at ~650 nm) are visible as (Cc) is increased, until, at 5.0 μg/mL, no further change is observed, and the spectrum is very similar to that of isolated Au nanoparticles. FIG. 2B plots sample absorbance at 520 nm and 650 nm versus (Cc).

The lowest ratio of Cc to Au nanoparticles that prevented aggregation in this experiment was ~30 Cc per Au particle. This result is consistent with ~0.6 monolayers of 34-Å diameter spheres packed around each of the 12-nm diameter Au particles, assuming that no Cc remained free in solution. In other flocculation studies of Cc added to 12-nm Au, values as high as ~50 Cc/Au (a full monolayer) were obtained; the results are highly dependent on the pH of the colloid solution, with greater stabilization occurring at higher pH. Note that less than a monolayer of protein is effective at (sterically) inhibiting particle flocculation.

Figure 3:
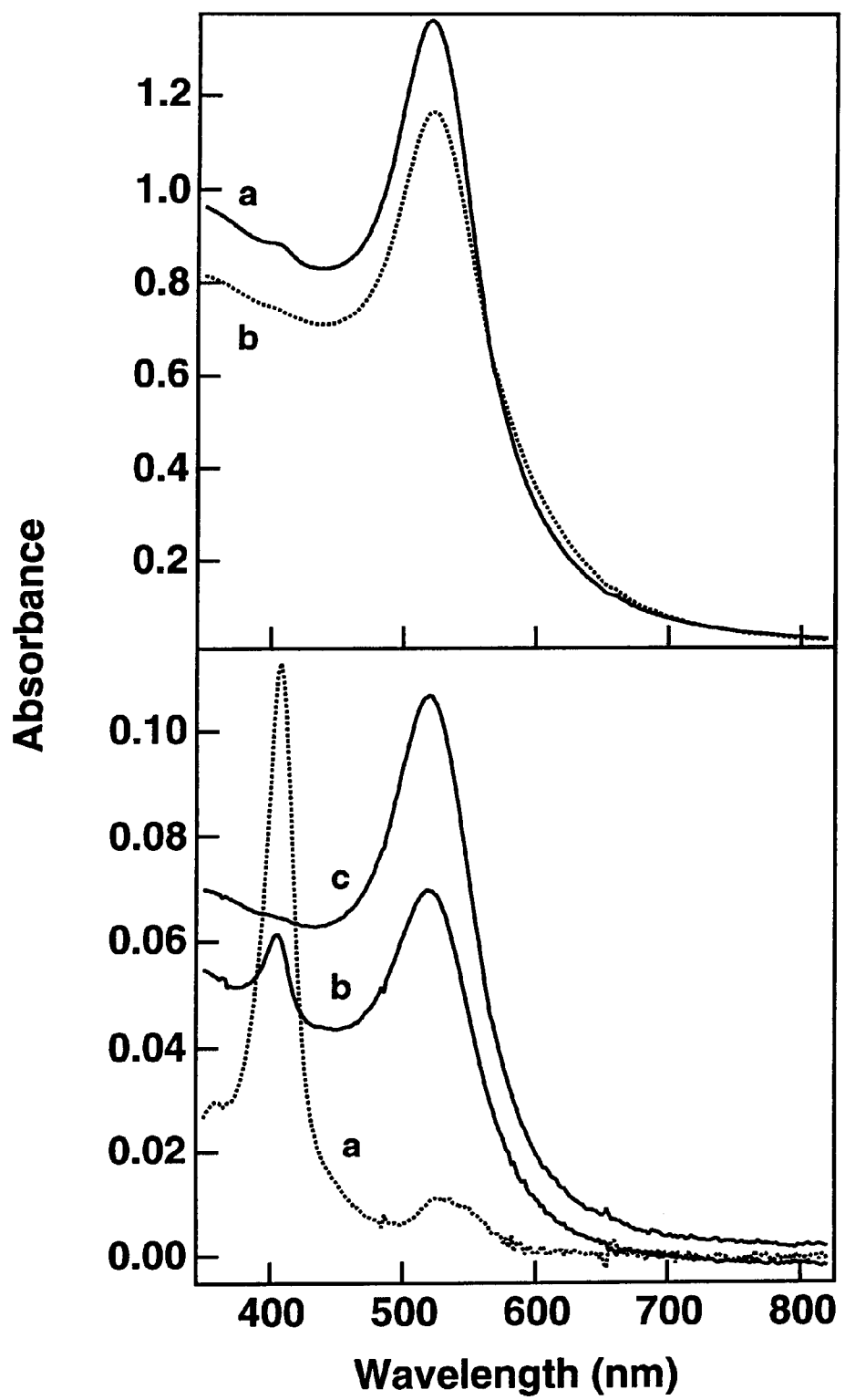
FIG. 3 shows optical spectra for conjugates of Cc with 12-nm diameter colloidal Au prior to centrifugation (a) and after centrifugation and resuspension twice (b) (top), and optical spectra for: $1.4 \times 10^{-6}$ M Cc (a) and supernatants from the first (b) and second (c) centrifugation of Cc:Au (bottom).

Cytochrome c:12-nm diameter Au nanoparticle conjugates were prepared by adding a slight excess of Cc (110% of the stabilizing concentration, as determined by flocculation) to colloidal Au at pH ~9.5. The optical spectrum for this material is shown in the upper panel of FIG. 3, spectrum (a). Excess Cc was removed by centrifugation of the conjugate solution to produce a pellet (Au:Cc and any free Au), which was then resuspended in buffer; this procedure was done once or twice. An optical spectrum of the final Cc:Au conjugate solution is shown in the upper panel of FIG. 3, spectrum (b). The decreased absorbance shows that some Au has been lost in the centrifugation step. In addition, there is only slight broadening of the peak, indicating that very little, if any, aggregation has occurred. Optical spectra of the first and second supernatants are shown in the lower panel of FIG. 3, along with a spectrum of $1.36 \times 10^{-6}$ M Cc. Some Au nanoparticles remain in both supernatants, as evidenced by the absorbance at ~520 nm (note that the pellet is soft, thus a small amount of Cc:Au tends to be lost with the supernatant as it is decanted—this amount is greater in trace c than trace b). More importantly, optical spectra for the supernatants also indicate that some excess Cc was lost in the first round of centrifugation, but that much less Cc was present in the second supernatant (as evidenced by the smaller peak at 400 nm in the second supernatant).

Figure 4:
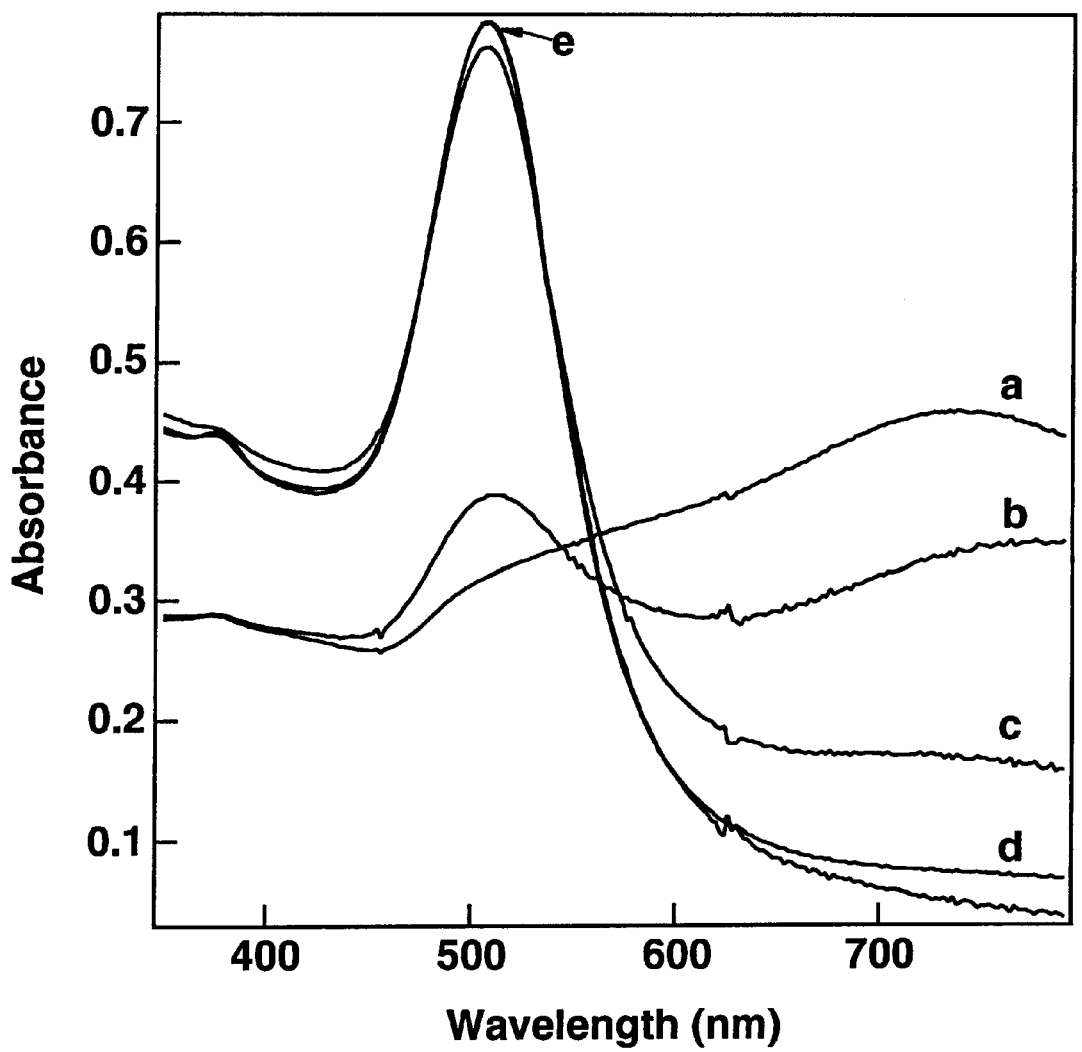
FIG. 4 shows flocculation data for Cc binding to $3 \times 10^{-10}$ M, 40-nm diameter colloidal Au particles. Ratio of Cc to colloidal particles: (a) 494:1; (b) 617:1; (c) 864:1; (d) 987:1; (e) 1728:1.
Figure 5:
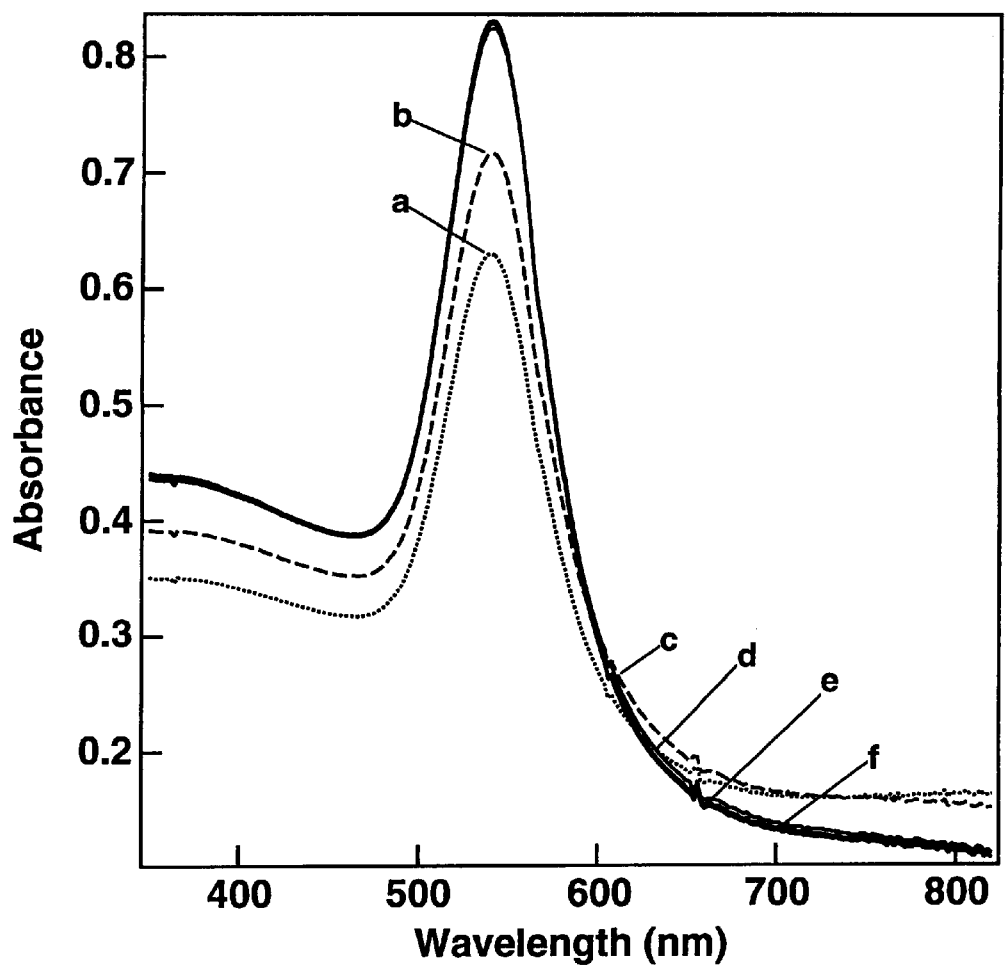
FIG. 5 shows flocculation data for Cc binding to $2.8 \times 10^{-11}$ M, 60-nm diameter colloidal Au particles. Ratio of Cc to colloidal particles: (a) 1329:1; (b) 1620:1; (c) 1852:1; (d) 2084:1; (e) 2315:1; (f) 2547:1.

Cc:Au conjugates were also prepared using larger Au nanoparticles, with polydisperse Ag nanoparticles, and with Ag-coated Au nanoparticles. For 40-nm and 60 nm diameter, spherical, monodisperse colloidal Au, flocculation assays showed essentially quantitative binding of Cc, as was observed for 12-nm Au (FIGS. 4 and 5). For the 60-nm Au flocculation, the long-wavelength absorbance feature is not as intense in corresponding spectra as for the 12-nm and 40-nm flocculation assays. However, the decrease in absorbance at ~534 nm is also indicative of aggregation. Flocculation assays gave ~1730 Cc/40-nm Au (0.8× that predicted value for a monolayer), and ~1850 Cc/60-nm Au particle (1.3× that predicted value for a monolayer). The higher (Cc) required to stabilize the commercially obtained 60-nm Au particles may be related to the presence of polymeric stabilizers in this solution, since transmission electron microscopy images revealed their presence; some of the Cc may have bound to these stabilizers rather than the Au. Cc:Au conjugates were prepared with 40- and 60-nm Au particles; these conjugates were similar to Cc:Au prepared using 12-nm Au, except for exhibiting a reduced stability that is typically associated with larger Au particles. After pelleting, Cc:Au can be resuspended in almost arbitrarily small volumes to prepare more concentrated solutions. This is particularly helpful for conjugates prepared with the very dilute 40- and 60-nm Au particles.

Figure 6A:
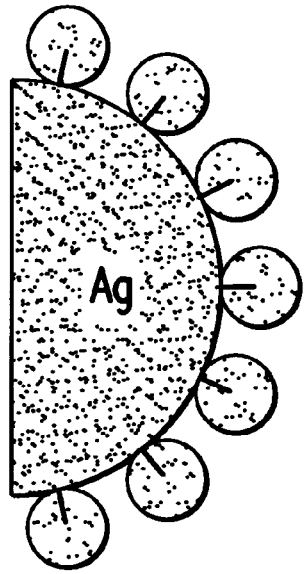
FIG. 6 depicts three geometries for Cc SERS spectra on aggregated Ag sols.
Figure 6B:
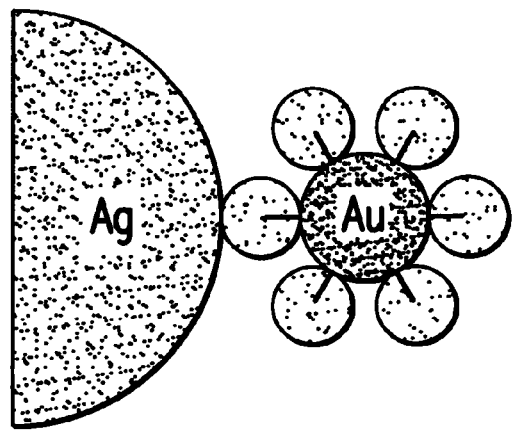
Figure 6C:
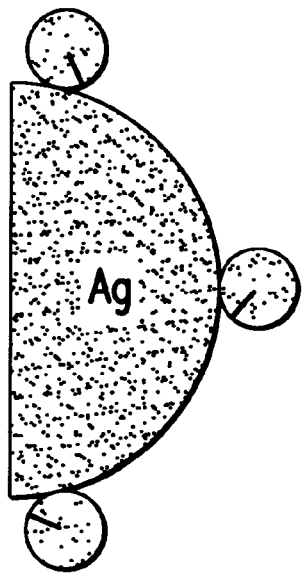

Ag:Cc:Au sandwiches are prepared by addition of Cc:Au conjugates to aggregated colloidal Ag as shown in FIG. 1. The two basic types of Cc SERS samples are shown in FIG. 6 (illustrations (A) and (B)). In both cases, the Ag nanoparticle in the diagram is an oversimplification of the actual Ag surface. In fact, the Ag is present as large, fractal aggregates of polydisperse Ag nanoparticles (mean diameter=30 nm). A represents Cc directly adsorbed to aggregated Ag sol (Ag:Cc), while B is Cc:Au adsorbed to the aggregated colloidal Ag (Ag:Cc:Au). Key aspects of these two geometries are the location of Cc's heme group relative to the Ag substrate (near the SERS-active Ag for A, distant in B), and the orientation of the heme plane relative to the surfaces. Both colloidal Ag and Au particles are negatively-charged, due to adsorbed citrate and chloride ions present during their preparation. Previous studies have shown that Cc adsorbs to negatively-charged surfaces with the heme group very close to the surface (Edmiston, P. L.; Lee, J. E.; Cheng, S. -S., Saavedra, S. S. *J. Am. Chem. Soc.* 1997, 119, 560–570); at high Cc coverages, the heme is oriented close to the surface normal, while at low coverages, the heme-surface angle decreases. Also important is the location of a second, weaker positive patch on the opposite side of the Cc molecule, facilitating "sandwich" formation. Previously reported SERS spectra for Cc derive almost exclusively from vibrations of the heme chromophore, which is covalently bound to the protein through the porphyrin substituents by two cysteine residues and by the Fe's two axial ligands, histidine and methionine.

The protein-colloid literature stresses the importance of additional polymeric adsorbates to stabilize conjugates, by occupying any sites left available on Au particles after binding the protein of interest. Such stabilizers are typically added in large excess prior to centrifugation, and again in the resuspension buffer. In one embodiment of this invention, we followed these protocols in preparing Cc:Au. These stabilizers (in particular, polyethylene glycol (PEG), fish gelatin, and bovine serum albumin) exhibit weak SERS spectra when adsorbed to colloidal Ag aggregates, and are able to compete to some extent with Cc:Au for adsorption sites on Ag aggregates due to their high solution concentration. This had the effect of partially masking SERS signal from the desired analyte. Now referring to Table I, SERS from the heme chromophore is observed for Cc directly

TABLE I

Frequencies and assignments for Cc heme vibrations

Figure 7:
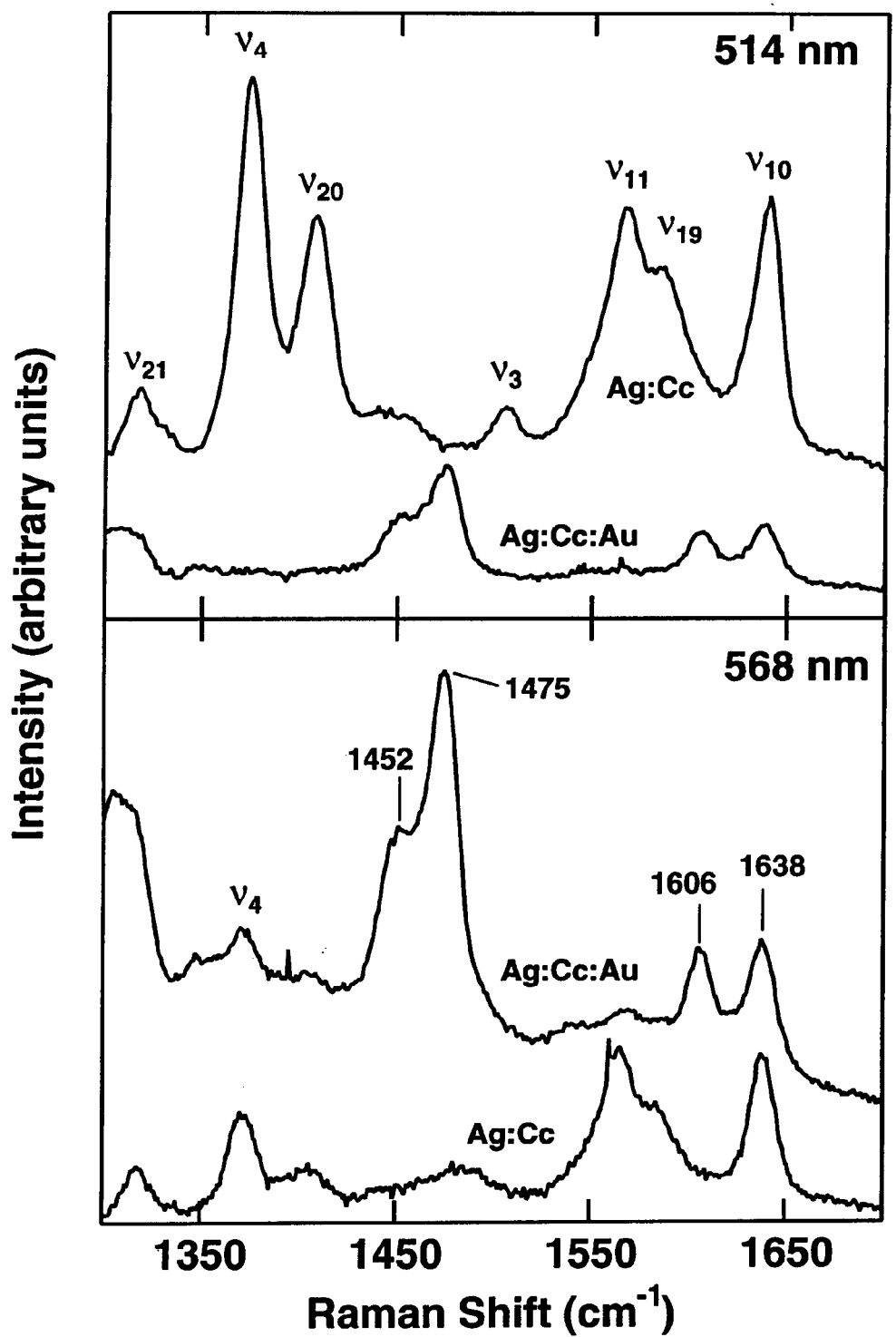
FIG. 7 shows SERS spectra, at aggregated Ag sol, for Cc (Ag:Cc) and for PEG-stabilized Cc:Au (Ag:Cc:Au) at 514.5 nm and 568.2 nm excitation.

| 488 nm | | 514.5 nm | | 568.2 nm | | 647.1 nm | | Assignment |
|---|---|---|---|---|---|---|---|---|
| A | B | A | B | A | B | A | B | (ref. 16) |
|  |  | 1316 |  | 1313 | 1313 | 1316 | 1317 | $v_{21}$ |
| 1373 |  | 1375 | 1376 | 1369 | 1368 | 1368 | 1368 | $v_4$ |
| 1402 |  | 1407 | 1404 | 1403 | 1404 | 1404 | 1404 | $v_{20}$ |
|  |  | 1450 | 1455 |  |  | 1444 | 1441 |  |
|  |  |  |  | 1487 | 1487 |  |  | a |
| 1502 |  | 1505 |  |  |  |  |  | $v_3$ |
| 1556 | 1558 | 1565 |  | 1561 | 1562 | 1555 | 1556 | $v_{11}$ |
| 1587 |  | 1585 |  | 1580 | 1579 | 1585 | 1585 | $v_{19}$ |
|  |  |  |  |  |  | 1611 | 1611 |  |
|  |  |  |  |  |  | 1627 | 1627 | b |
| 1637 |  | 1640 | 1641 | 1636 | 1637 |  |  | $v_{10}$ | a. Although this band is in the general region for high-spin $v_3$, it is only present with 568.2 nm excitation, and identically-prepared samples excited at other wavelengths give $v_3$ at 1503 cm$^{-1}$ (indicative of low-spin Fe); we find it unlikely that $v_3$ moves to 1487 cm$^{-1}$ only at $\lambda_{ex}$ = 568.2 nm, especially given that the other spin state marker bands all indicate low spin Fe. Thus, we have left this band unassigned.
b. The position of $v_{10}$ at 1627 cm$^{-1}$ observed for $\lambda_{ex}$ = 647.1 nm would indicate that the heme has undergone a spin-state conversion to a high spin Fe. Again, this seems unlikely to have occurred for only one excitation wavelength; thus, we have not assigned the 1627 cm$^{-1}$ band as $v_{10}$.

adsorbed to aggregated colloidal Ag (Ag:Cc), as evidenced by observation of the previously assigned bands $v_4$ (1375 cm$^{-1}$), $v_3$ (1505 cm$^{-1}$), $v_{10}$ (1640 cm$^{-1}$) and others. In contrast, considering FIG. 7, the spectrum for PEG-stabilized Cc:Au adsorbed to this substrate (Ag:Cc:Au) (acquisition conditions: (Cc)=7.5×10$^{-8}$ M; 10 s integration× 10 accumulations; 5 cm$^{-1}$ bandpass) is dominated by non-heme bands. Control experiments showed these bands to be related to the PEG stabilizer present in the Cc:Au solution, as folows. No vibrations attributable to heme were observed for PEG-stabilized Cc:Au at 647.1 or 488.0 nm excitation; for 568.2 nm excitation, however, weak heme vibrations are observable in the PEG-stabilized Cc:Au SERS at aggregated Ag.

Figure 8:
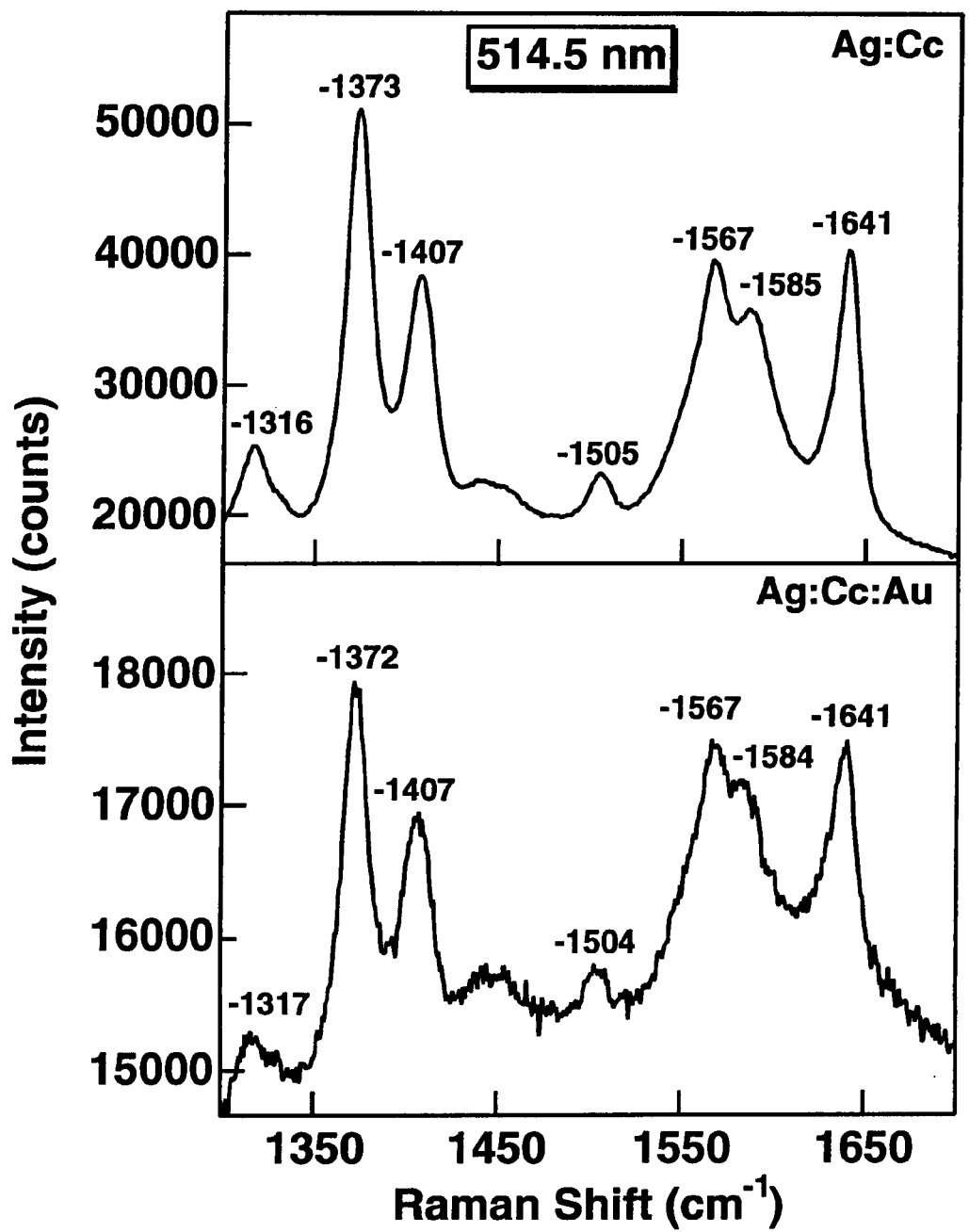
FIG. 8 shows SERS for Ag:Cc (top) and Ag:Cc:Au (bottom) with 514.5 nm excitation.

Other embodiments of this invention do not involve colloidal stabilizers. For example, SERS spectra at Ag aggregates for Cc (A in FIG. 6, Ag:Cc) and unstabilized Cc:Au conjugates (B in FIG. 6, Ag:Cc:Au) are shown in FIGS. 8 (514.5 nm excitation) and 9 (568.2 nm excitation); see FIG. 6 for the geometries of A and B. In these and subsequent figures, SERS spectra of Cc:Au conjugates are compared to those of the same concentration of Cc (as in the conjugate) adsorbed directly to aggregated Ag, under identical conditions. The Cc concentration in Ag:Cc and Ag:Cc:Au samples was equivalent. Stated another way, the top and bottom panels of FIG. 8 compare spectra for the same amounts of protein added to aliquots of the same aggregated Ag sol, excited at the same power (55 mW of 514.5 nm), with an identical integration time. In these examples, Ag:Cc and Ag:Cc:Au samples were freshly prepared and run one immediately after the other, with no change in beam steering or collection optics, so that they could be directly compared. The only difference in the experiment is that for the spectrum labeled Ag:Cc:Au, the Cc was conjugated to colloidal Au, whereas the spectrum labeled Ag:Cc, the Cc was added directly. The top and bottom panels of FIG. 8 are equally similar, except that the excitation wavelength is 568.2 nm.

Figure 9:
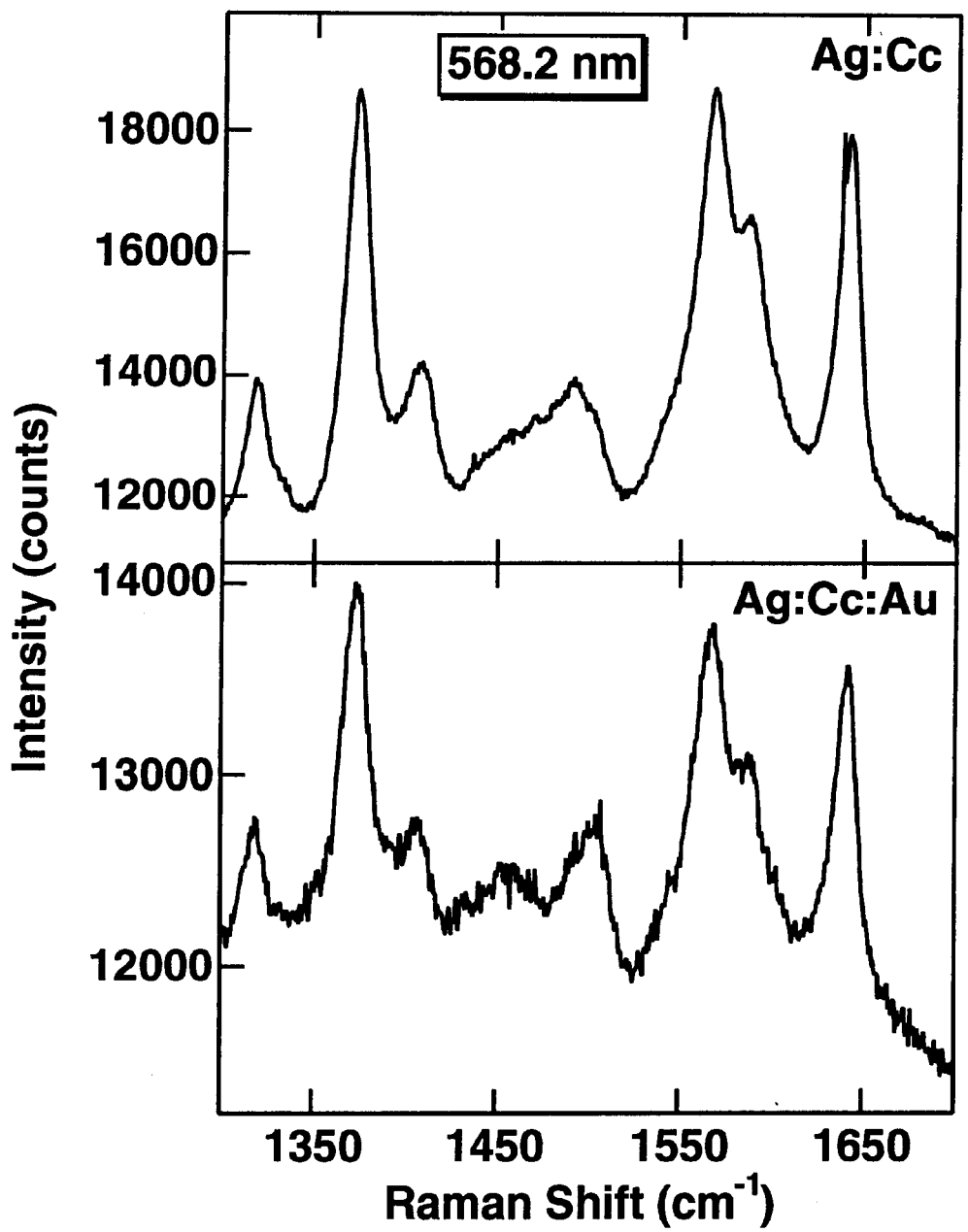
FIG. 9 shows SERS for Ag:Cc (top) and Ag:Cc:Au (bottom) with 568.2 nm excitation.

The greater SERS signal for Ag:Cc (A) than for Ag:Cc:Au (B) in FIGS. 8 and 9 is due to the location of the Cc heme in the two geometries, and provides strong evidence that Cc does not desorb from Cc:Au. In A, the heme group is located very close to the Ag surface, while in B, the heme group is close to the Au surface and far from the Ag. Since the SERS effect drops off exponentially with distance from the Ag substrate, much less signal is expected for the geometry shown in B than A. Indeed, the closest heme-Ag distance in B is nearly the same as for the 'buried' heme groups unobservable in SERS studies of the multi-heme protein, cytochrome c$_3$. Note that the SERS intensity differences observed at two different excitation wavelengths proves that Cc:Au remains intact upon adsorption. If Cc desorbed from the Au nanoparticles, it would be available for adsorption onto the aggregated Ag surface. Had all of the Cc desorbed and then bound to Ag, the two spectra in FIG. 8 would be identical. If only a fraction of the Cc migrated to the Ag surface, the SERS intensity observed for Ag:Cc:Au samples would be lower than that for Ag:Cc, as is observed in FIG. 8. However, with SERS enhancement coming only from the Ag surface, the relative intensities for the two samples would be independent of excitation wavelength. This is not observed: for $\lambda_{ex}$=568.2 nm, the SERS intensity of signal for Ag:Cc:Au is closer to that for Ag:Cc (they differ by a factor of ~3), while at $\lambda_{ex}$=514.5 nm, the SERS intensity for Ag:Cc greatly exceeds that for Ag:Cc:Au (they differ by a factor of ~10). The point is that differences in relative intensities for Ag:Cc and Ag:Cc:Au at different excitation wavelengths argues strongly against dissociation of Cc in Cc:Au.

SERS spectra for Ag:Cc and Ag:Cc:Au are very similar in terms of band positions. Thus, conjugation to colloidal Au prior to adsorption at aggregated Ag does not perturb the conformation of Cc. Furthermore, the spectra for $\lambda_{ex}$=514.5 nm (FIG. 8) are essentially identical to those previously observed at citrate-reduced Ag sols, and show no signs of Cc denaturation or conformational change at the surface.

The location of the $v_4$ vibration (oxidation state marker band) at 1375 cm$^{-1}$ is consistent with ferriCc, while the location of the spin-state marker bands (e.g. $v_{10}$ at 1640 cm$^{-1}$) is consistent with a low-spin, 6-coordinate heme. Cc SERS using 568.2 nm excitation has not appeared in the literature; however, most of the spectral differences between the Ag:Cc spectra excited at 568 nm and those with 514 nm excitation can be understood in terms of the wavelength dependence of Cc resonance Raman spectra (Cartling, B. *Biophys. J.* 1983, 43, 191–205). It should be noted that all of the spectra shown here report on the average heme environment, and do not preclude the possibility that a small fraction of Cc at the surface has undergone conformational changes.

While it has been shown previously that the angle of Cc's heme with respect to the surface changes with Cc coverage, Ag:Cc:Au retains its initial orientation at all Cc:Au coverages. Thus, a key advantage to the "conjugate approach" to protein SERS is that the conjugate can be made at one concentration relative to the carrier particle (i.e. colloidal Au) and the SERS measurement can be made at another. Moreover, the amount of protein required to make the conjugates is extremely low.

SERS selection rules can be used in some cases to determine bond orientations with respect to the enhancing substrate. For a heme chromophore having a symmetry of D$_{4h}$ (typically taken as model for Cc heme, although in Cc the Fe axial ligands differ; the same arguments obtain for C$_{4v}$), both totally symmetric modes (e.g. the A$_{1g}$ mode $v_4$) and non-totally symmetric modes (e.g. the B$_{1g}$ mode $v_{10}$) involve motion along the x- and y-axes (in the plane of the porphyrin), while the totally symmetric (A$_{1g}$) modes involve displacement along the x, y, and z directions. Due to the rhombic distortion of the heme in Cc, the actual symmetry is lower even than C$_{4v}$, making C$_s$ a better model. However, the normal mode analysis for Ni octaethylporphyrin (NIOEP), which has been the basis for all heme chromophore band assignments, initially treated the ethyl substituents as point masses, such that NiOEP had D$_{4h}$ symmetry; the labels have been carried over to molecules of lower symmetry. Nonetheless, the same arguments apply for Cc's heme, since the $v_{10}$ mode involves in-plane displacement while the $v_4$ mode has both in-plane and out-of-plane components.

The SERS effect preferentially enhances vibrations which involve a change in polarizability along an axis perpendicular to the surface. Thus, B$_{1g}$ modes would be expected to be large only when the heme in-plane vibrations have a large component perpendicular to the surface (that is, when the heme is "standing up"; in this orientation, A$_{1g}$ modes are also expected to exhibit good enhancement. For a heme group laying flat on the surface, only A$_{1g}$ modes are expected to scatter effectively. Thus, as the angle of the heme with respect to the surface normal increases, a relative increase in SERS intensity for totally symmetric modes over non-totally symmetric modes is predicted (i. e. the B$_{1g}$/A$_{1g}$ SERS intensity ratio decreases). The surface selection rules are most valid at long wavelengths (i.e. infrared) for several reasons. First, since metals have higher electrical conductivities at IR frequencies, the parallel (but not the perpendicular) electric field component of radiation goes to zero at the surface. However, since SERS experiments typically employ visible excitation (where substrates are poorer conductors), the non-totally symmetric modes are not expected to disappear completely even if they involve no change in polarizability perpendicular to the surface. Second, for Cc SERS, use of excitation wavelengths near the intense Soret absorption band (404 nm) favors contribution from resonance enhancement over surface enhancement. Excitation into the Soret band (404 nm) leads to A-term scattering, which favors totally-symmetric modes, while excitation into the weaker Q bands (530–550 nm) leads to B-term scattering, whereby the non-totally symmetric bands (which gain intensity through vibronic coupling) are favored. Thus, changing from 400 nm to 550 nm excitation, for example, should lead to a relative increase in $B_{1g}$ modes over $A_{1g}$ modes.

In practice, the relative intensity pattern observed in a SERS spectrum is due to a combination of several effects, making quantitative predictions of bond orientations from a single spectrum non-trivial. However, for spectra acquired at a given $\lambda_{ex}$, changes in the $B_{1g}/A_{1g}$ (e.g. $v_{10}/v_4$) ratio are expected upon changes in the orientation of the heme moiety with respect to the surface.

Figure 10:
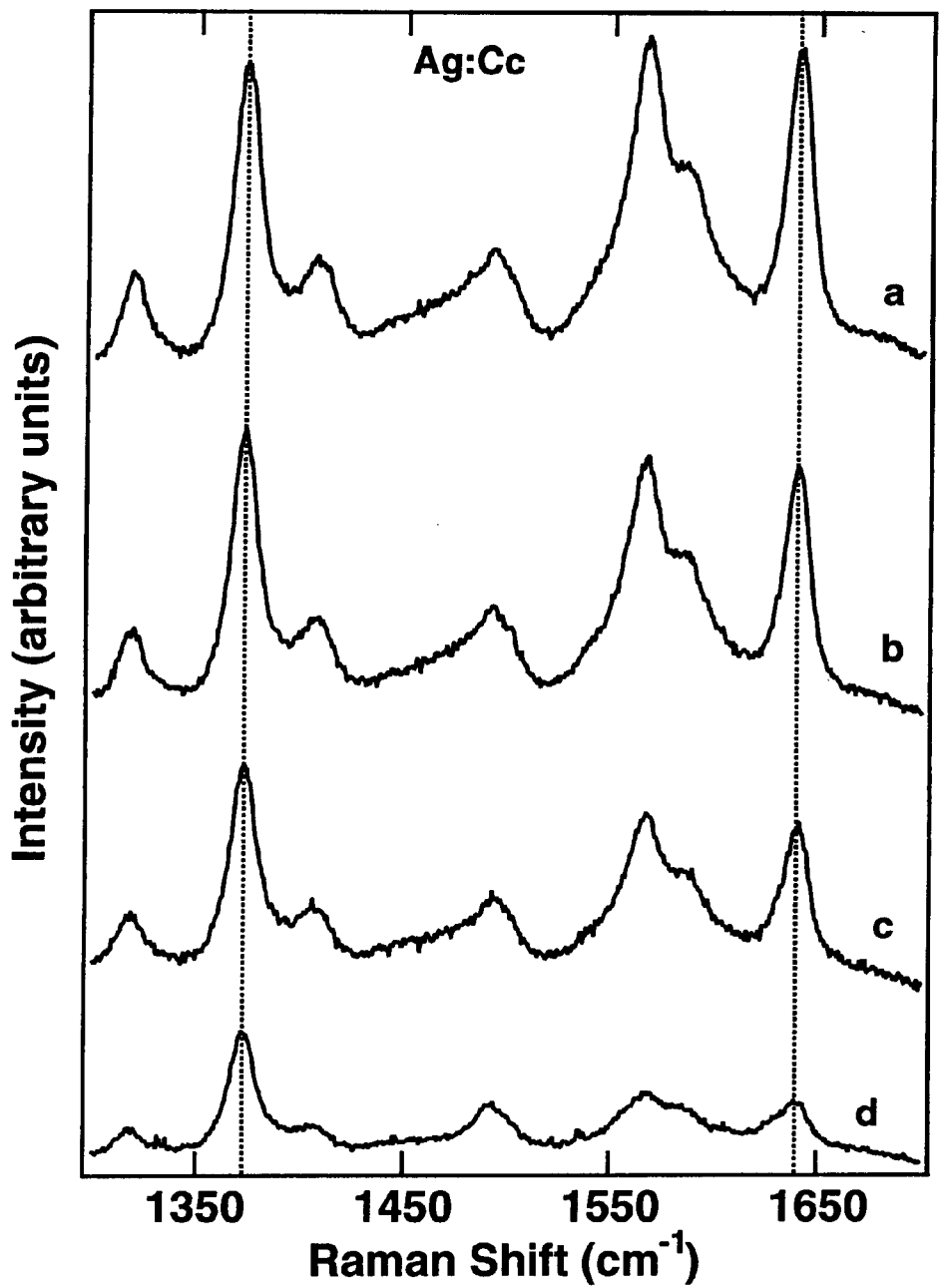
FIG. 10 shows SERS spectra for Ag:Cc for several (Cc): (a) $1.6 \times 10^{-7}$ M; (b) $8.3 \times 10^{-8}$ M; (c) $4.2 \times 10^{-8}$ M; (d) $1.6 \times 10^{-8}$ M.
Figure 11:
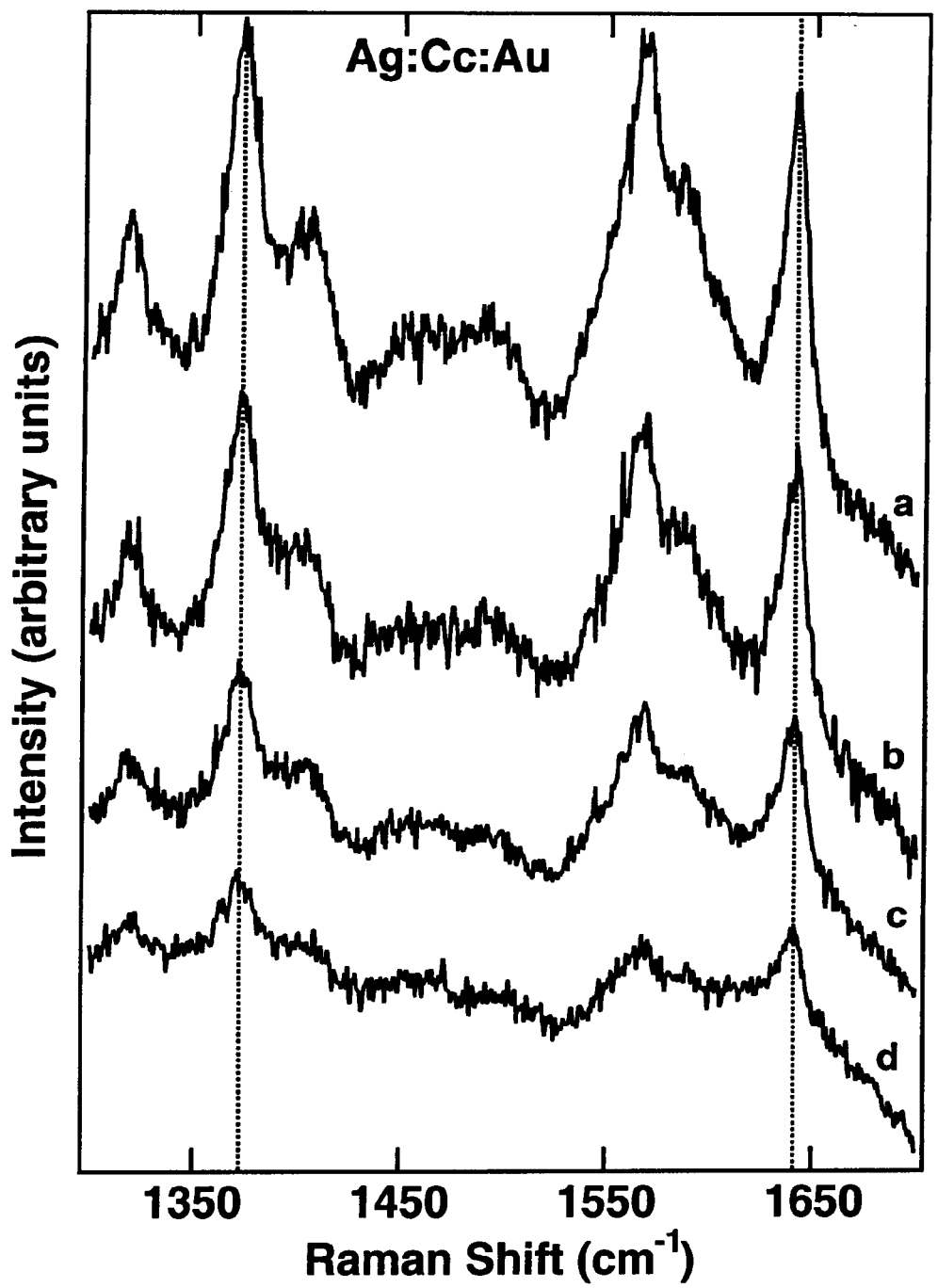
FIG. 11 shows SERS spectra for Ag:Cc:Au for several (Cc): (a) $8.3 \times 10^{-8}$ M; (b) $4.2 \times 10^{-8}$ M; (c) $2.1 \times 10^{-8}$ M; (d) $8.3 \times 10^{-9}$ M.
Figure 12:
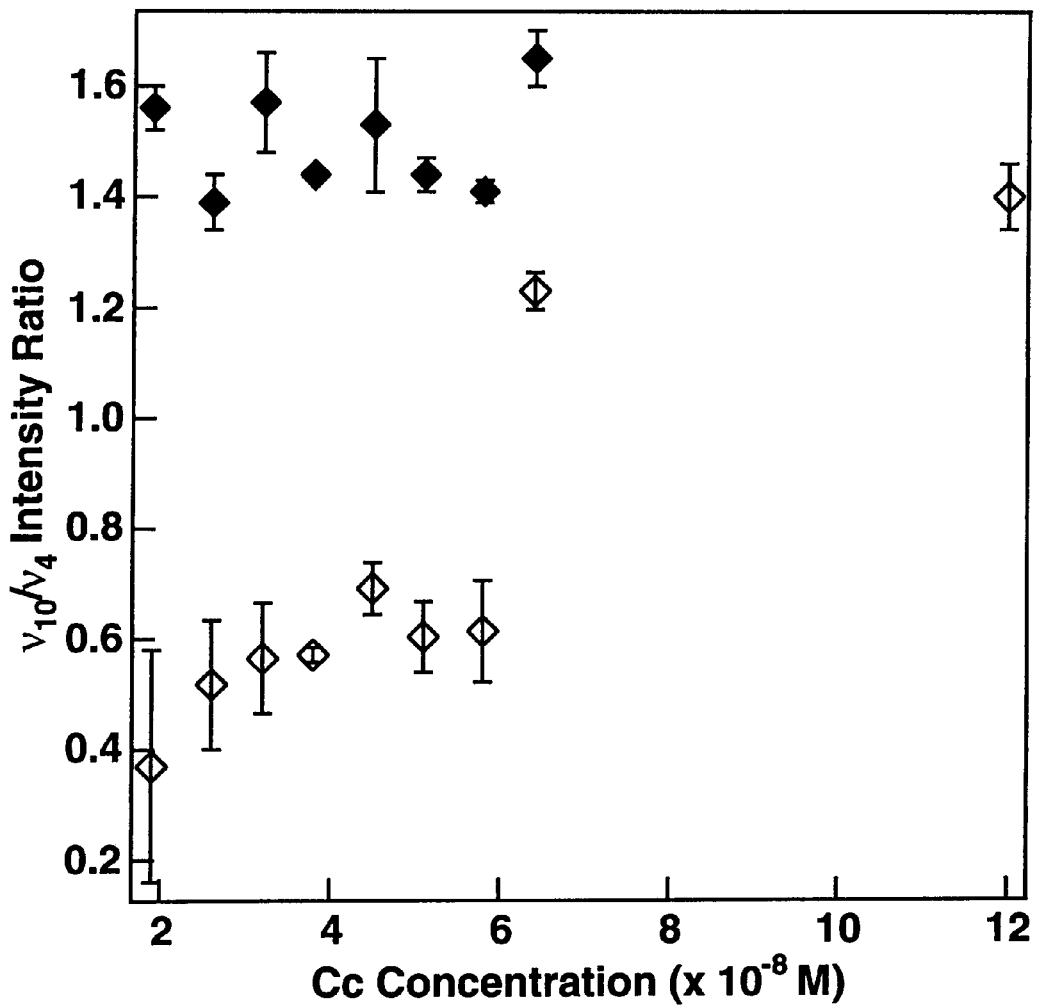
FIG. 12 shows average $v_{10}/v_4$ intensity ratio for Ag:Cc (open symbols) and Ag:Cc:Au (filled symbols), from several sets of data similar to that shown in FIGS. 10 and 11.

This is illustrated in FIG. 10, which shows SERS spectra with $\lambda_{ex}$=568 nm for Cc adsorbed to aggregated colloidal Ag at various (Cc). The $v_4$ (1375 cm$^{-1}$) and $v_{10}$ (1640 cm$^{-1}$) vibrations are indicated with dotted vertical lines. At the highest (Cc), $1.6\times10^{-7}$ M, the $v_4$ and $v_{10}$ vibrations are roughly equal in intensity. As the (Cc) decreases, the intensity of the $v_{10}$ band decreases relative to $v_4$. In contrast, now referring to FIG. 11, the relative intensities of $v_4$ and $v_{10}$ in Ag:Cc:Au remain constant as (Cc:Au) is decreased over the same range of (Cc). FIG. 12 shows the $v_{10}/v_4$ intensity ratio for Ag:Cc and Ag:Cc:Au as a function of (Cc). At high (Cc), there is sufficient Cc in the solution to completely coat the aggregated Ag surface, and this ratio is approximately equal for Ag:Cc and Ag:Cc:Au. As the (Cc) is decreased, however, the $v_{10}/v_4$ ratio for Ag:Cc ratio drops sharply, while the ratio for Ag:Cc:Au remains unchanged.

Previous workers have observed a change in the $v_{10}/v_4$ SERS intensity ratio in response to changes in (Cc) for Cc adsorbed to colloidal Ag aggregates (MacDonald, I. D. G.; Smith, W. E. *Langmuir* 1996, 12, 706–713). This result was interpreted in terms of changes in protein packing on the surface. At very low (Cc), the $v_{10}/v_4$ intensity ratio decreased, indicating that the angle between the heme plane and the surface normal had increased compared to its position at high packing densities, based on symmetry arguments as described above. The reason for Cc's conformational change with surface coverage was proposed to be due to favorable protein-protein interactions at high Cc densities. Illustrations A and C in FIG. 6 highlight the difference in Cc orientation on Ag at high and low coverage, respectively. In contrast, the Cc:Au conjugates used in Ag:Cc:Au samples are prepared under high Cc packing conditions, and the number of Cc per Au particle does not change upon dilution of the Cc:Au added to aggregated Ag sol. Thus, the Cc concentration on the colloidal Au is fixed, irrespective of the amount of Cc:Au added to aggregated Ag.

Figure 13:
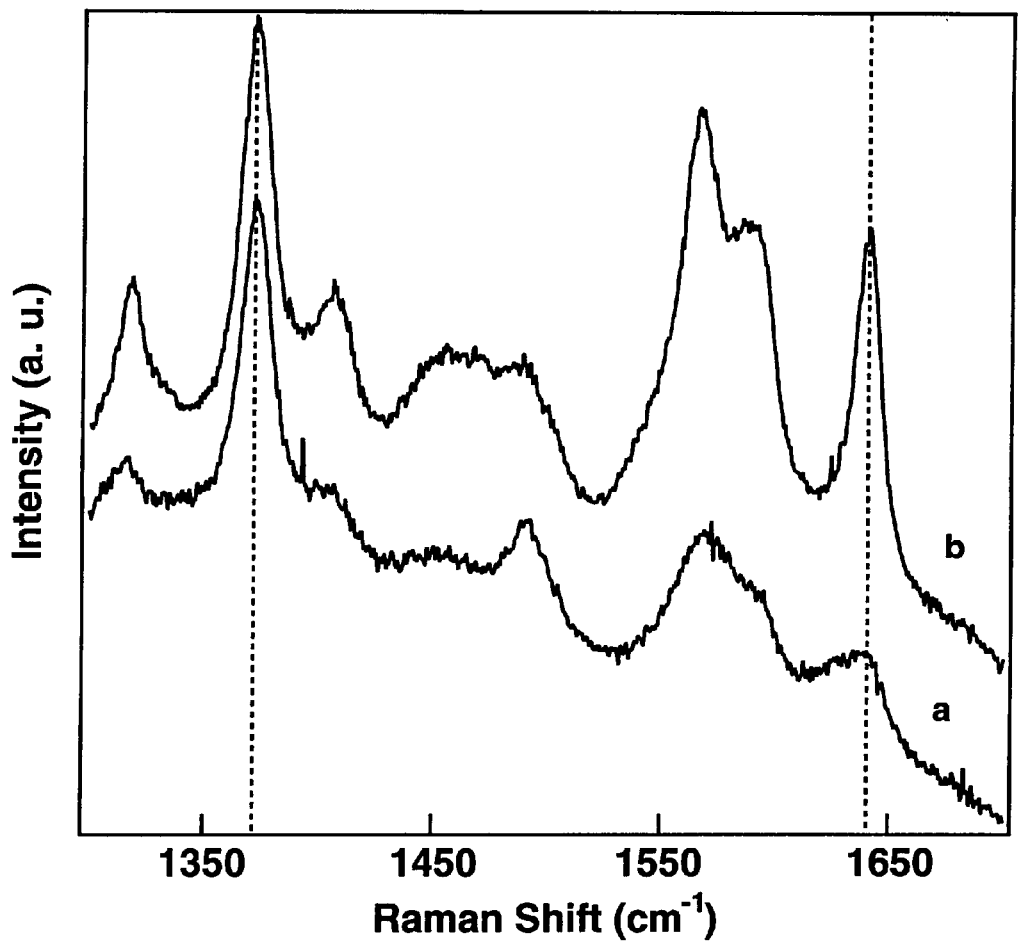
FIG. 13 shows SERS spectra at 568.2 nm excitation, for Cc:Ag/Au conjugates prepared under (a) high (Cc), and (b) low (Cc) conditions (0.2 monolayer coverage).

FIG. 13 compares SERS spectra at aggregated Ag for Cc:nanoparticle conjugates which were prepared at high and low (Cc). Spectrum (a) represents conjugate with a monolayer of Cc adsorbed to the surface, while spectrum (b) is for a conjugate prepared with only enough Cc for 0.2 monolayer coverage. As expected, there is a dramatic difference in $v_{10}/v_4$ ratio. Beyond this, the data are revealing in two respects. (i) When the low-coverage conjugates were prepared the Cc partially coated all of the Au particles, rather than fully coating only some; had full coating occurred, the $v_{10}/v_4$ ratio for (a) and (b) would be the same. (ii) The Cc conformation determined by the initial (Cc) present during conjugate formation was retained for low Cc coverages as well as high coverages. This is further evidence that Cc cannot desorb from metal nanoparticles after preparation of conjugates. The results of this experiment indicate that it is possible to use conjugates to control biomolecule orientation, by dictating their concentration during conjugate formation. Importantly, this technique can also be coupled with manipulation of the protein:Au binding chemistry through, for example, covalent modification of protein residues.

The folowing example indicates the enhanced stability relative to directly adsorbed protein of Cc in a metal-Cc-metal sandwich. Prior conjugation to colloidal Au prevents the evolution of non-native spin states in Cc under conditions sufficient to cause them in free Cc of the same concentration. Hildebrandt and Stockburger have observed that Cc adsorbed at SERS-active Ag electrodes existed in a mixed spin-state at room temperature, but could be reversibly converted to the native low-spin state by lowering the temperature to 196 K (Hildebrandt, P.; Stockburger, M. *J Phys. Chem.* 1986, 90, 6017–6024). Based on the reversibility of this conversion, they concluded that the protein had not denatured but had instead undergone a surface-induced, reversible conformational change at higher temperatures. Further experiments on Cc adsorbed at negatively-charged surfaces of Ag sols, Ag electrodes, tungstate salts, and phospholipid bilayers have indicated the presence of two populations of Cc at the interface. Although Cc itself is found in solution, its physiological role is to shuttle electrons between two membrane-bound proteins. Thus, Cc-surface interactions may be functionally significant. Hildebrandt and coworkers found evidence for the presence of two distinct conformations of Cc bound to surfaces, and refer to these as states I and II. In state I, the protein has not undergone significant structural changes at the surface, while in state II, SERS data show the onset of a mixed-spin state population and an "opening" of the heme pocket. Such gross surface-induced conformational changes were not observed here study, nor in the work of MacDonald and Smith (see above). A principle difference between these experiments and those of Hildebrandt appears to be not only the choice of substrate (the latter have used citrate-reduced Ag sols), but also the surface concentration of adsorbed Cc. Although the Cc coverage is difficult to know precisely at the ill-defined roughened Ag surfaces used for SERS experiments, Hildebrandt and Stockburger estimated by Frumkin isotherm a coverage of only ~0.2 monolayer at a roughened Ag electrode. Higher coverages of Cc were used in both here and the MacDonald/Smith studies (as evidenced by the greater $v_{10}/v_4$ ratio in the Cc SERS spectra at $\lambda_{ex}$=514.5 nm).

Figure 14:
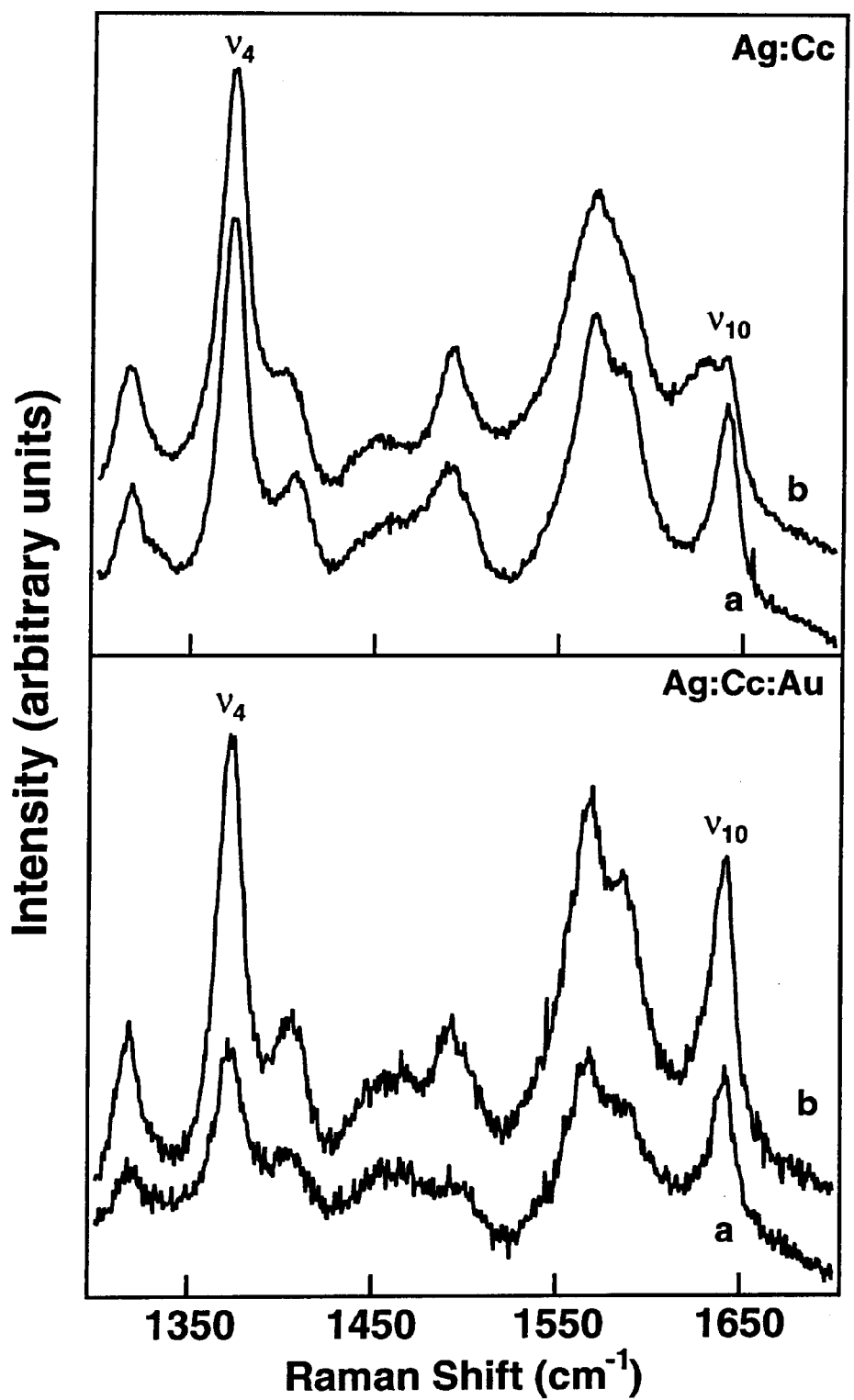
FIG. 14 shows stability of free Cc (top) vs. Cc:Au (bottom) on aggregated Ag sols toward spin state conversions, through spectra using 568 nm excitation taken at 0 min. (a) and 45 min. (b) after sample preparation.

Conversions from Cc's native low spin (LS) to high spin (HS) have been observed previously at citrate-reduced Ag sols for low (Cc) (see MacDonald and Smith). To assess the extent of conversion from low spin to high spin in conjugates, SERS spectra at 568.2 nm excitation for free Cc and Cc:Au adsorbed to aggregated Ag sols were acquired at various times after sample preparation, as shown in FIG. 14. The samples were exposed to the laser beam only during spectral acquisition. The (Cc) in the first set of samples was $1.7\times10^{-8}$ M, which is less-than-monolayer coverage on the aggregated Ag substrate. The free Cc sample begins to show some spectral changes (i.e. changes in the ratios of bands) after only 15 minutes, while the Cc:Au spectrum remains essentially unchanged, other than an overall increase in intensity, for more than 45 minutes. The increase in intensity over time is not related to errors in sample positioning, which is very reproducible. Rather, it results from slow, time-dependent changes in aggregation of colloidal Ag. This phenomenon, which occurs over~one-half hour, occurred for all compounds, irrespective of the presence or absence of colloidal Au. Accordingly, care was taken to run samples at identical times after aggregation in this experiment, and more generally, immediately after sample preparation. The spectral changes observed for Ag:Cc are due to a partial LS to HS conversion, as evidenced by the loss of intensity for the spin state marker band, $v_{10}$, at 1640 $cm^{-1}$, and the gain of intensity for this mode at ~1630 $cm^{-1}$. The enhanced stability of Cc conjugated to colloidal Au can be attributed to the restricted conformational flexibility of the close-packed Cc molecules of the Cc:Au as compared to the low coverage Cc adsorbed directly to colloidal Ag aggregates.

Figure 15:
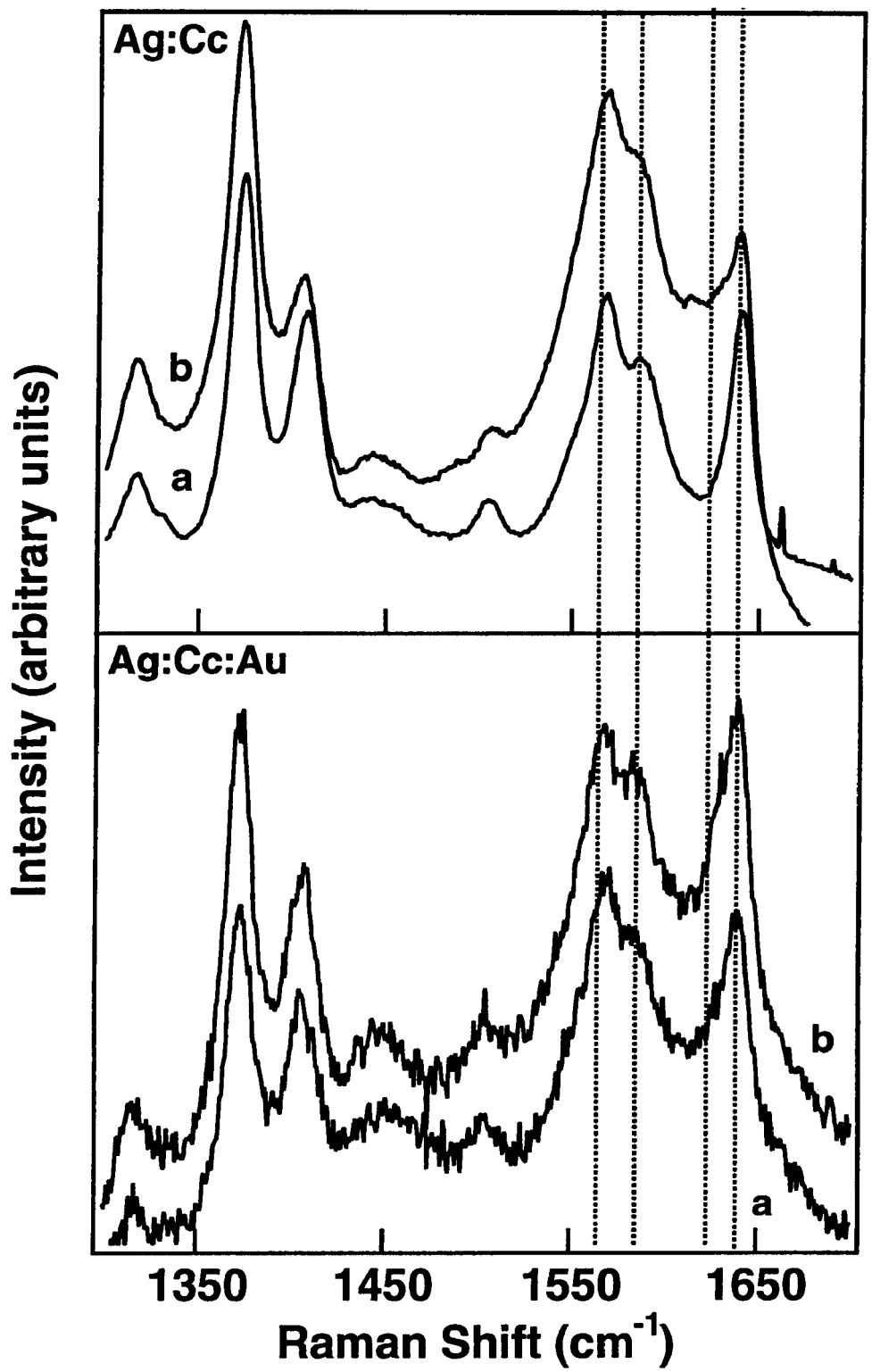
FIG. 15 shows stability of free Cc (top) vs. Cc:Au (bottom) on aggregated Ag sols toward spin state conversions, through specta using 514.5 nm excitation taken at 0 min. (a) and 120 min. (b) after preparation of SERS sample.

Ag:Cc:Au also exhibits increased stability relative to Ag:Cc at higher concentrations, as shown in FIG. 15, which depicts SERS spectra for Cc and Cc:Au at (Cc)=7.5×10$^{-8}$ M, acquired 120 minutes after sample preparation. The Cc:Au sample is essentially unchanged, while the Cc shows clear signs of conformational changes indicative of some high-spin Fe in the sample (see above). Thus, even at higher Cc coverages, prior conjugation to colloidal Au has increased the resistance of adsorbed Cc to conformational changes that can lead to denaturation. This could be due to the still somewhat denser packing of Cc in Ag:Cc:Au as compared to Ag:Cc, to the smaller radius of curvature of the 12-nm diameter Au spheres as compared to the Ag aggregates, or to a combination of these effects. Whatever the cause of this added stability, it illustrates a clear advantage to the use of Au conjugates for protein SERS.

Figure 16:
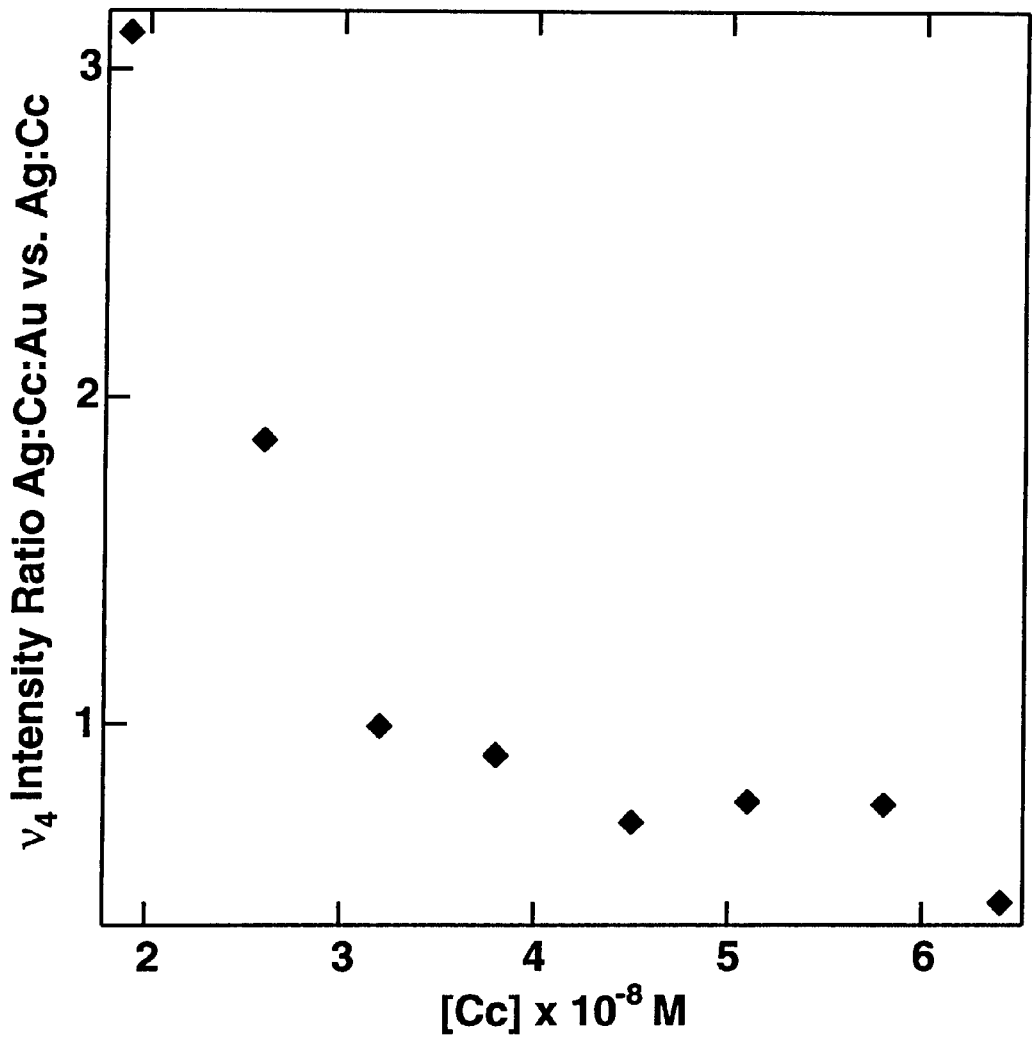
FIG. 16 shows $v_4$ SERS intensity ratio at 568.2 nm excitation for Ag:Cc:Au/Ag versus Ag:Cc as a function of (Cc).

The following example illustrates the benefits of this invention for acquisition of spectra at low analyte concentrations, because the conjugates display a reduced rate of protein loss due to adsorption to container walls. FIG. 16 is a plot of the $v_4$ SERS intensity ratio for Ag:Cc:Au versus Ag:Cc as a function of (Cc). It was observed during these studies that dilute Cc solutions stored for several hours in either glass vials or plastic microcentrifuge tubes lost a substantial amount of Cc from solution over time. Presumably the missing Cc had bound to the vessel walls. For Cc:Au at similar concentrations, no change in concentration was observed over the same time periods. Accordingly, the ratio increased at low concentrations, with Ag:Cc:Au yielding more intense spectra than Ag:Cc as the overall (Cc) fell below 30 nM. This phenomenon could be due to the much slower diffusion for Cc-clad Au nanoparticles, or to blocking of adsorption sites on the Cc by the Au (e.g. if the free Cc bound to the vessel walls through the lysine patch, which was already bound to Au in the conjugates).

Figure 17A:
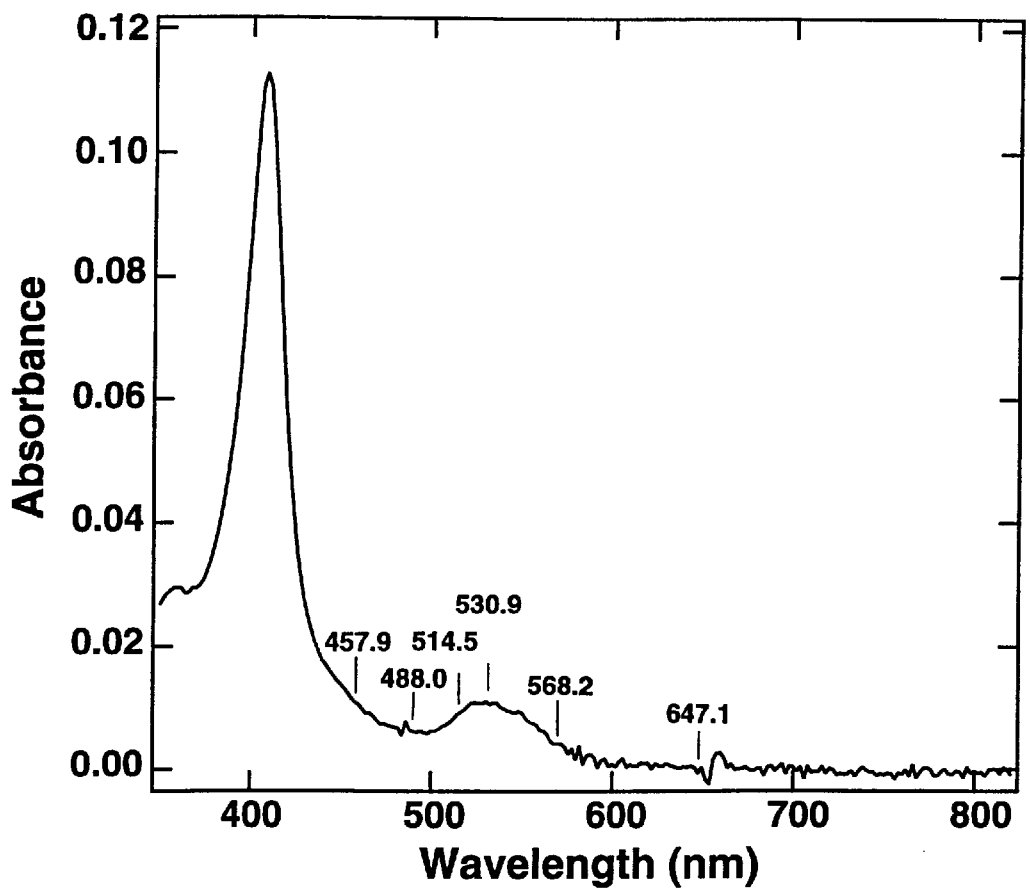
FIG. 17A shows an optical spectrum for horse heart ferricytochrome c, illustrating the wavelengths of several of the laser lines used for excitation of Raman scattering.
Figure 17B:
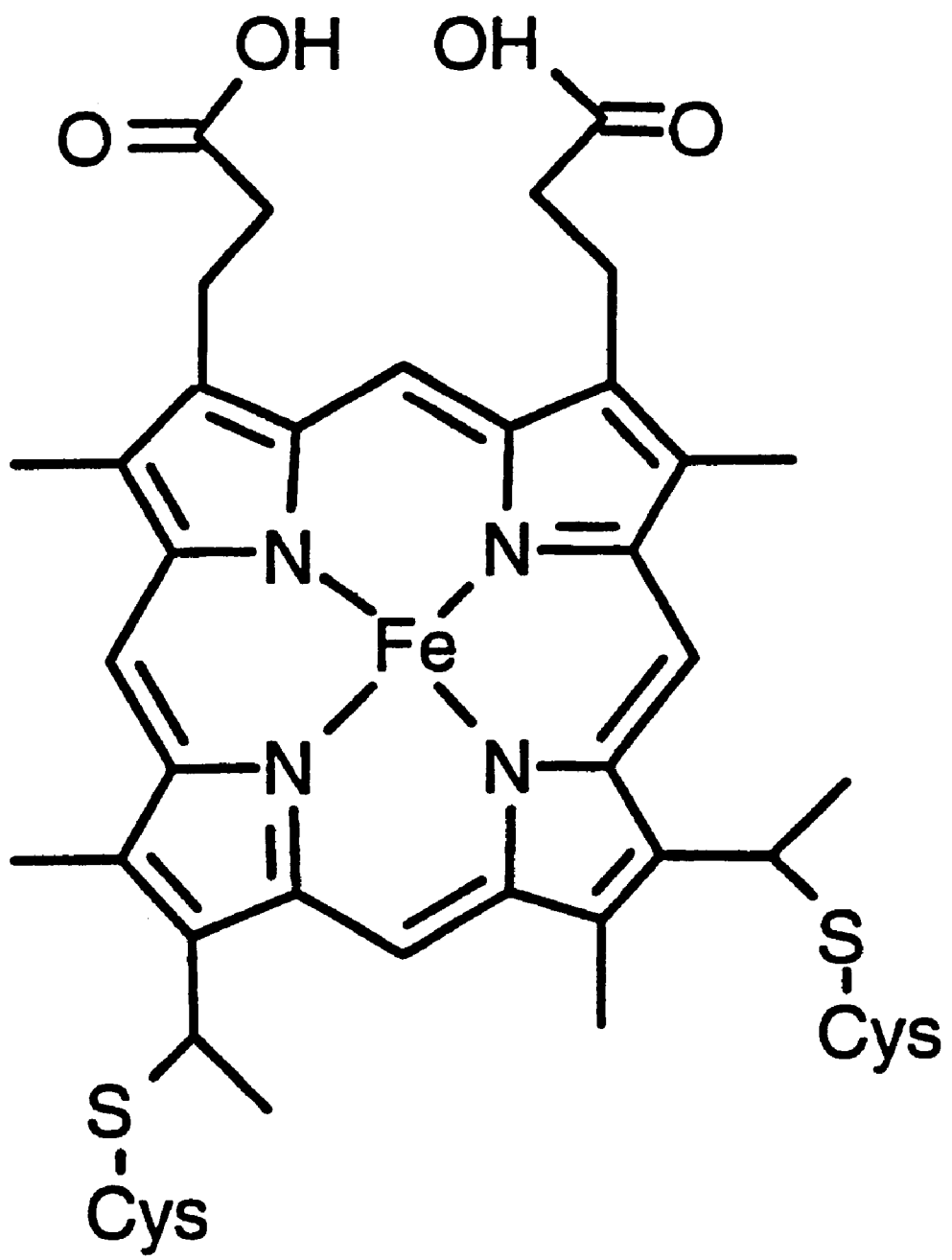
FIG. 17B illustrates the chemical structure of the heme group of Cc.

The following example illustrates how sample geometry of invention is beneficial with regard to the electromagnetic enhancement. Specifically, the example shows how both the Au nanoparticle and aggregated Ag sol play an important role in the observed SERS spectra. An optical spectrum for horse heart ferricytochrome c is shown in FIG. 17A Several wavelengths corresponding to SERS excitation wavelengths used in this example are indicated on the spectrum. When $\lambda_{ex}$ coincides with an electronic transition (see FIG. 17B for the chemical structure of the heme chromophore), resonant enhancement of the Raman scattering can occur. Some of the excitations used in this example are in the region of the Q-bands (~500–580 nm), while others do not coincide with any electronic transitions of the heme chromophore.

Figure 18:
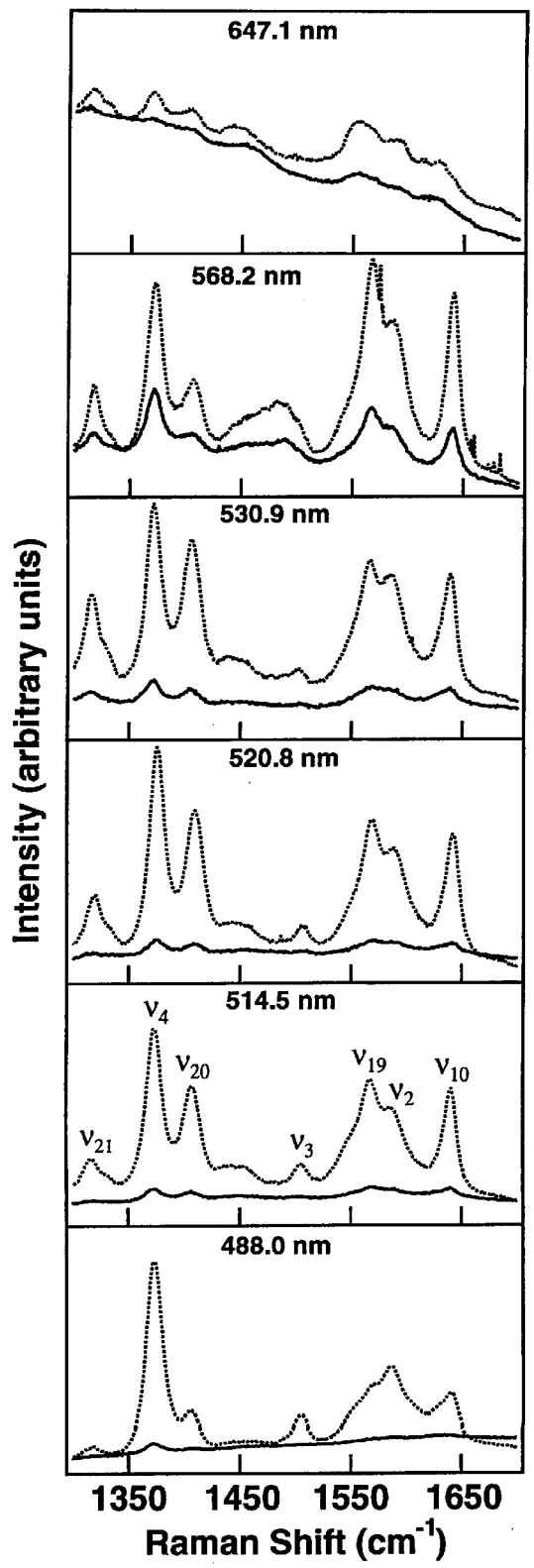
FIG. 18 shows SERS spectra at aggregated Ag sol for cytochrome c (dotted line, ... ) and cytochrome c:Au colloid conjugates (solid line, —) at several excitation wavelengths. Note that the markings in parentheses refer to the representations of the data curves.

FIG. 18 compares SERS spectra obtained for each of the geometries A and B in FIG. 6 at several excitation wavelengths. The upper spectrum in each panel is that for Cc adsorbed directly to the Ag surface (A, dotted lines), while the lower spectrum corresponds to adsorbed Cc:Au conjugates (B, solid lines). In these experiments, not only are cytochrome c concentrations, sample volumes, excitation wavelengths, light collection geometries and efficiencies, and integration times identical for A and B in each panel, but so are any effects due to resonance enhancement of Cc's heme, or to the wavelength-dependence of SERS from Ag aggregates. Thus, comparison of spectra for A and B for each set of conditions allows effects not due to geometry to be factored out.

The spectra shown in FIG. 18 are due to vibrations of the heme moiety of Cc and agree well with previous resonant-SERS studies of Cc on Ag sols at high Cc coverage. Band assignments are given in Table I. The position of the oxidation state marker band ($v_4$) at ~1375 $cm^{-1}$ indicates that the Cc exists in the $Fe^{3+}$ state, which was expected since the Cc used in these studies was ferri-Cc prior to adsorption to Ag. In addition, the location of the spin state marker band ($v_{10}$) at ~1635 $cm^{-1}$ indicates that the Cc Fe is low-spin, meaning that it has not undergone ligand loss, transforming to the high-spin state (a sign of denaturation or other conformational change due to surface adsorption). The data shown here are similar to those reported by MacDonald and Smith (see above) for Cc SERS at aggregated Ag sols ($\lambda_{ex}$=514.5 nm), and do not show signs of the surface-induced conformational changes. In summary, the Cc giving rise to the observed SERS signals is in its native conformation.

While the critical comparisons are between spectra for Ag:Cc and Ag:Cc:Au (i.e. A and B), it is useful to begin discussion of the SERS wavelength dependence by looking at each component separately. For the Cc directly adsorbed at Ag (A, dotted lines), significant differences in relative peak intensities for SERS spectra excited at different wavelengths are observed. These differences in relative intensities cannot be explained in terms of protein concentration (all samples were identically prepared); however, they are similar to ratios previously observed in Cc solution resonance Raman (RR) excitation profiles and SERS enhancement profiles for free Fe(III) protoporphyrin at Ag electrodes. Excitation at 514.5 and 568.2 nm gives rise to intense signal due to resonant SERS, while excitation at 488.0 or 647.1 nm, which do not coincide with electronic transitions of the heme, required much higher laser powers and led to a weaker signal attributable to nonresonant SERS.

Inspection of FIG. 18 also reveals differences in the relative intensities of the various bands for the different $\lambda_{ex}$. For example, at 488.0 nm excitation, the $v_4$ vibration dominates the spectrum, while at $\lambda_{ex}$=568.2 nm, $v_4$, $v_2$, and $v_{10}$ have roughly equal intensities. In resonance Raman experiments, modes with $A_{1g}$ symmetry ($v_4$, $v_3$) are known to be preferentially enhanced by excitation into the Soret band (Franck-Condon, or A-term scattering mechanism), while excitation into the Q bands (vibronic, or B-term scattering) favors the non-totally symmetric modes ($B_{1g}$, $A_{2g}$, $B_{2g}$), resulting in greater signal from $v_{10}$, $v_{19}$, and $v_2$ vibrations. For the Cc SERS data in FIG. 18, excitation at 488.0 nm—although not resonant with the Soret band—results in greater enhancement of $v_4$, while excitation into the Q bands leads to a relative increase in signal from the other bands. At 647.1 nm excitation, $v_4$ is much diminished compared to the other bands. Thus it appears that even for pre-resonance, excitation wavelengths closer to the Soret band (488.0 nm) favors A-term scattering, while excitations further to the red favor B-term scattering.

A key difference between A (Ag:Cc) and B (Ag:Cc:Au) (see FIG. 6) involves the distance between the heme chromophore and the SERS substrate: the heme groups are oriented away from the Ag particle in B and toward it in A. This is because the lysine-rich heme pocket of Cc is attracted to the negatively-charged metal particles; it is expected to bind with the heme closest to the first type of metal nanoparticle it encounters. Thus, the heme will be oriented close to the Ag surface when Cc is added directly to Ag sols; indeed, this is why it has proven simple to obtain SERS spectra of Cc adsorbed to Ag. However, the heme will be oriented towards the Au surface for Ag:Cc:Au samples. As a result, the distance between the SERS-active Ag particle aggregate and the heme moiety is significantly greater for Ag:Cc:Au (B) than for Ag:Cc (A).

Based on the much greater distance between the heme and the Ag surface in the Ag:Cc:Au samples, a substantial decrease in signal in the Ag:Cc:Au samples (B) vs. the Ag:Cc samples (A) is expected. To a first approximation, SERS EM enhancement is predicted to go as $(r/r+x)^{12}$, where r is the radius of curvature of the surface feature on the enhancing surface and x is the distance from the surface to the analyte. The aggregated colloidal Ag surface is highly irregular, making estimates of r difficult; we will use the average radius of a single Ag particle (r=150 Å) as a rough approximation. The Cc is ~34 Å in diameter, with the heme group located close to one side. If we assume the heme group is located 3 Å from the surface and is 12 Å across, then x (the distance to the edge of the heme group)=either 3 Å (geometry A) or 19 Å (geometry B). Substituting into the distance dependence equation gives a factor of 3.4 difference in expected enhancement factor between the two orientations. For Ag:Cc:Au (B), this calculated distance effect is valid for only those Cc molecules located directly between the Ag surface and the Au particle; in fact, most of the Cc molecules are located significantly farther from the Ag surface. Enhancement factors for the Cc on the far side of the Au nanoparticle (x=150+34+120+3 Å) is expected to be three orders of magnitude lower than for the Cc in geometry A, assuming no contribution from the Au particle. Furthermore, the selection rules for SERS dictate that the efficiency of scattering will be affected by the angle between the heme and the surface, meaning that not all Cc molecules around the Au particle will be equally enhanced. Thus, one might not expect to observe Ag:Cc:Au SERS at all, based on distance arguments.

The lower spectra in each panel of FIG. 18 are SERS for Cc:Au conjugates adsorbed to aggregated Ag sols (B). Ag:Cc:Au spectra are weak as compared to Ag:Cc at the same (Cc) and acquisition parameters, but nevertheless observable. The wavelength dependence for Cc:Au on aggregated Ag might be expected to mirror that observed for Cc on Ag; optimum signal would be predicted from 514–568 nm, where benefit from resonant excitation of the heme chromophore could be realized. However, the SERS data show optimum scattering from Cc:Au at 568.2 nm excitation; at this wavelength, the signal for Cc:Au approaches that for Cc. Excitation at shorter wavelengths (e.g. 514.5 nm) leads to much poorer signal for Cc:Au, despite good SERS for directly adsorbed Cc at these wavelengths. The anomalously high SERS intensity observed with 568.2 nm excitation cannot result from the wavelength-dependence of SERS at Ag aggregates (since this is unchanged between A and B). Likewise, all other variables except for the particle-molecule geometry are the same between Ag:Cc:Au and Ag:Cc samples.

Figure 19:
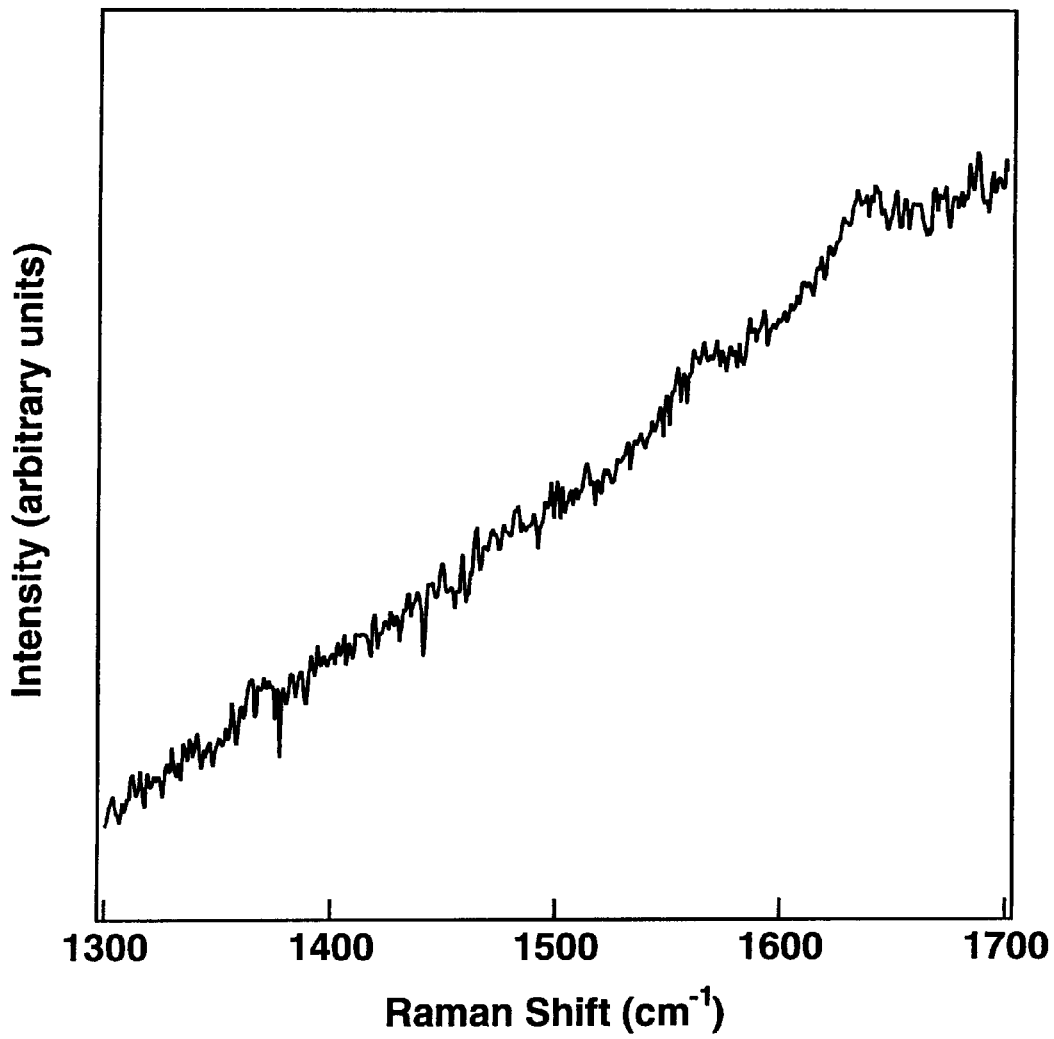
FIG. 19 shows a Raman spectrum for concentrated Cc:Au conjugates.

Both the apparent relaxation of the SERS distance dependence at 568.2 nm and the difference in B vs. A excitation profiles can be explained by the optical properties of Au nanoparticles: 568.2 nm is, and 514.5 nm is not, a wavelength at which heme molecular vibrations and Au surface plasmon polaritons can be resonantly excited simultaneously. That large SERS enhancements are observed under this condition indicates that the Au nanoparticles are taking part in enhancement of Raman scattering from Cc heme vibrations (further evidence will be described in other examples below). At shorter wavelengths, the damping of the Au plasmon diminishes this effect substantially, leaving the (distant) aggregated Ag substrate as the sole source of enhancement for the heme. Note that the optical properties of the Au nanoparticles alone cannot explain the magnitude of the observed scattering. A Raman spectrum of Cc:Au alone in solution shows negligible signal, even at a 10-fold greater concentration of Cc:Au conjugate and with 8-fold longer integration time (FIG. 19). Clearly, both the Au and Ag surfaces play important roles in the observed SERS spectra.

Figure 20:
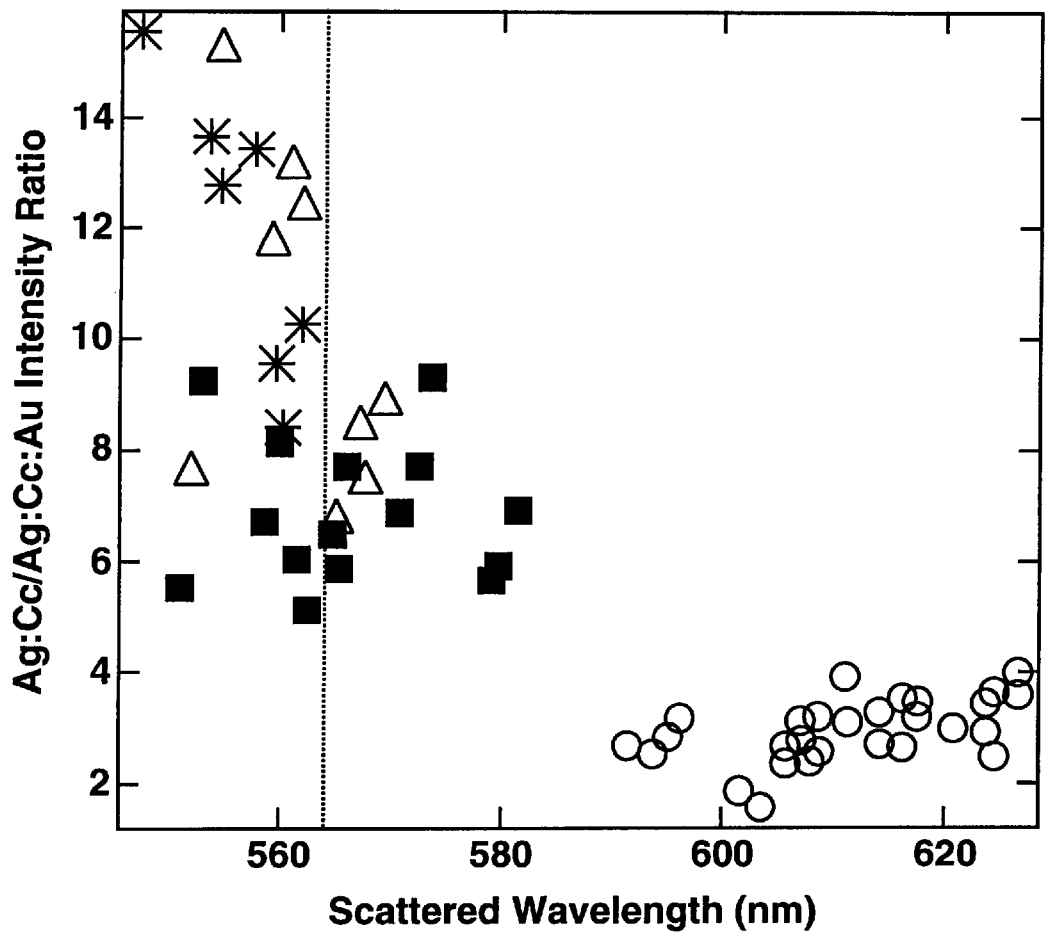
FIG. 20 shows Ag:Cc to Ag:Cc:Au intensity ratio for $v_4$ as a function of the wavelength of scattered light from each of several vibrational modes at excitation wavelengths of 514.5 (*), 520.8 nm, (□); 530.9 nm, (■), and 568.2 nm, (○).
Figure 21:
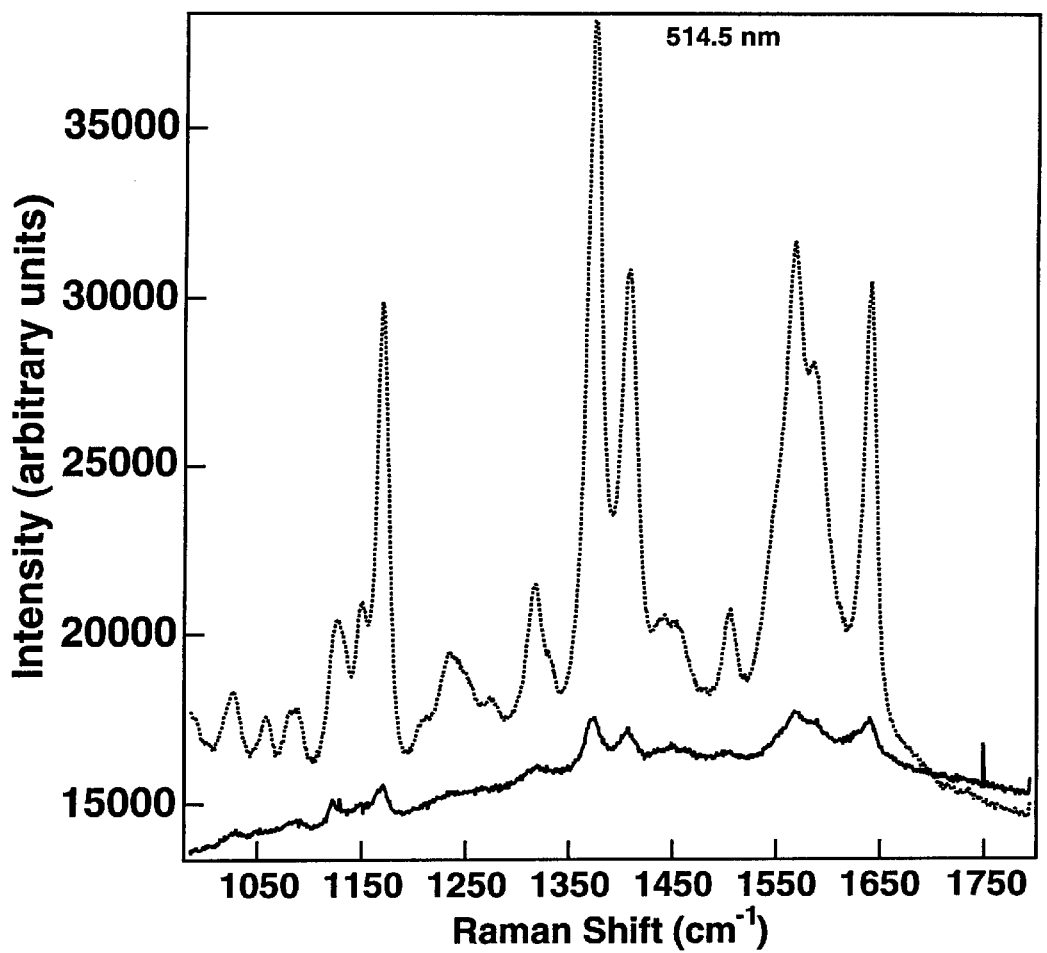
FIG. 21 shows SERS spectra on aggregated Ag sols for Cc and Cc:Au at 514.5 nm excitation.
Figure 22:
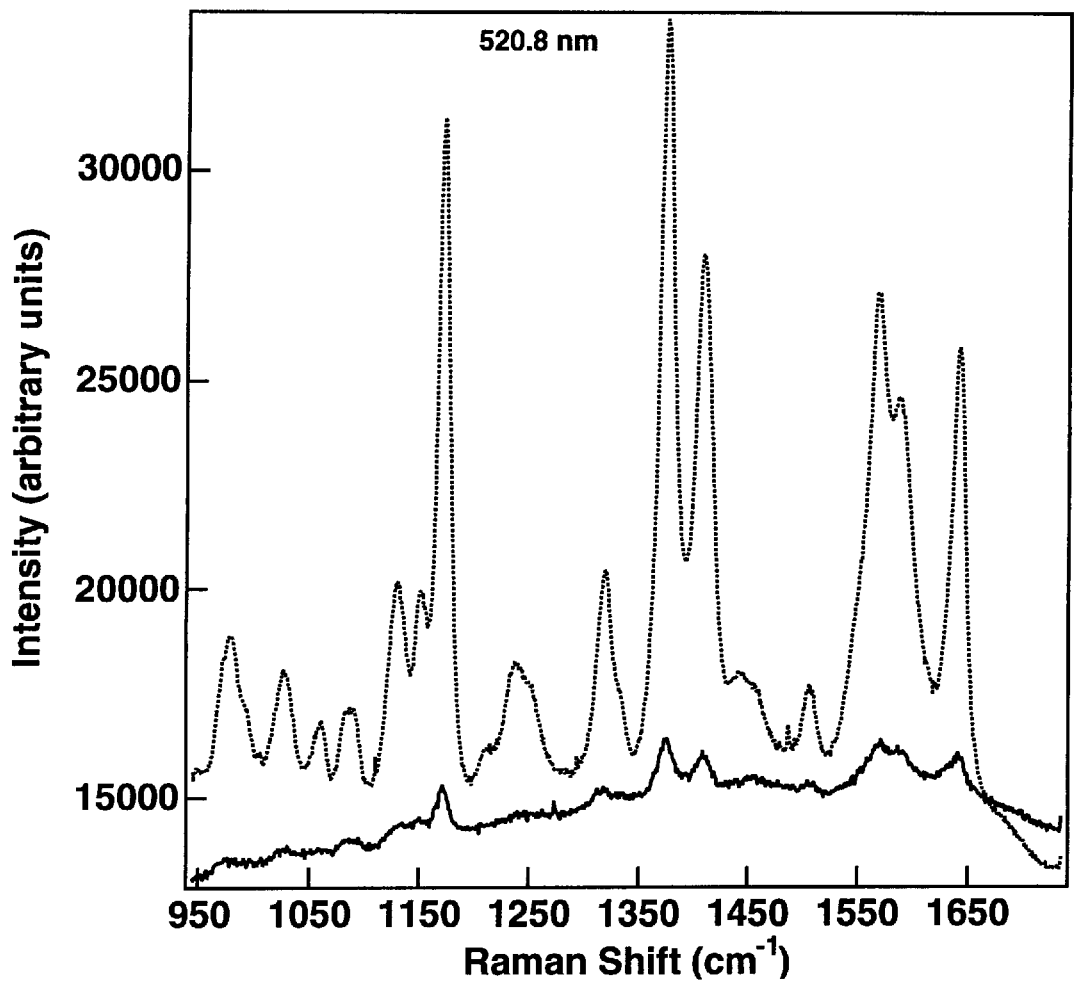
FIG. 22 shows SERS at aggregated Ag sols for Cc and Cc:Au, with 520.8 nm excitation.
Figure 23:
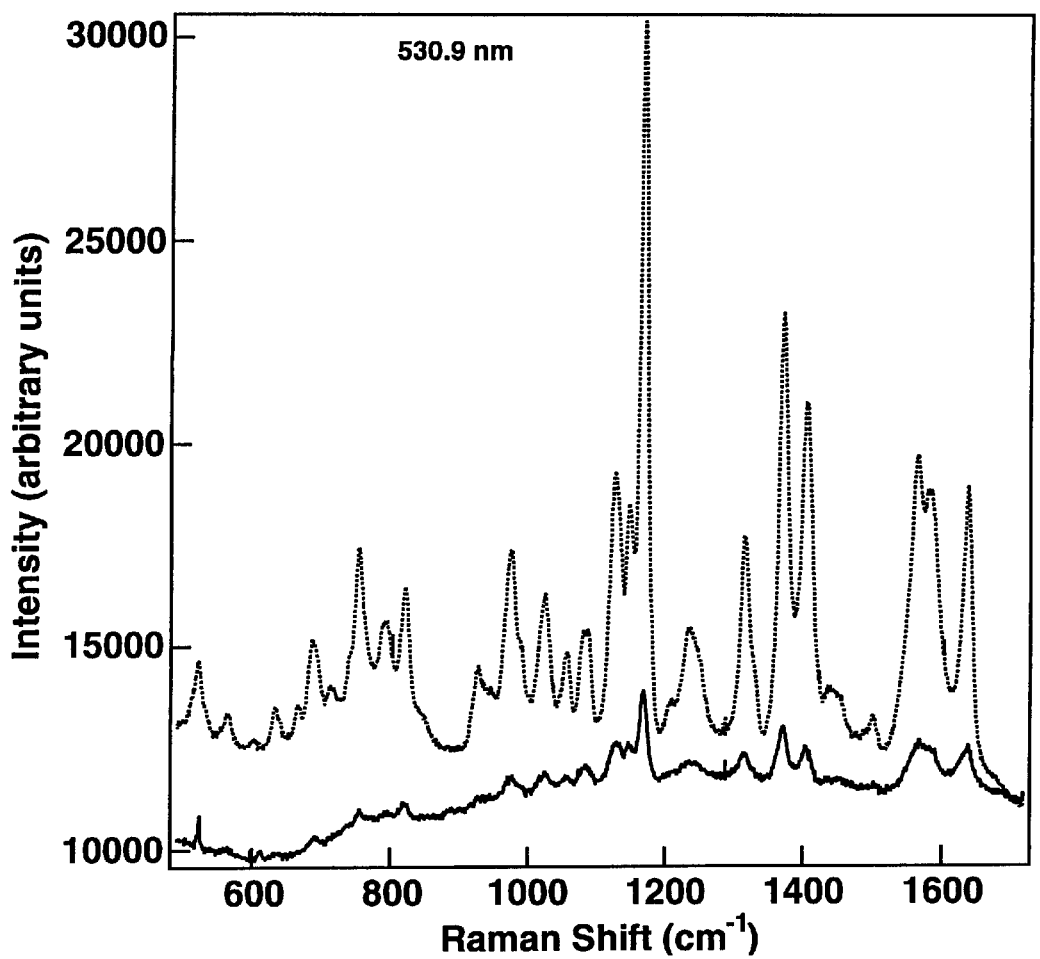
FIG. 23 shows SERS at aggregated Ag sols for Cc and Cc:Au, with 530.9 nm excitation.
Figure 24:
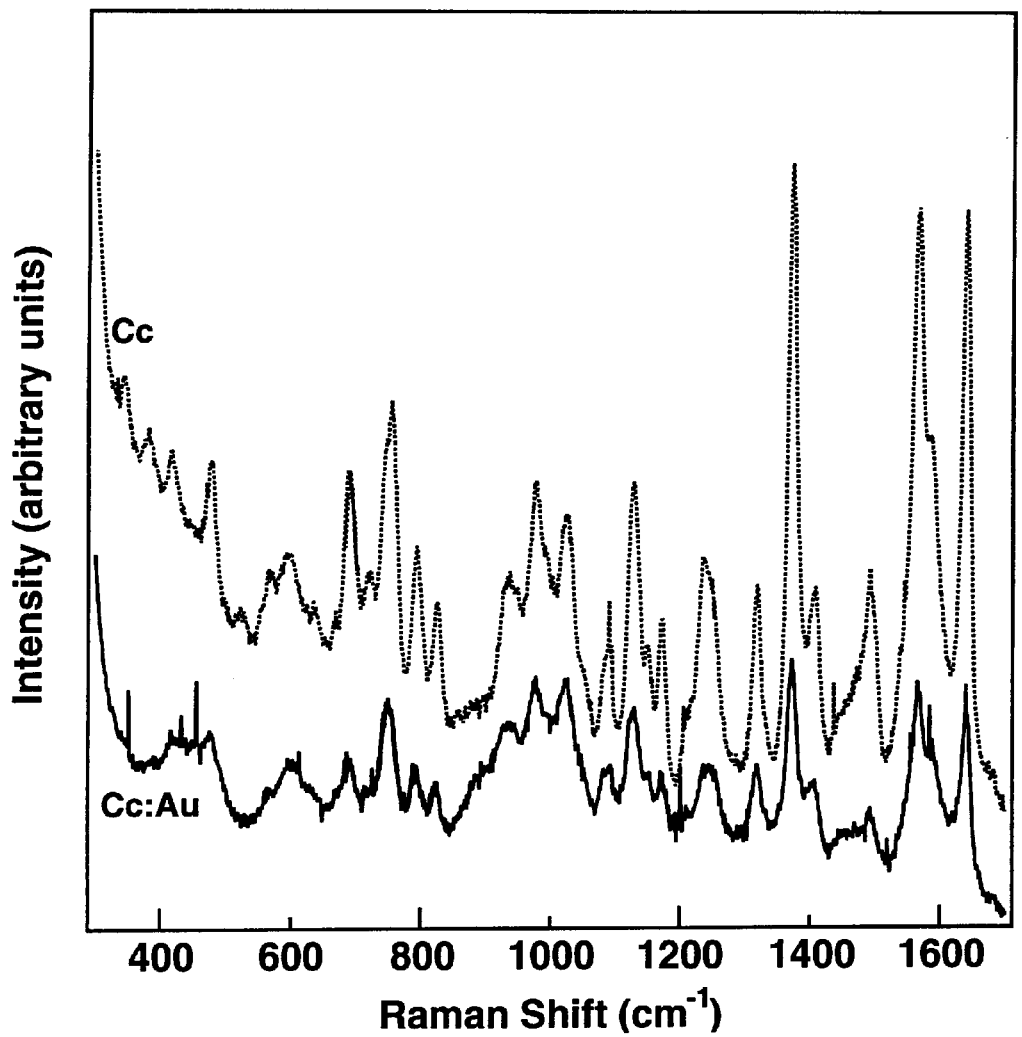
FIG. 24 shows SERS at aggregated Ag sols for Cc and Cc:Au, with 568.2 nm excitation.

The following example describes another line of evidence illustrating the benefit of the structure delineated by this invention. One reason that SERS enhancements are in general so large is that heightened electric fields at SERS-active substrates act on both incoming and scattered photons. However, since the scattered light is shifted from the incident frequency by the amount of the vibrational frequency, the incident and scattered radiation may not be equally surface enhanced. The large number of strong vibrational modes present in Cc SERS spectra make it possible to compare the relative SERS enhancements for Cc:Au and Cc at aggregated Ag sols over a range of scattered wavelengths ($\lambda_s$). SERS spectra for Cc and Cc:Au at aggregated Ag for $\lambda_{ex}$=514.5, 520.8, 530.9, and 568.2 nm were used to make a plot of Ag:Cc to Ag:Cc:Au intensity ratio vs. $\lambda_s$, shown in FIG. 20 (full spectra are shown in FIG. 21, FIG. 22, FIG. 23, and FIG. 24). Use of such a ratio factors out any differences between samples due to Cc concentration, laser power, collection optics, resonant enhancement of the heme moiety, wavelength-dependent SERS from the Ag aggregates (all of which should be the same for Cc and Cc:Au samples), or any other effects constant between samples. In FIG. 20, each $\lambda_{ex}$ is represented by a separate symbol. Exhibiting the lowest ratios, 568.2 nm (circles) is the optimal $\lambda_{ex}$ for all vibrational modes of Cc:Au (relative to Cc). There does not appear to be much variation in the intensity ratio for different vibrations at this $\lambda_{ex}$, despite an ~40 nm wavelength range for the vibrational modes. For $\lambda_{ex}$=530.9 (squares), 520.8 nm (triangles), and 514.5 nm (asterisks), there is more scatter in the data, due to poorer signal for Ag:Cc:Au. However, several trends are evident. First, while the scattering excited by excitation at 568.2 and 530.9 nm is insensitive to scattering wavelength ($\lambda_s$), that excited at 520.8 or 514.5 nm appears to be strongly dependent on $\lambda_s$. These data show that, for 568.2 and 530.9 nm excitation, there is little difference between incident and scattered light from the standpoint of enhancement, while at 520.8 and 514.5 nm excitations, there is so little enhancement of the incident light that any slight increases due to redshifting (for the scattered light) are observable. clearly a wavelength dependence to $\lambda_{ex}$ (and possibly to $\lambda_s$ for short $\lambda_{ex}$). These data comprise further evidence that the wavelength-dependent optical properties of the Au nanoparticles (to which Cc is bound) are impacting the outcome of SERS experiments.

Figure 25:
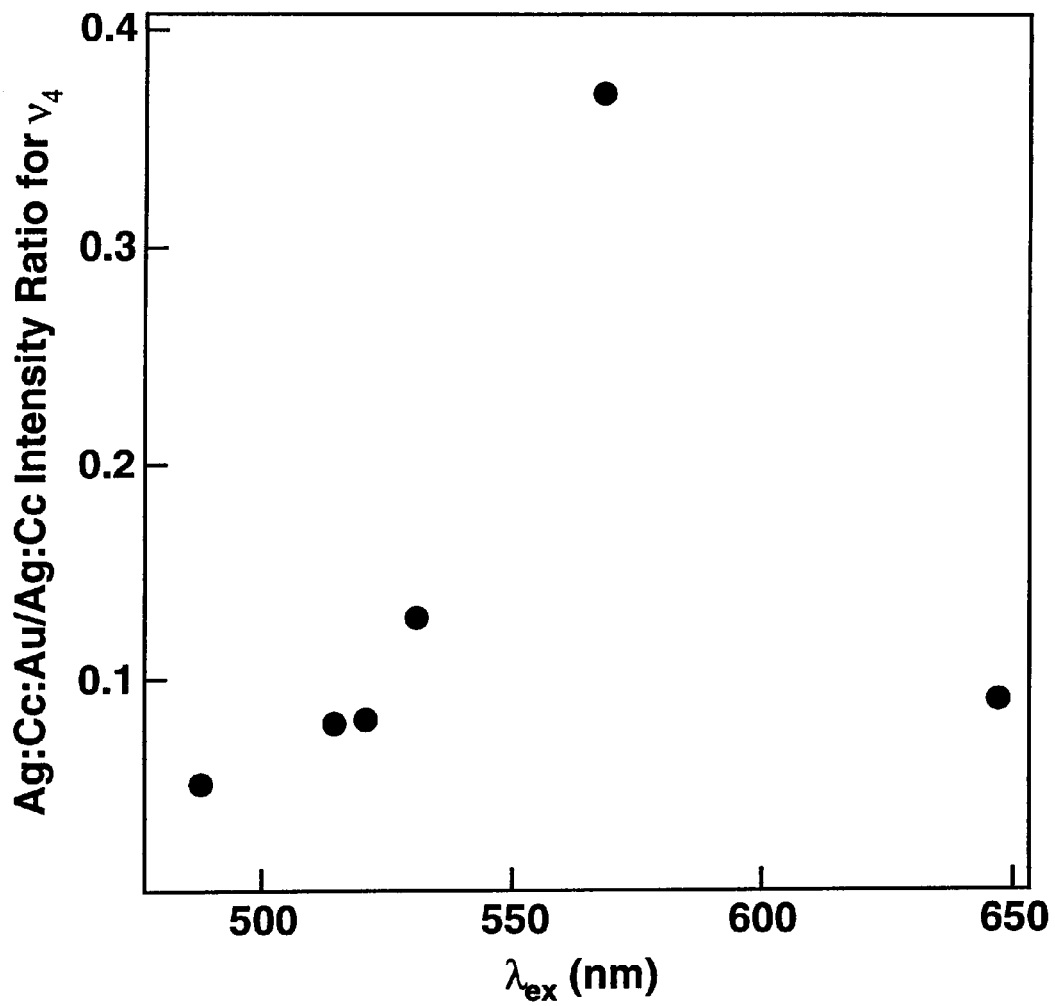
FIG. 25 shows the intensity ratio for the $v_4$ band versus excitation wavelength for Ag:Cc to Ag:Cc:Au.

The next example proves the existence of strong electromagnetic coupling, leading to higher effective electromagnetic fileds, between the colloidal Au nanoparticle and the aggregated Ag substrate. Cc vibrational modes are highly sensitive to many factors, including the conformational state of the protein. Small changes in the average geometry of adsorption of Cc to colloidal Ag can lead to measurable changes in relative peak intensities. To avoid any complication in Ag:Cc:Au vs. Ag:Cc intensity ratio data due to slight differences in Cc orientation for the two geometries, the ratios were plotted vs. $\lambda_{ex}$ for a single vibrational mode ($v_4$) (FIG. 25). The $v_4$ band was chosen because it is relatively insensitive to changes in protein conformation. The data comprise a plot of the Ag:Cc:Au to Ag:Cc (i.e. B/A) intensity ratio for the $v_4$ band versus excitation wavelength (note the inversion of this ratio as compared to the A/B ratio shown in FIG. 20; for the remainder of this document B/A ratios will be used, such that larger ratios correspond to larger relative signal for the sandwich geometry, B). This ratio is less than 1 at all $\lambda_{ex}$, reflecting the weak relative signal of Ag:Cc:Au as compared to Ag:Cc. This of course reflects differences between A and B with regard to the geometric relationship between the protein and the metal particles. In A, while every molecule of Cc is in close proximity to the aggregated Ag, in B most Cc molecules are not close to the Ag surface, and some are separated by more than 12 nm, the diameter of the Au particle. Nonetheless, changes in the ratio are observed with $\lambda_{ex}$, indicating that the SERS enhancement profiles for the two samples are not the same. The B/A intensity ratio increases monotonically from 488.0 to 568.2 nm, as the signal from Cc:Au increases relative to that of Cc alone. This mirrors the trend shown in FIG. 20, and can be explained by the diminishing effects of plasmon damping for Au as wavelength increases. The B/A ratio decreases again a $\lambda_{ex}$ lengthens to 647.1 nm. This excitation wavelength is not in resonance with the heme, but this is the case for both samples. Since the Au surface plasmon is less damped at 647.1 nm than at 568.2 nm, one might have expected a larger value for this ratio; the falloff can be understood upon consideration of the optical properties of these SERS samples.

Figure 26:
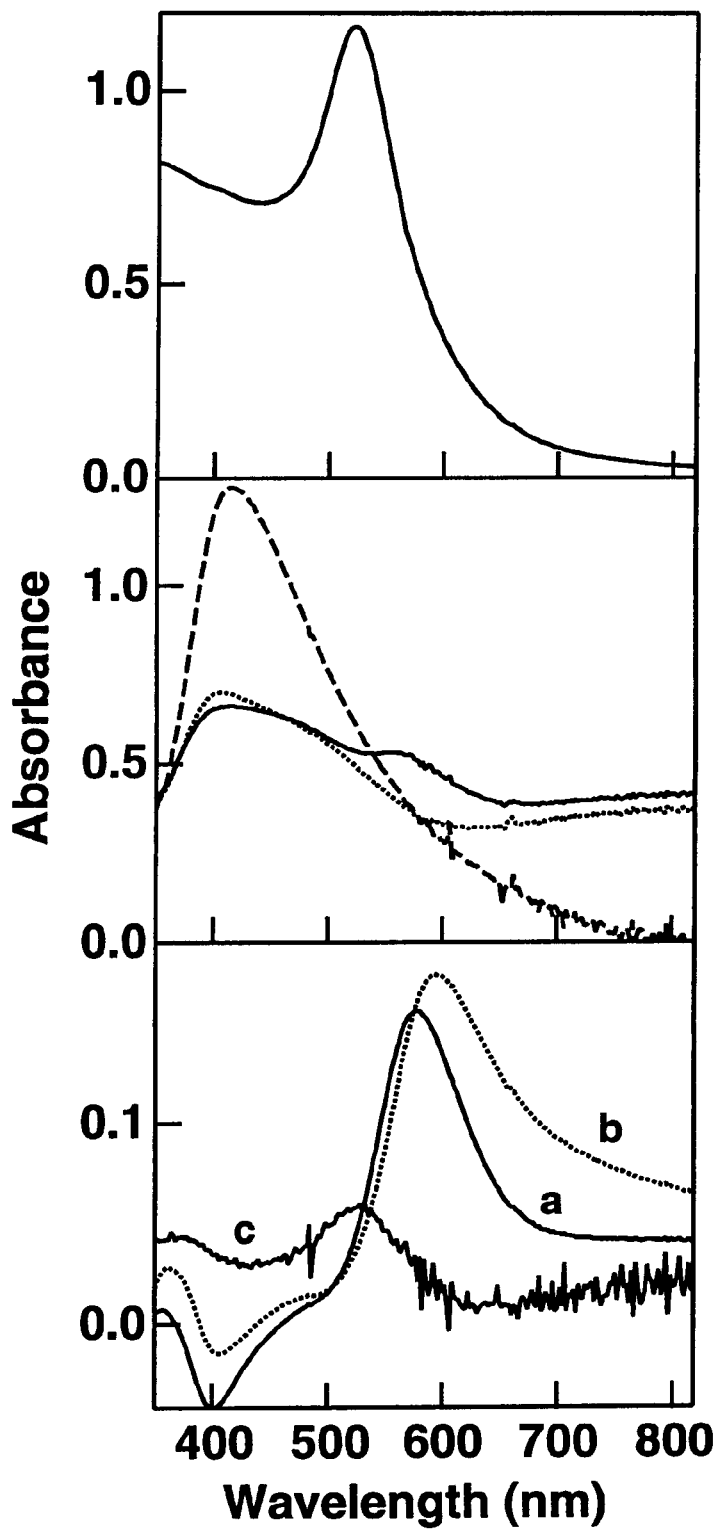
FIG. 26 shows the optical spectrum for Cc:Au conjugates (top), the optical spectra for unaggregated Ag sol (dashed line, - - - , diluted 1:4.3 with $H_2O$) and for SERS samples consisting of aggregated Ag sol with Cc (dotted line, ... ) and with Cc:Au (solid line, —) (middle), and (bottom) difference spectra for several SERS samples minus the spectrum for the aggregated Ag sol alone: (a) Cc:Au; (b) unconjugated 12-nm Au; and (c) HRP:Au.

SERS on aggregated metal colloids is highly dependent upon the absorbance properties and aggregation state of the particles. The optical spectrum of Cc:Au conjugates (FIG. 26, top panel) is essentially unchanged from that of the 12-nm diameter Au particles used in their preparation. A maximum at ~520 nm is present, due to the surface plasmon absorbance of the particles. Optical spectra for the citrate reduced Ag sol used in this work, and for Ag:Cc and Ag:Cc:Au SERS samples are also shown in FIG. 26 (middle panel). Aggregation of the Ag sol results in decreased extinction at $\lambda_{max}$ (~405 nm) and increased extinction at longer wavelengths. This is due to the replacement of single-particle plasmon oscillations by collective-particle oscillations, which occur at longer wavelengths. The broadness of these features indicates the presence of many different types of aggregates in the solution. Nevertheless, there is a clearly discernible shoulder between 550 and 600 nm for the Ag:Cc:Au sample that is not present in the Ag:Cc sample. (It should be noted here that it is possible to distinguish Ag:Cc:Au and Ag:Cc SERS samples by eye, the former being slightly purplish). A subtraction optical spectrum for the Ag:Cc:Au SERS sample minus an aggregated Ag "blank" (Ag:Cc:Au—Ag) is shown in the lower panel of FIG. 26 (curve a, solid line, i.e. —). Here the absorbance giving rise to the shoulder in the middle panel can be readily distinguished as a peak with $\lambda_{max}$=574 nm. This feature is only observed when Cc:Au conjugates are present in the sample, and the peak is significantly redshifted relative to the $\lambda_{max}$ for Cc:Au conjugates alone in solution (FIG. 26, top panel). Proximity to the aggregated Ag sol surface accounts for shifting the Cc:Au $\lambda_{max}$ to longer wavelengths. Thus, it appears that the data shown in FIG. 25 are reporting on the optical spectrum for the Ag:Cc:Au sandwich under interrogation in the SERS experiment, as distinct from the Ag aggregates as a whole or from the Cc:Au conjugates alone. Note that it cannot be expected that bulk optical properties (as measured by uv-vis) and the local optical properties at the sites giving rise to SERS scattering would necessarily be the same or even similar; nonetheless, in this case the SERS and absorbance spectra appear to be reporting on the same species. The data shown here cannot be accounted for without electromagnetic coupling between the Ag aggregates and the protein-coated Au particles; hence both must be participating in the observed enhancements. Indeed, the optical difference spectrum for uncoated Au (FIG. 26, bottom panel, curve b, dotted line, i.e. . . . ) is similar to that for Cc:Au, except that the $\lambda_{max}$ is redshifted even further, indicating an even greater degree of coupling between the Au particles and the Ag aggregates. This result is reasonable given the closer approach possible without the protein coating between the Au and Ag particles.

Much less coupling is observed upon replacing the Cc:Au conjugates with horseradish peroxidase:Au conjugates (HRP:Au). The optical difference spectrum for a SERS sample containing BRP:Au conjugates minus that of the Ag aggregate blank is also shown in the bottom panel of FIG. 26 (curve c). Even though the concentration of Au nanoparticles in all three samples for which difference spectra are shown in FIG. 26 are essentially the same, the absorbance of the Ag:HRP:Au—Ag is noticeably smaller. More importantly, it is essentially unshifted relative to the free conjugates with a $\lambda_{max}$=528 nm (in addition, curve c is nearly identical to the optical spectrum for the same concentration of uncoated Au nanoparticles in $H_2O$). The lack of peakshift of the 528 nm band for HRP:Au reflects poorer adsorption of conjugates to Ag aggregates.

The key point from the data in FIG. 26 is that the optical properties of cytochrome c-coated colloidal Au nanoparticles are strongly perturbed by aggregated Ag. In contrast, those of HRP:Au, which is not in close proximity to the Ag substrate, are not. The magnitude of the perturbation, as manifested by the shift in $\lambda_{max}$, reflects the separation between the Au nanoparticles and the aggregated Ag substrate. Au particles lacking protein coating can contact Ag aggregates directly, and their optical spectra are perturbed more than Cc:Au.

The next example furnishes additional evidence of strong wavelength-dependent electromagnetic coupling between the colloidal Au nanoparticles and the Ag substrate through the presence (or absence) of photoinduced conformational changes in Cc. It has been convincingly demonstrated that substrates with large surface electromagnetic fields are enhancing not only for SERS but for a variety of photon-driven phenomena, including second harmonic generation, fluorescence, and photochemistry. For Cc at metal surfaces, the most likely photoinduced processes are conformational changes affecting the heme pocket, including spin state conversion; such changes are readily detectable by SERS. Thus, Cc molecules sandwiched between Au and Ag surfaces might be expected to show greater instability with respect to laser illumination than Cc bound only to the Ag surface. This is indeed the case: we find greater photosusceptibility for Ag:Cc:Au than for Ag:Cc using 568.2 nm excitation. However, at 514.5 nm, an excitation wavelength for which the colloidal Au particle is "turned off", there is no difference in photostability between Ag:Cc:Au and Ag:Cc.

Figure 27:
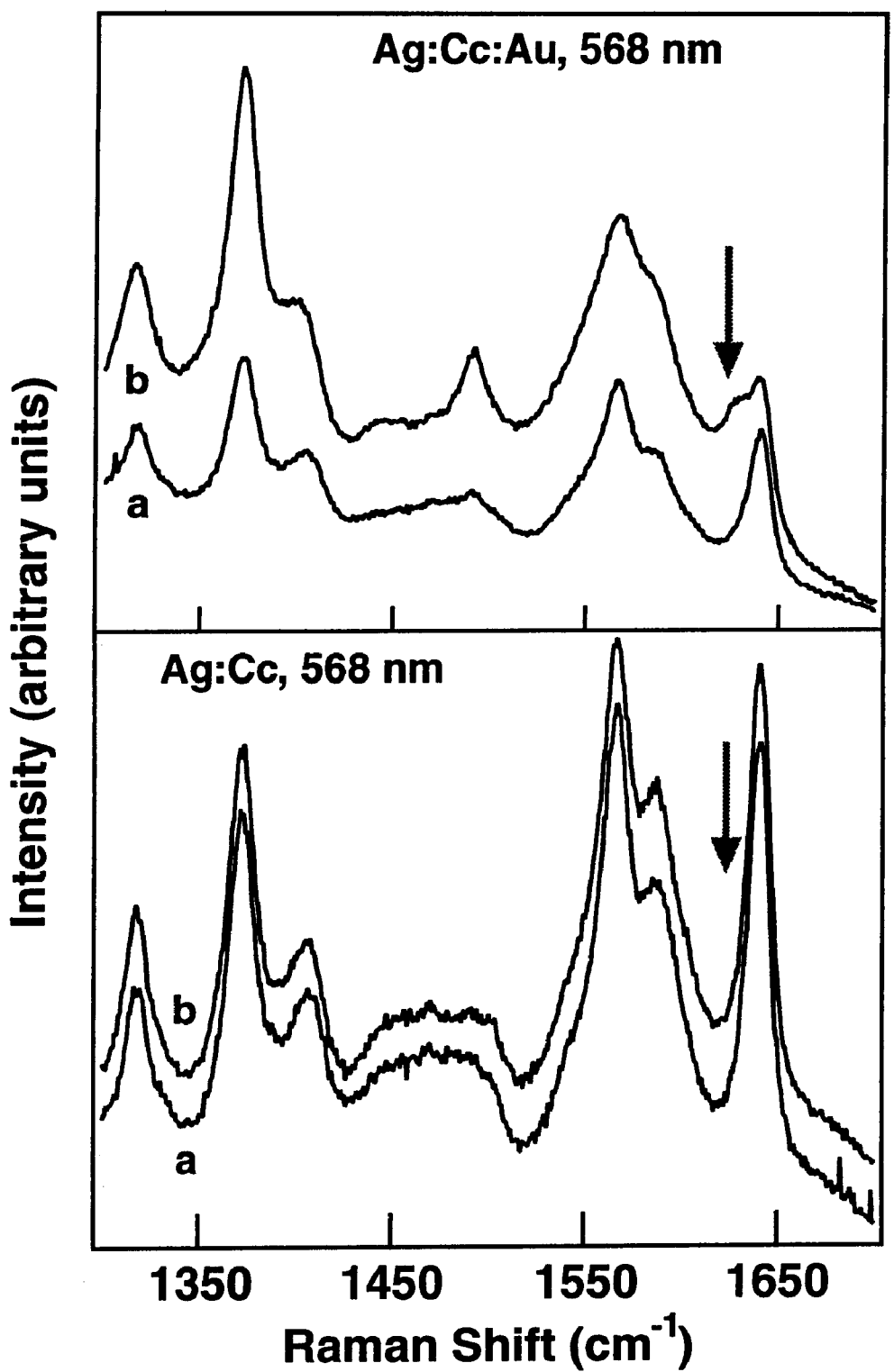
FIG. 27 shows SERS spectra at 568.2 nm excitation for Cc:Au conjugates (top) and Cc (bottom) adsorbed to aggregated colloidal Ag, taken immediately after SERS sample preparation (a) and after 30 minutes of irradiation (b).

FIG. 27 shows SERS spectra for Ag:Cc:Au (top panel) and Ag:Cc (bottom panel) immediately after sample preparation (a) and after samples were left in a ~50 mW, 568.2 nm beam for 30 minutes (b). (It should be noted that the irradiation time required to see these changes far exceeds that needed to acquire a SERS spectrum, and that no attempts were made to cool or mix samples during irradiation.) Several changes can be seen in the Ag:Cc:Au spectra. After 30 minutes, the overall signal has grown due to changes in aggregation state of the colloidal Ag; more importantly, the relative intensities of the bands (particularly $v_{10}$, $v_4$) have altered noticeably. In addition, a new vibration at ~1626 cm$^{-1}$ has appeared; the presence of this band indicates that some of the Fe has converted to a high spin state. Overall, the spectral changes for Ag:Cc:Au indicate that there has been some change in the structure of adsorbed Cc. In contrast, no such changes are observed in the spectra of Ag:Cc at the same concentration (FIG. 27, lower panel). Hence, it appears that Cc adsorbed directly to Ag is more stable to photoinduced conformational changes than is Cc:Au at 568.2 nm excitation.

Figure 28:
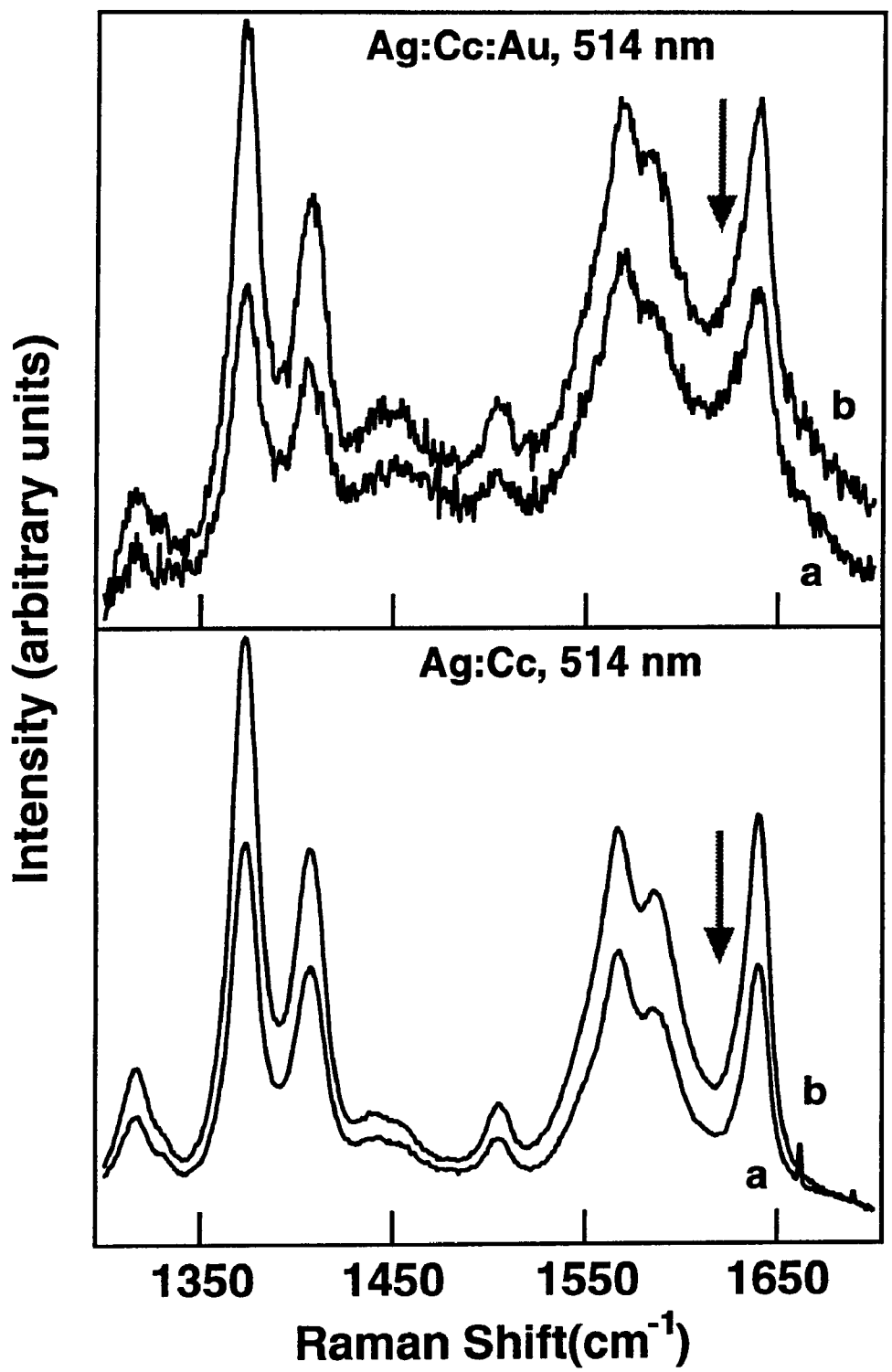
FIG. 28 shows SERS spectra at 514.5 nm excitation for Cc:Au conjugates (top) and Cc (bottom) adsorbed to aggregated colloidal Ag taken immediately after SERS sample preparation (a) and after 30 minutes of irradiation (b).

If the increased susceptibility to irradiation for Cc:Au as compared to Cc is due to the increased electromagnetic field experienced by Cc located between Au particles, then it should not be observed at excitation wavelengths for which there is damping of the surface plasmon. FIG. 28 shows SERS spectra for Cc:Au (top panel) and Cc (bottom panel) adsorbed to aggregated Ag before and after 30 minutes of irradiation with ~50 mW of 514.5 nm light. No evidence for spin state conversion or other conformational changes is observed in either sample. Thus, the changes observed in the Cc:Au spectra using 568.2 nm excitation can be attributed to the increased fields experienced by Cc molecules between Au nanoparticles and the surface of the Ag aggregates when both particles are "turned on".

Figure 29:
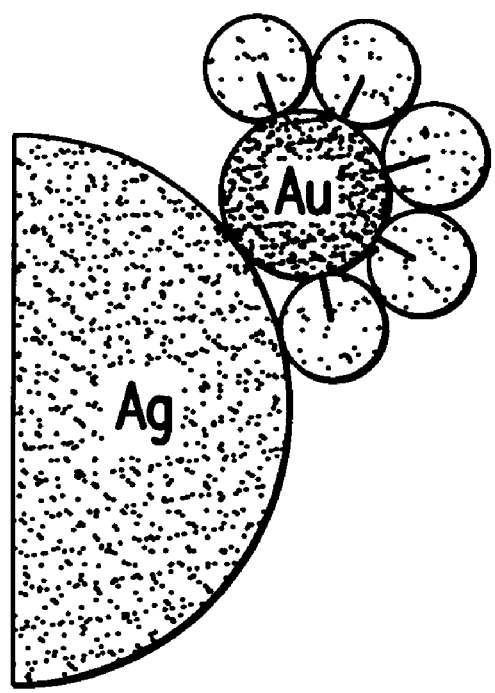
FIG. 29 shows a "squeezed sandwich" geometry.

These data are critical not only for demonstrating the wavelength dependence of the electromagnetic coupling between the Ag and Au particles but also for ruling out alternative geometries for B in FIG. 6. The most important of these is the "squeezed sandwich" geometry of FIG. 29, in which the Cc:Au conjugate is adsorbed to Ag, but with the Cc molecules that would be directly between the particles removed. Since none of the Cc molecules in the geometry of FIG. 29 are sandwiched between particles, they would not exhibit an increased EM field relative to A (i.e. directly adsorbed Cc), and consequently would not be expected to undergo a photoinduced spin-state conversion. That Ag:Cc:Au conjugates do so, but only at a wavelength where the colloidal Au particle contributes maximally to SERS, is compelling evidence against the geometry of FIG. 29, and for geometry B in FIG. 6.

Figure 30:
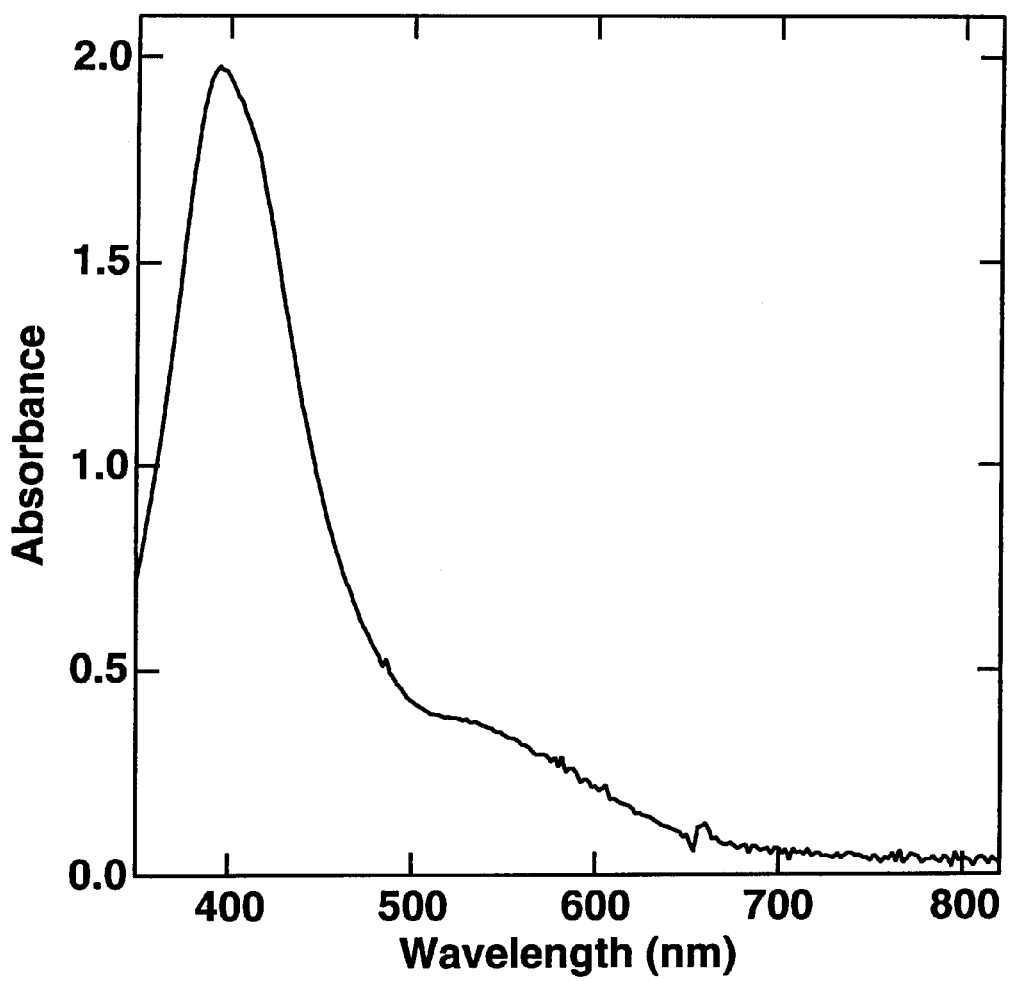
FIG. 30 shows an optical spectrum for Ag/Au particles used in preparation of Cc:Ag/Au conjugates.
Figure 31:
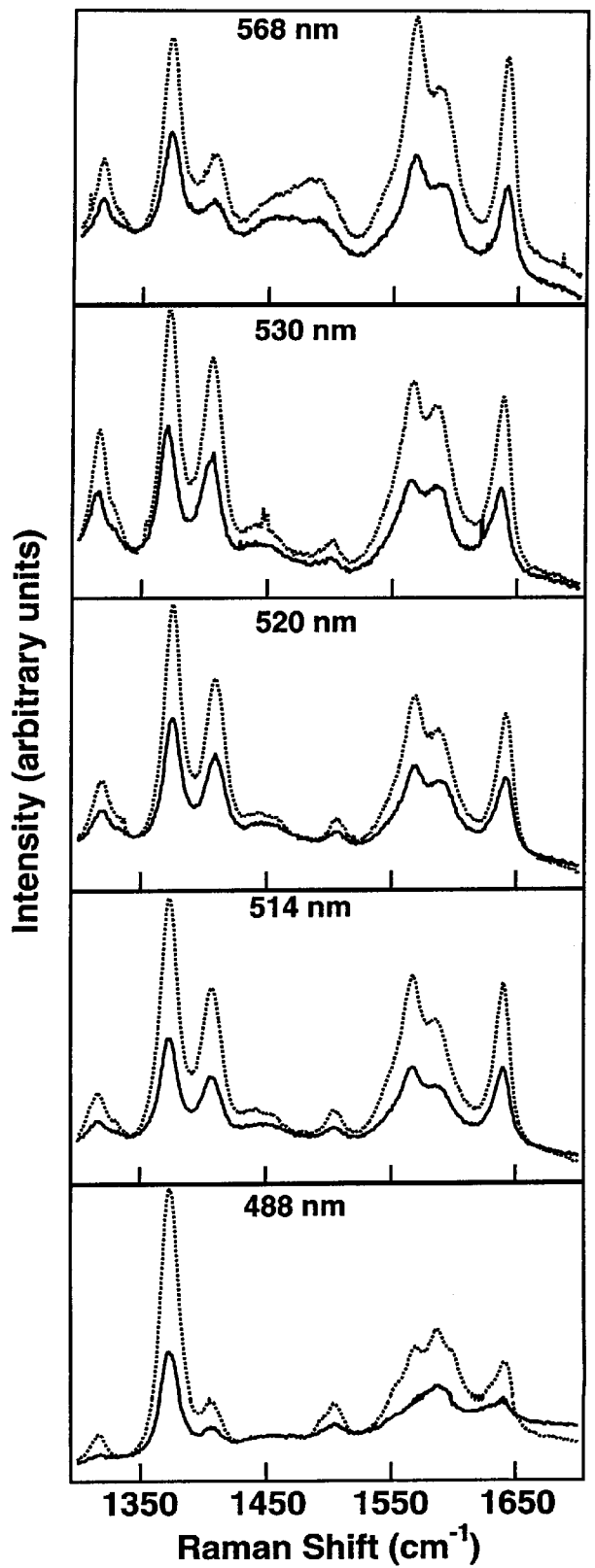
FIG. 31 shows SERS spectra at aggregated Ag sol for Cc (dotted line, ... ) and Cc:Ag-coated Au (solid line, —) at 568.2 nm, 530.9 nm, 520.8 nm, 514.5 nm, and 488.0 nm.
Figure 32:
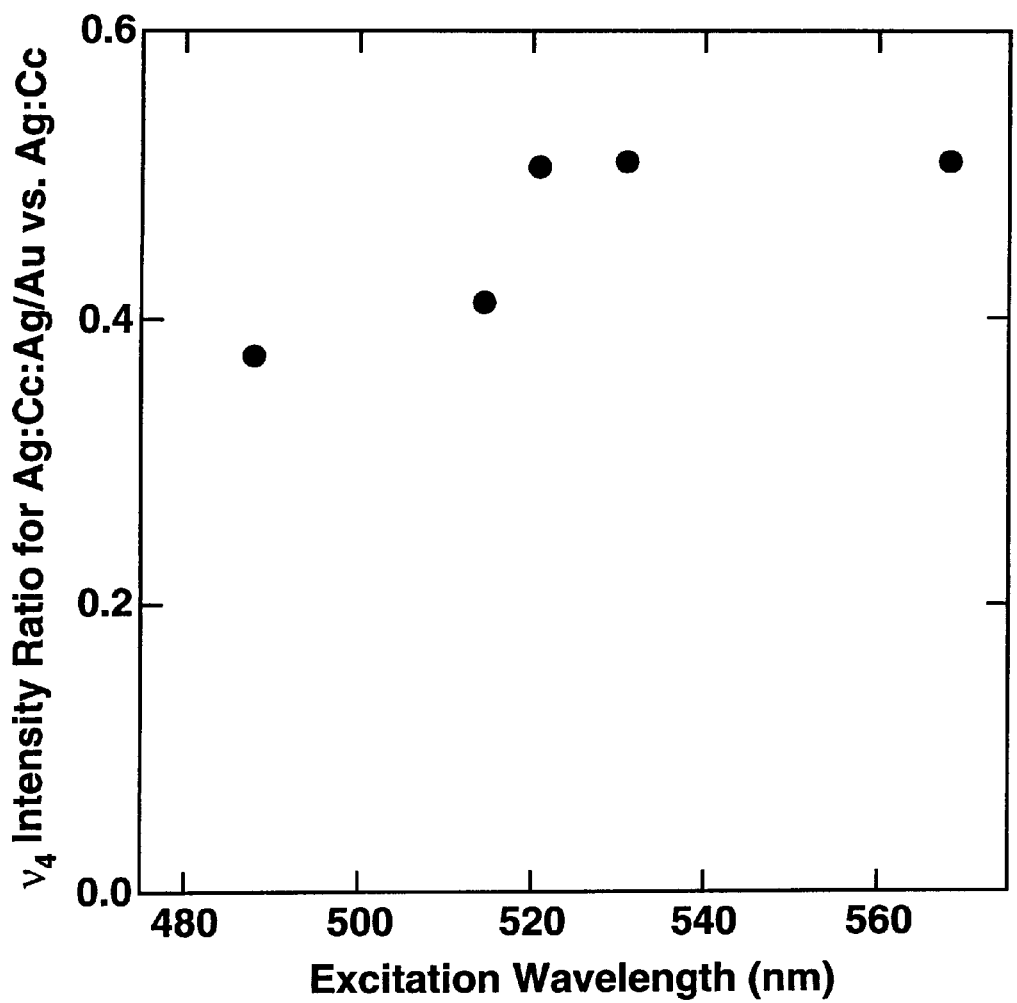
FIG. 32 shows the intensity ratio for $v_4$ band versus excitation wavelength for Ag:Cc:Au/Ag versus Ag:Cc.

The following example illustrates how particles other than 12-nm diameter colloidal Au, specifically Ag-clad Au, can be used to form sandwich structures. As a first step, the optical and SERS behavior of conjugates prepared with Ag/Au were explored. These particles comprised a 12-nm diameter colloidal Au core with a 3-nm thick Ag cladding. The addition of the Ag cladding dramatically alters the optical spectrum of the particles, with the Ag/Au particles exhibiting both Ag-like and Au-like surface plasmon bands (FIG. 30). As shown in FIG. 31, SERS spectra were acquired at five excitation wavelengths for Ag:Cc:Ag/Au and compared to the corresponding spectra for Ag:Cc under identical conditions. Once again, the latter yielded more intense spectra at all excitation wavelengths. A plot of $v_4$ intensity ratio of Ag:Cc:Ag/Au to Ag:Cc versus excitation wavelength is shown for this system in FIG. 32. However, the data differed from that of FIG. 25 in two major respects. First, the $v_4$ intensity ratios peaked at >0.5, as opposed to <0.4. Second, and more importantly, the data are nearly wavelength independent. Thus, while wavelength-dependent $v_4$ intensity ratios vary for Ag:Cc:Au by a factor of four, they only vary in Ag:Cc:Ag/Au by 50% or less. In other words, at all excitation wavelengths, Cc and Cc:Ag/Au yield comparable SERS intensities upon adsorption to aggregated Ag. The wavelength independence of these conjugates reflects wavelength-dependent contributions from both the Au core and the Ag cladding in different regions of the spectrum.

Figure 33:
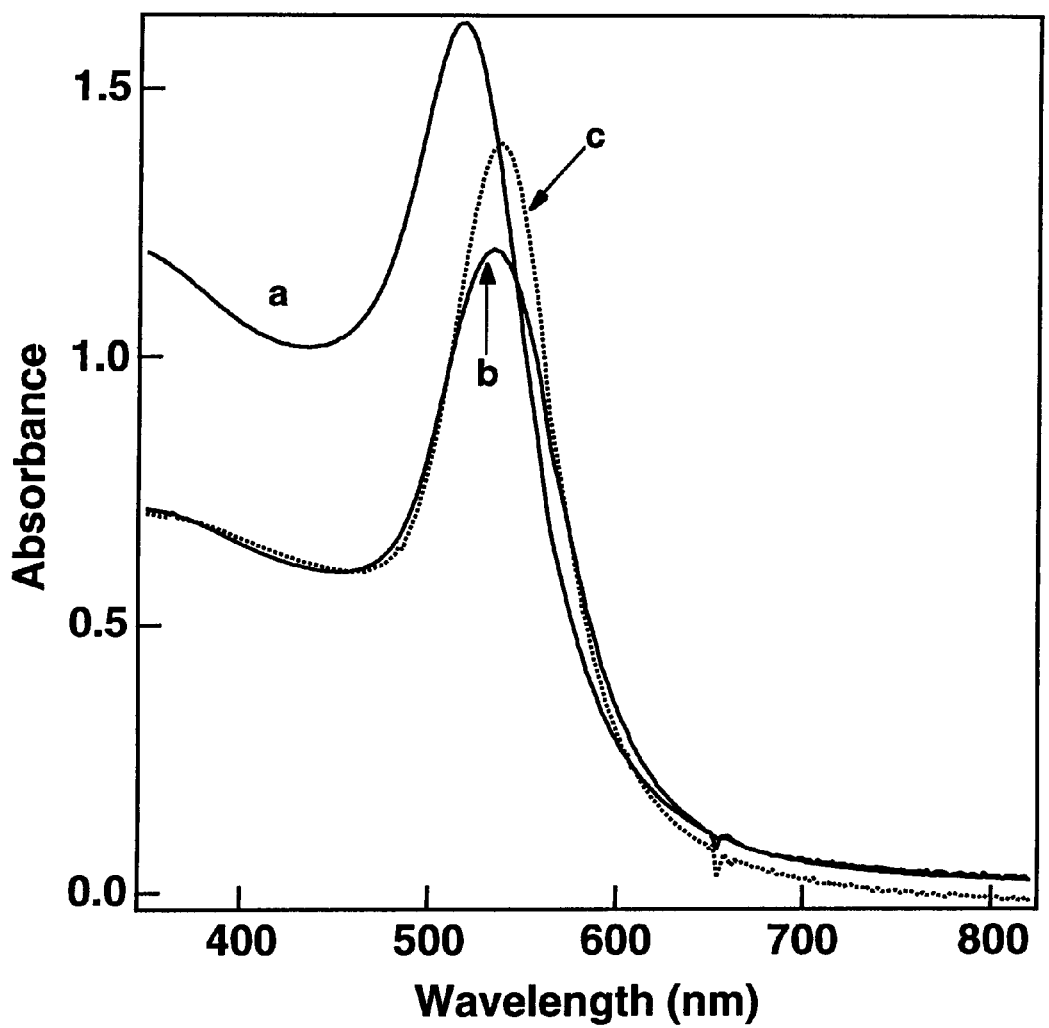
FIG. 33 shows optical spectra for (a) 12-nm diameter Au, diluted threefold in $H_2O$, 40-nm diameter Au, undiluted (b), and 60-nm diameter Au, undiluted (c).
Figure 34:
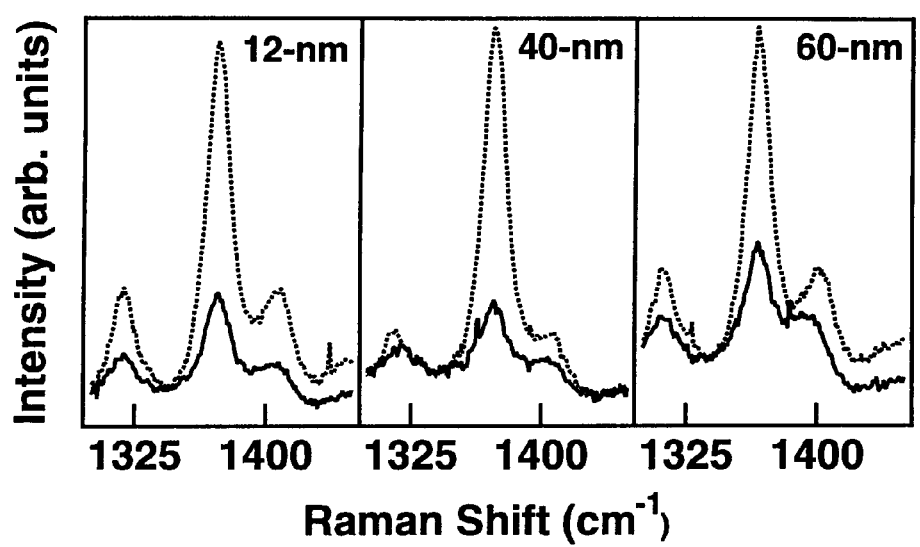
FIG. 34 shows SERS spectra for Cc:Au conjugates (solid line, —) prepared using colloidal Au with diameters of 12 nm, 40 nm, and 60 nm and for free Cc (dotted line, . . . ) at the concentration used in preparing the conjugates.

Another example illustrating the use of particles other than 12-nm diameter colloidal Au to form sandwiches concerns Au nanoparticles with diameters of 40 nm (Au(40)) and 60 nm (Au(60)). Cc conjugates were prepared using the aforementioned particles. The maximum for the surface plasmon absorbance occurs at 518 nm for conjugates prepared using 12-nm Au, at 534 nm for 40-nm Au, and at 538 nm for the 60-nm diameter Au particles (FIG. 33). Such particle size-dependent shifts in the position of $\lambda_{max}$ are expected, and could affect the observed SERS signal from Cc:Au adsorbed at colloidal Ag aggregates. Since the $v_4$ vibration at ~1375 cm$^{-1}$ is relatively insensitive to changes in Cc orientation (concentration), it is therefore the best band to examine for comparison between Cc and Cc:Au intensities for the various conjugates. Such a comparison indicates that there is a small but observable dependence of scattering intensity on particle diameter (FIG. 34).

Figure 35:
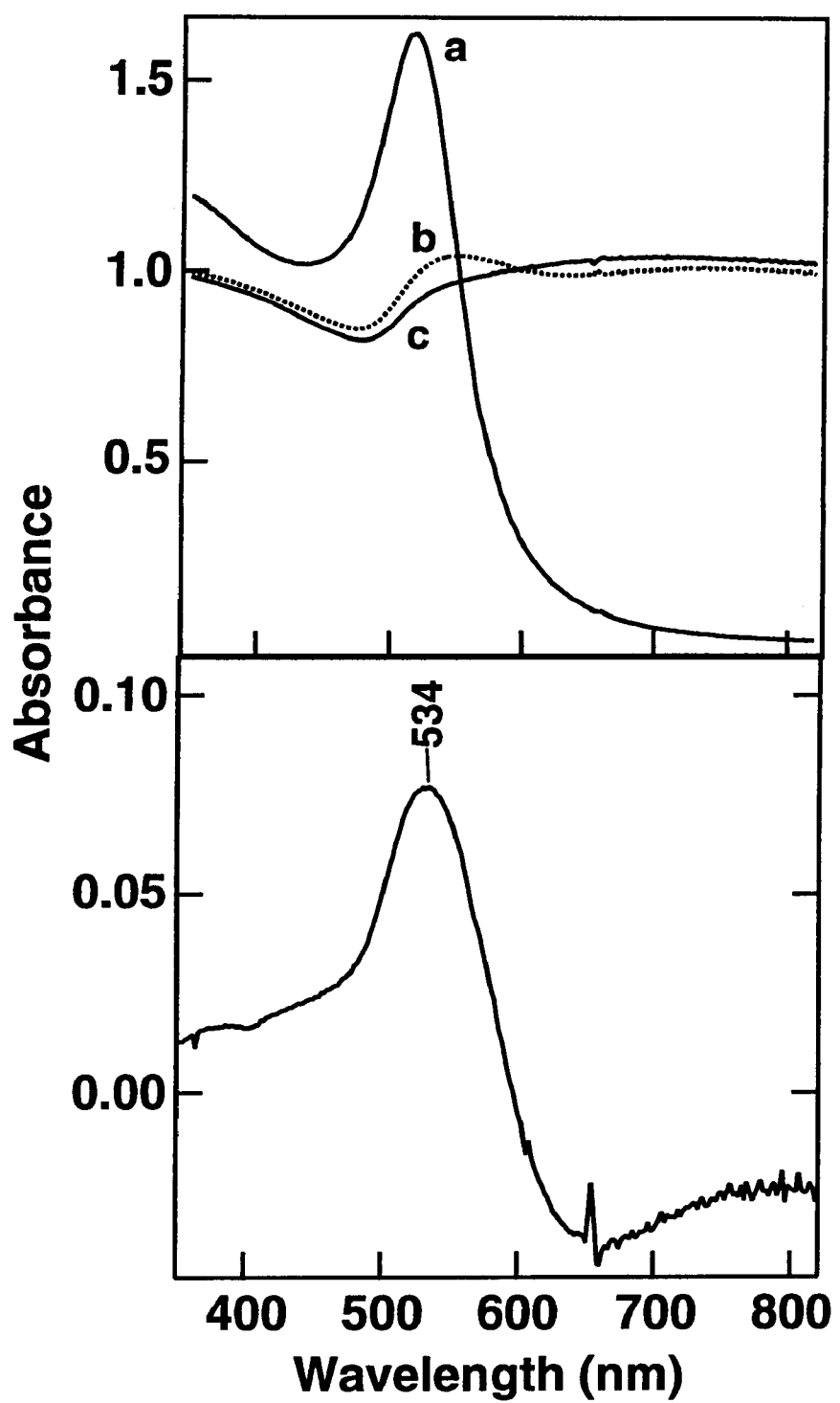
FIG. 35 shows optical spectra for unaggregated 12-nm colloidal Au (a), a SERS sample consisting of Cc:Au adsorbed to aggregated 12-nm colloidal Au, diluted 1:1 with $H_2O$ (b), and a SERS sample of Cc adsorbed to aggregated colloidal Au, diluted 1:1 with $H_2O$ (c) (top), and difference spectrum for (b)–(c) (bottom).
Figure 36:
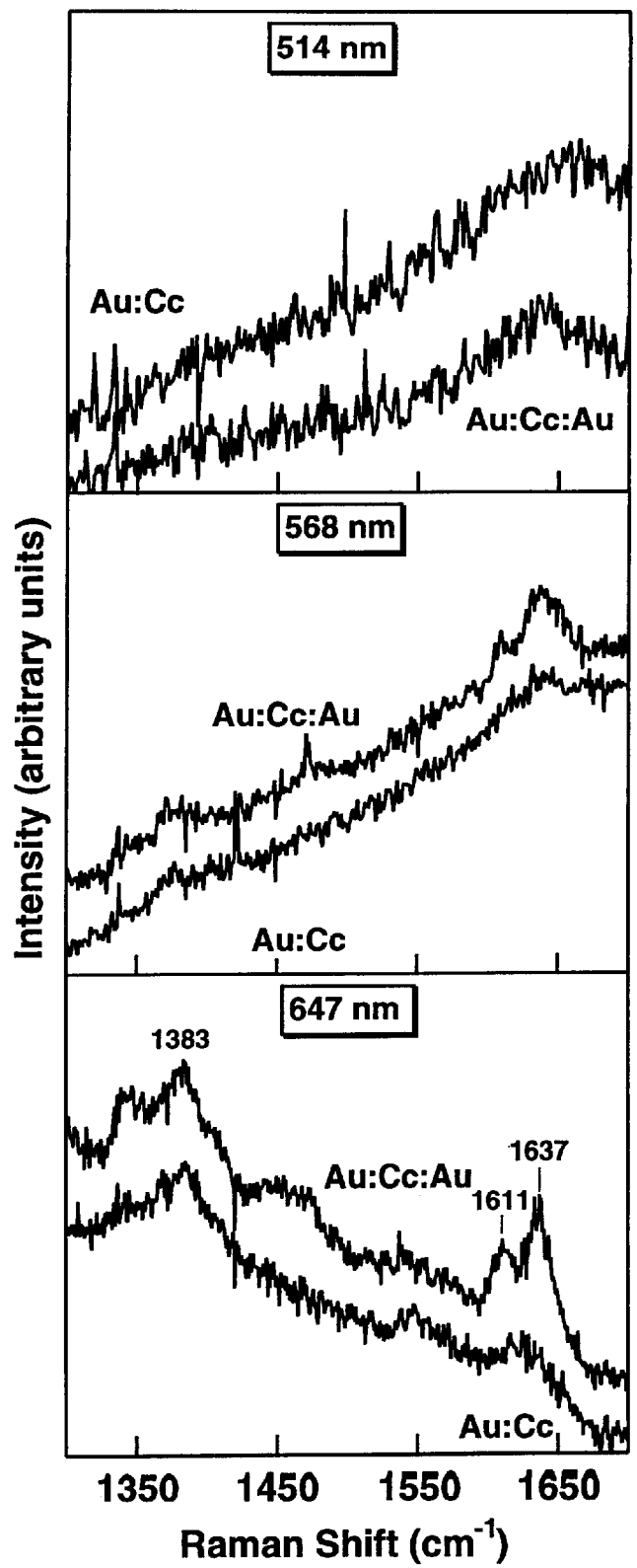
FIG. 36 shows SERS spectra for Au:Cc and Au:Cc:Au at excitation wavelengths of 514 nm, 568 nm, and 647 nm.

The next example shows how the substrate component of the sandwich can be changed. Specifically, this sandwich uses an aggregated Au sol as the SERS substrate, i.e. Au:Cc:Au. The top panel of FIG. 35 shows optical spectra for unaggregated 12-nm Au nanoparticles (trace a), aggregated 12-nm Au nanoparticles with adsorbed Cc:Au (trace b), and aggregated 12-nm Au nanoparticles with adsorbed Cc (trace c). The subtraction spectrum for spectrum (b) minus spectrum (c) is shown in the bottom panel of FIG. 35. The subtraction spectrum for Cc:Au on aggregated Au is similar to that for Cc:Au on aggregated Ag (FIG. 26, bottom), except that the peak is shifted only ~15 nm for the Au:Cc:Au, as compared to >50 nm for the Ag:Cc:Au sandwiches. This is consistent with the greater electromagnetic fields at the Ag aggregates relative to aggregates of 12-nm Au particles. SERS spectra for both Au:Cc:Au and Au:Cc at $\lambda_{ex}$=514.5, 568.2, and 647.1 nm are shown in FIG. 36. Due to weak SERS enhancement at Au aggregates as compared to Ag aggregates (even at long $\lambda_{ex}$) spectra exhibiting poor signal/noise ratios were obtained in all cases. No bands are observed in either Cc or Cc:Au SERS at Au aggregates for $\lambda_{ex}$=514.5 nm. Very weak bands due to Cc (at ~1375 and ~1635 cm$^{-1}$) are observed for $\lambda_{ex}$=568.2 nm and 647.1 nm in both data sets. SERS signal from Cc:Au is slightly better than that from Cc under these conditions. The wavelength dependence of the SERS spectra in FIG. 36 can be understood in terms of the effects of Au surface plasmon damping at short wavelengths, as for the corresponding system with Ag aggregates in place of Au aggregates. More importantly, the finding that the SERS intensity from Au:Cc:Au—although weak—exceeds that for Au:Cc reinforces the conclusion that the EM field strength between particles (in this case, Au) and aggregates is large compared to that surrounding Au aggregates.

Figure 37:
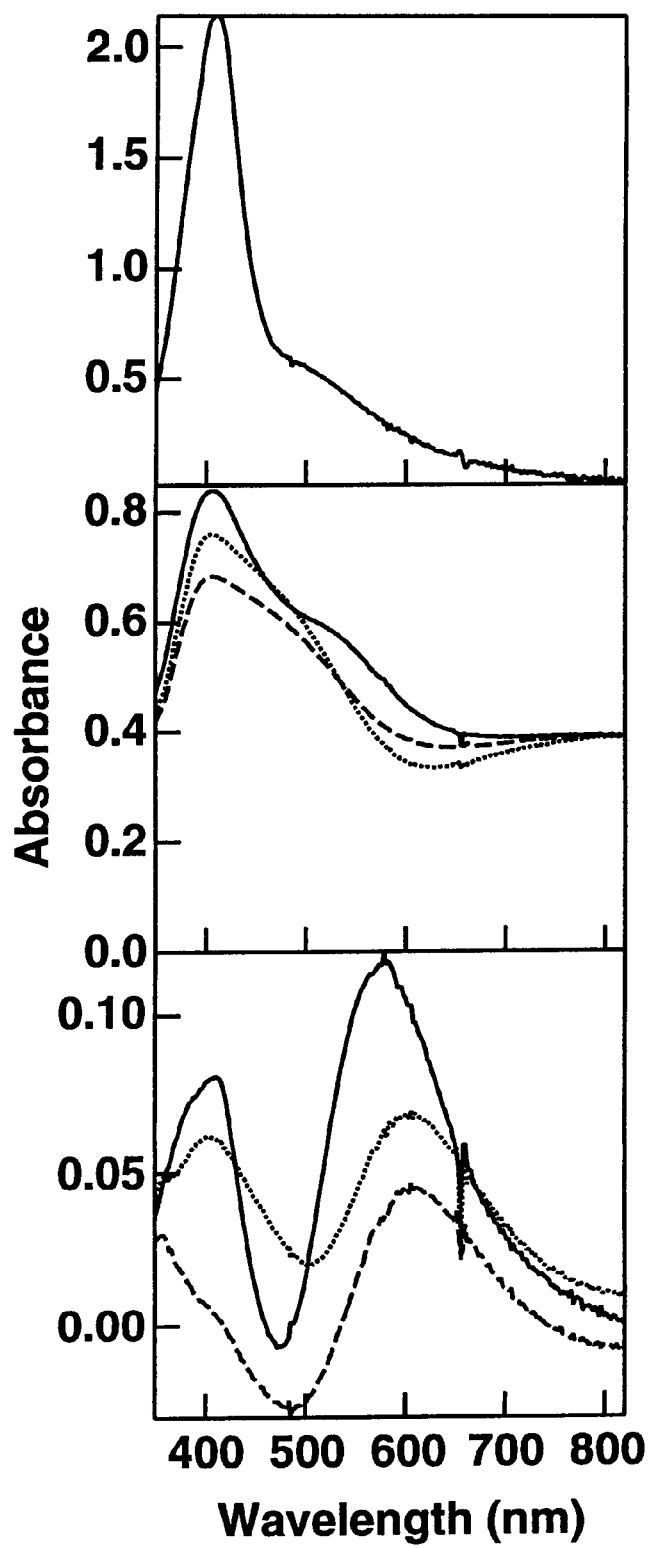
FIG. 37 shows an optical spectrum of Cc:Ag conjugates, diluted 1:5 with $H_2O$ (top), optical spectra for SERS samples consisting of aggregated Ag sol with added $H_2O$ (dotted line, . . . ), Cc (dashed line, - - - ), and Cc:Ag (solid line, —) (middle), and difference spectra for Cc:Ag SERS sample minus the spectrum for the aggregated Ag sol (solid line, —), for uncoated EDTA-reduced colloidal Ag added to citrate-reduced Ag sol before (dashed line, - - - ) and after (dotted line, . . . ) aggregation induced by addition of NaCl (bottom).
Figure 38:
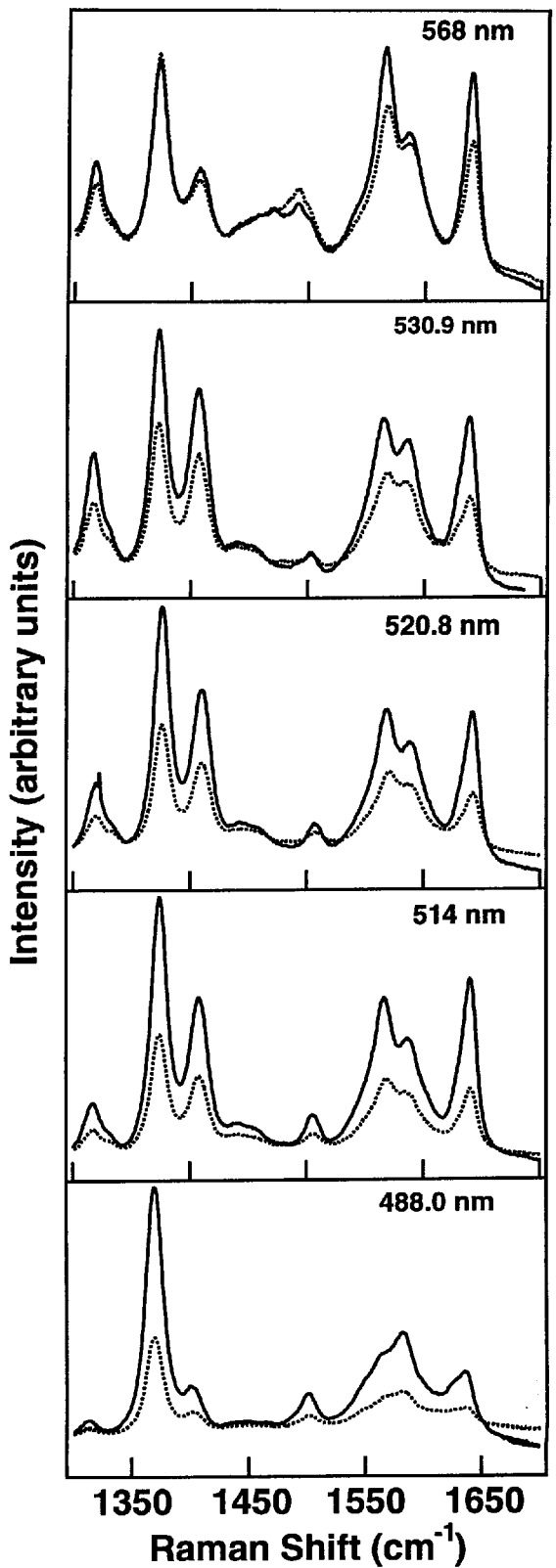
FIG. 38 shows SERS spectra at for Ag:Cc:Ag (solid line, —) and Ag:Cc (dotted line, . . . ) at 568.2 nm, 530.9 nm, 520.8 nm, 514.5 nm, and 488.0 nm.
Figure 39:
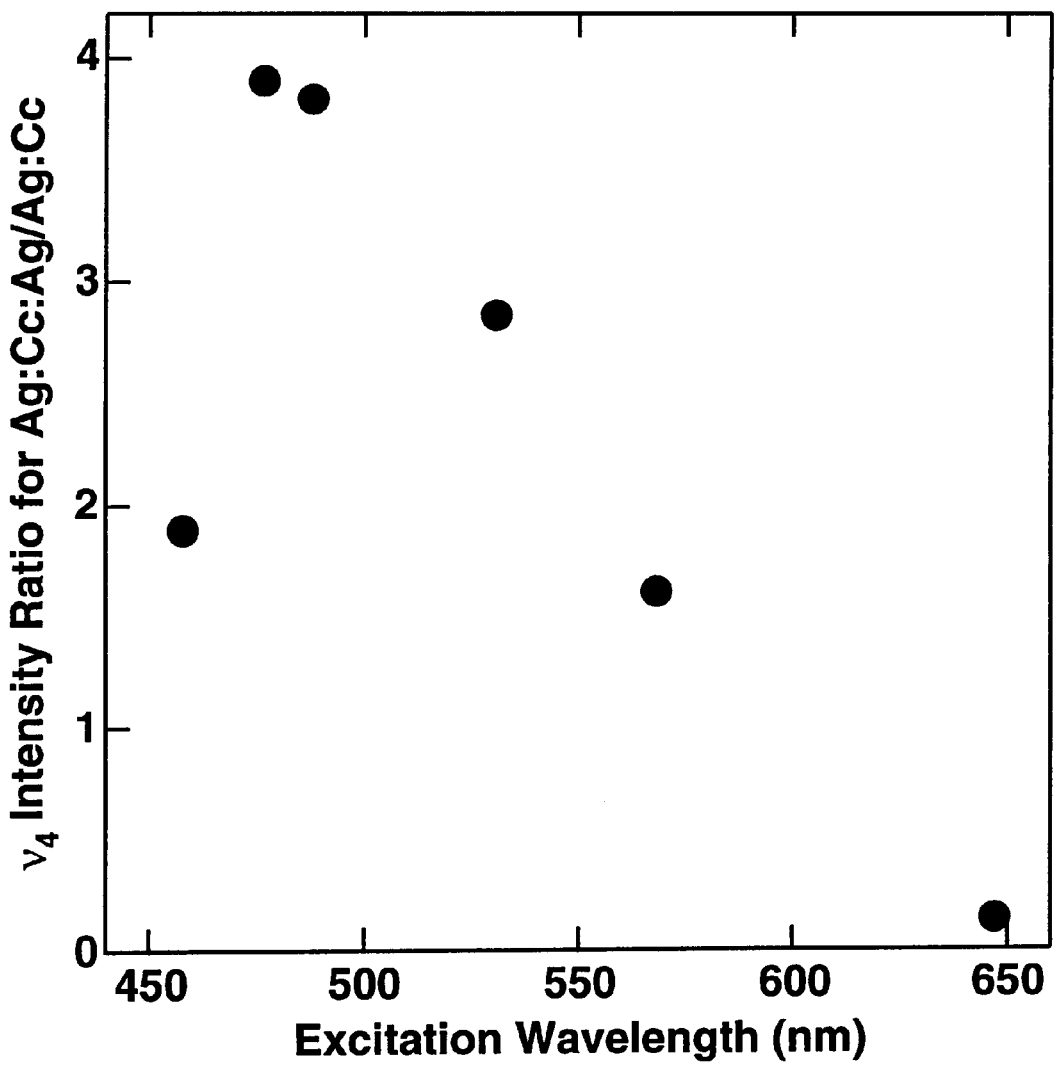
FIG. 39 shows the $v_4$ intensity ratio of Ag:Cc:Ag to Ag:Cc versus excitation wavelength.

Yet another example of changing the nanoparticle is that of Ag:Cc:Ag, i.e. a Cc:Ag nanoparticle conjugate adsorbed at an aggregated Ag sol. Cc:Ag conjugates were prepared and characterized optically, exhibitin an absorbance maximum at 408 nm, and a weaker, broad shoulder extending out to nearly 700 nm (FIG. 37, top panel). The absorbance spectrum for a Cc:Ag SERS sample (i.e. Ag:Cc:Ag) is shown in the middle panel FIG. 37 (solid line), along with the spectra for SERS samples containing Cc and $H_2O$ as analyte (each sample has aggregated Ag sol as substrate). Only the Ag:Cc:Ag sample has a shoulder ~550 nm. This feature is due to a peak at 580 nm observable in the optical difference spectrum for this sample minus an aggregated Ag blank (FIG. 37, bottom panel, solid line). For comparison, difference spectra for uncoated EDTA-reduced Ag sol added to citrate-reduced Ag sol before (dashed line, i.e. - - - ) and after aggregation (dotted line, i.e. . . . ) are also shown in the bottom panel of FIG. 37. Both difference spectra for uncoated Ag are qualitatively similar to that for Cc:Ag, except that the large feature is less intense and located further to the red (~600 nm) for the uncoated Ag difference spectra. None of these difference spectra bears much resemblance to unaggregated EDTA-reduced Ag sol, or to Cc:Ag. Due to similarities in the absorbance spectra of, and greater EM coupling between, Ag aggregates and Cc-coated Ag nanoparticles (as compared to Cc-coated 12-nm Au), it is more difficult to separate the contribution of Cc:Ag from that of the bulk aggregated Ag. SERS spectra of Ag:Cc and Ag:Cc:Ag at five excitation wavelengths are presented in FIG. 38. At each $\lambda_{ex}$ shown, Ag:Cc:Ag spectra (solid lines) are more intense than Ag:Cc (dashed lines). Once again, it is important to point out that spectra were acquired with the same total (Cc), the same laser power and integration time (for a given $\lambda_{ex}$) and for identically prepared samples. This shows that enhancement due to location between the Ag nanoparticle of the conjugate and the Ag aggregate more than compensates for the decrease in signal caused by the longer distance between the Ag aggregates and the Cc heme group. Unlike the Cc:Au conjugates, Cc:Ag conjugates give optimal SERS at shorter $\lambda_{ex}$. A plot of the $v_4$ intensity ratio of Ag:Cc:Ag/Ag:Cc vs. $\lambda_{ex}$ is shown in FIG. 39. Not surprisingly, the maximal benefits of Cc:Ag conjugates are realized at shorter excitation wavelengths: for example, at 488.0 nm, the $v_4$ intensity of Cc:Ag adsorbed at aggregated Ag is four times that of directly adsorbed Cc. Considering how few of the Cc molecules are actually sandwiched, this is an impressive increase. At the very least, it offers a practical prescription for increased SERS intensities for a sandwiched analyte.

Figure 40:
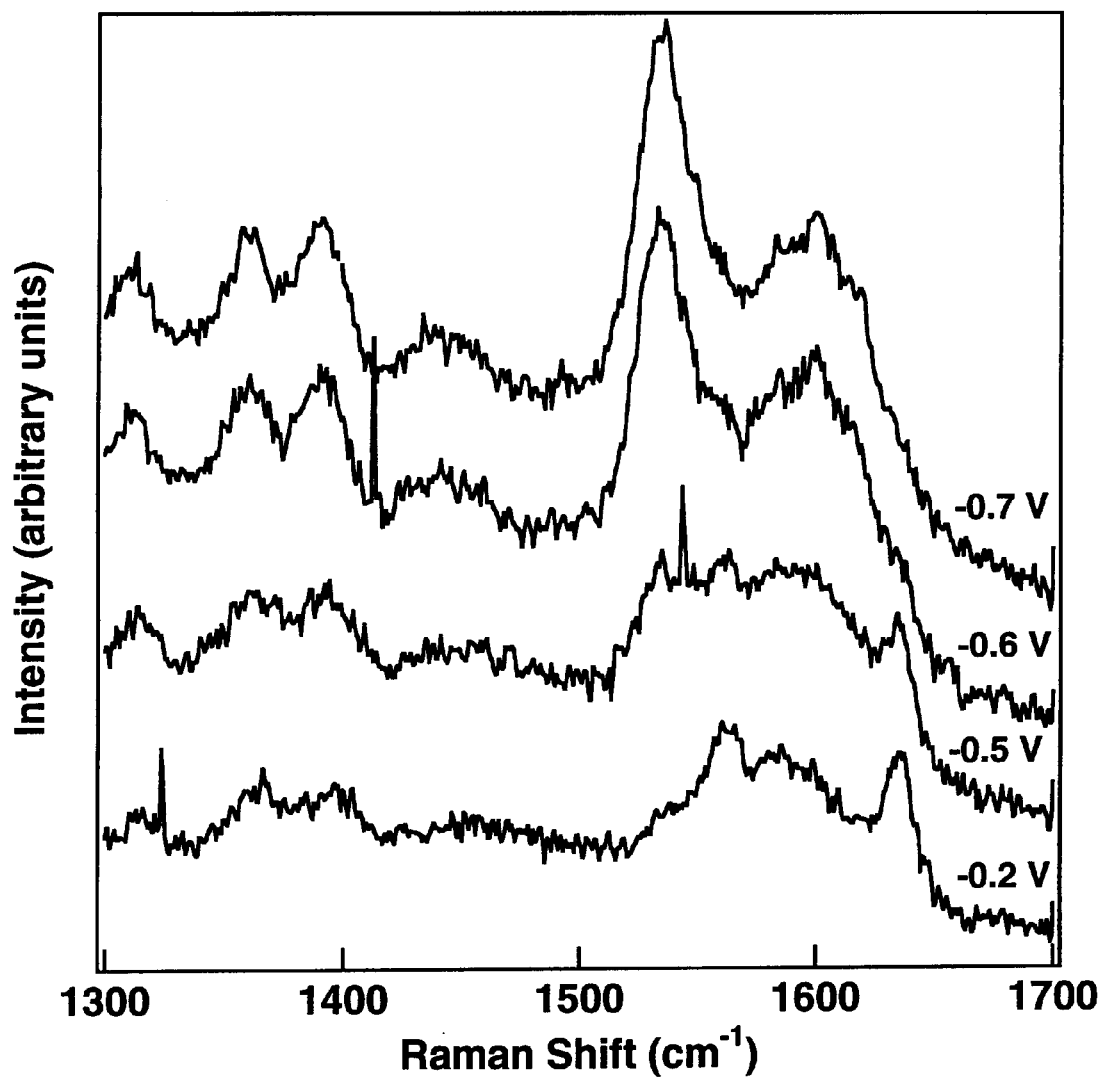
FIG. 40 shows the electrochemical potential dependence of the Cc SERS spectrum for Cc:Au covalently bound to a roughened Ag electrode.

A final example concerns the use of macroscopic SERS substrates. FIG. 40 shows SERS data for sandwiches comprising Cc:Au complexes covalently bound (using carbodiimide coupling) to roughened Ag electrodes coated with 2-mercaptoethylamine. The change in SERS intensity as a function of electrochemical potential indicates close proximity of the Cc:Au complex to the electrode surface. These data also show that derivatization of the SERS substrate (here with a self-assembled monolayer of 2-mercaptoelthylamine) in no way inhibits either sandwich formation or spectral acquisition.

Note that while the examples above describe sandwiches made with colloidal Au nanoparticles of various sizes between 12–60 nm, of Ag-clad Au nanoparticles, and of Ag nanoparticles, this is in no way limiting: the nanoparticle component of the sandwich can comprise particles of virtually any size smaller than visible wavelengths, any of several additional metals (Al, Cr, Cu, etc.), alloys of two or more metals, and inhomogeneous mixtures of two or more metals. Likewise, while the examples described herein have the analyte in direct contact with metal nanoparticle surfaces, a variety of surface-functionalized nanoparticles can be used. Such functionalization can take the form of a coating or thin film of any SERS-active or non-SERS active metal, a polymer or biopolymer, or mixtures thereof, a self-assembled monolayer of organothiols, organoisocyanides, and the like, metal oxides, or other nanoparticles. Such film can be continuous or discontinuous, and of any thickness, as long as there is still an increased electromagnetic field at coating/surrounding interface.

By the same token, while examples of the SERS substrate component of the sandwich consisted of aggregated Ag and Au sols and a macroscopic roughened Ag electrode, any previously described nanostructure that supports SERS can be used. Likewise, all the coatings described above with reference to the nanoparticle are equally viable for the SERS substrate, and not merely the organothiol self-assembled monolayer actually illustrated.

Additionally, while the examples above focused on Cc as the sandwiched analyte, there are numerous covalent and non-covalent routes to position small molecules, polymers, large biomolecules (proteins, nucleic acids), and nanoparticles (metals, oxides, etc.) between the SERS-active substrate and the metal nanoparticle.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. A nanometer scale structure for surface enhanced Raman scattering (SERS) comprising three proximal components:
   (a) a SERS-active metal substrate
   (b) a colloidal metal nanoparticle
   (c) an analyte sandwiched between the substrate and particle
   such that a shortest distance between the metal nanoparticle surface and the metal substrate surface is between 1 and 50 nanometers.

2. The invention as defined in claim 1 wherein said SERS-active metal substrate is selected from the group consisting of: Au, Ag, Cu, Al, Cr, and Na.

3. The invention as defined in claim 1 wherein said SERS-active metal substrate comprises an alloy of two or more elements selected from the group consisting of: Au, Ag, Cu, Al, Cr, and Na.

4. The invention as defined in claim 1 wherein said SERS-active metal substrate comprises an inhomogeneous mixture of two or more elements selected from the group consisting of: Au, Ag, Cu, Al, Cr, and Na.

5. The invention as defined in claim 1 wherein said SERS-active metal substrate comprises a substance having two or more continuous layers of elements selected from the group consisting of: Au, Ag, Cu, Al, Cr, and Na.

6. The invention as defined in claim 1 wherein said SERS-active metal substrate comprises a composite material with domains of the elements Au, Ag, Cu, Al, Cr, Na, or an alloy of any two of said elements, such that one dimension of a domain measures between 10 nanometers and 1 millimeter.

7. The invention as defined in claim 1 wherein said SERS-active metal substrate is selected from the group consisting of aggregated metal nanoparticles, discontinuous films, and continuous films.

8. The invention as defined in claim 1 wherein said SERS-active metal substrate is coated with a continuous or discontinuous film.

9. The invention as defined in claim 8 wherein the film is a metal chosen from the $3^{rd}$, $4^{th}$, or $5^{th}$ row of the periodic table of the elements.

10. The invention as defined in claim 8 wherein the film is a self-assembled monolayer.

11. The invention as defined in claim 8 wherein the film is a polymer, a biopolymer, a mixture of polymers and biopolymers or a mixture of polymers or biopolymers.

12. The invention as defined in claim 8 wherein the film is a metal oxide, sulfide, nitride, or phosphide, such that the metal is chosen from the $3^{rd}$, $4^{th}$, or $5^{th}$ row of the periodic table of the elements.

13. The invention as defined in claim 1 wherein said metal nanoparticle is selected from the group consisting of: Au, Ag, Cu, Al, Cr, and Na.

14. The invention as defined in claim 1 wherein said metal nanoparticle comprises an alloy of two or more elements selected from the group consisting of: Au, Ag, Cu, Al, Cr, and Na.

15. The invention as defined in claim 1 wherein said metal nanoparticle comprises an inhomogeneous mixture of two or more elements selected from the group consisting of: Au, Ag, Cu, Al, Cr, and Na.

16. The invention as defined in claim 1 wherein said metal nanoparticle comprises a substance having two or more continuous layers of elements selected from the group consisiting of: Au, Ag, Cu, Al, Cr, and Na.

17. The invention as defined in claim 1 wherein said metal nanoparticle is attached covalently or non-covalently to a carrier consisting of a non-SERS active colloidal particle or a scanned probe microscopy tip.

18. The invention as defined in claim 1 wherein said metal nanoparticle has at least one dimension between 2 and 200 nanometers.

19. The invention as defined in claim 1 wherein said metal nanoparticle is spherical, elliptical, cylindrical, cubic, or plate-like.

20. The invention as defined in claim 1 wherein said metal nanoparticle is coated with a continuous or discontinuous film.

21. The invention as defined in claim 20 wherein the film is a metal chosen from the $3^{rd}$, $4^{th}$, or $5^{th}$ row of the periodic table of the elements.

22. The invention as defined in claim 20 wherein the film is a self-assembled monolayer.

23. The invention as defined in claim 20 wherein the film is a metal oxide, sulfide, nitride, or phosphide, such that the metal is chosen from the $3^{rd}$, $4^{th}$, or $5^{th}$ row of the periodic table of the elements.

24. The invention as defined in claim 20 wherein the film comprises a covalently— or non-covalently bound monolayer of SERS-active metal nanoparticles.

25. The invention as defined in claim 20 wherein the film is a polymer, a biopolymer, or a mixture of polymers and/or biopolymers.

26. The invention as defined in claim 20 wherein the film comprises a polypeptide, an oligonucleotide, or a lipid.

27. The invention as defined in claim 1 wherein said analyte is a molecule, a polymer, or a nanoparticulate substance.

28. The invention as defined in claim 1 wherein said analyte is bound covalently or non-covalently to the colloidal metal nanoparticle.

29. The invention as defined in claim 1 wherein said analyte is bound covalently or non-covalently to the SERS-active substrate.

30. The invention as defined in claim 1 wherein the structure is self-assembled in a single step.

31. The invention as defined in claim 1 wherein the structure is self-assembled in a stepwise fashion.

* * * * *